United States Patent
Lieberman et al.

(10) Patent No.: US 11,793,749 B2
(45) Date of Patent: Oct. 24, 2023

(54) PHARMACEUTICAL FORMULATIONS OF TROPOMYOSIN RELATED KINASE (TRK) INHIBITORS

(71) Applicant: GENZYME CORPORATION, Cambridge, MA (US)

(72) Inventors: Harvey Lieberman, Bridgewater, NJ (US); Donglai Yang, Bridgewater, NJ (US); C. Michael Philbrook, Boston, MA (US); Michael Santos, Cambridge, MA (US); Chris Ho, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 22 days.

(21) Appl. No.: 17/407,419

(22) Filed: Aug. 20, 2021

(65) Prior Publication Data
US 2022/0110861 A1    Apr. 14, 2022

Related U.S. Application Data

(63) Continuation of application No. 16/239,904, filed on Jan. 4, 2019, now Pat. No. 11,110,055, which is a (Continued)

(51) Int. Cl.
*A61K 31/00* (2006.01)
*A61K 9/00* (2006.01)
(Continued)

(52) U.S. Cl.
CPC .......... *A61K 9/0019* (2013.01); *A61K 9/1694* (2013.01); *A61K 9/5026* (2013.01);
(Continued)

(58) Field of Classification Search
CPC ....... C07D 401/14; A61K 31/00; A61P 19/02; A61P 25/04; A61P 29/00
See application file for complete search history.

(56) References Cited

U.S. PATENT DOCUMENTS

| | | | |
|---|---|---|---|
| 4,612,323 A | 9/1986 | Kisida et al. | |
| 4,663,339 A | 5/1987 | Kisida et al. | |

(Continued)

FOREIGN PATENT DOCUMENTS

| | | |
|---|---|---|
| CA | 2089689 A1 | 8/1993 |
| EP | 132606 A1 | 2/1985 |

(Continued)

OTHER PUBLICATIONS

Handbook of Pharmaceutical Excipients, 6th Ed, 2009, p. 581-585 and 679-682 (Year: 2009).*

(Continued)

*Primary Examiner* — San Ming R Hui
(74) *Attorney, Agent, or Firm* — Dechert LLP; Chad E. Davis

(57) ABSTRACT

Pharmaceutical formulations with a tropomyosin-related kinase inhibitor ("Trk inhibitor") are disclosed. The pharmaceutical formulations comprise 3-(3-methoxy-4-((4-methoxybenzyl)oxy)benzyl)-6-(1-methyl-1H-pyrazol-4-yl)-3H-imidazo[4,5-b]pyridin-2-amine in microcrystalline suspension formulations in its monohydrate form, which shows improved characteristics over the anhydrate form, and in extended release formulations. The extended release pharmaceutical formulations comprise 3-(3-methoxy-4-((4-methoxybenzyl)oxy)benzyl)-6-(1-methyl-1H-pyrazol-4-yl)-3H-imidazo[4,5-b]pyridin-2-amine-loaded microspheres.

16 Claims, 35 Drawing Sheets

Figure 1:
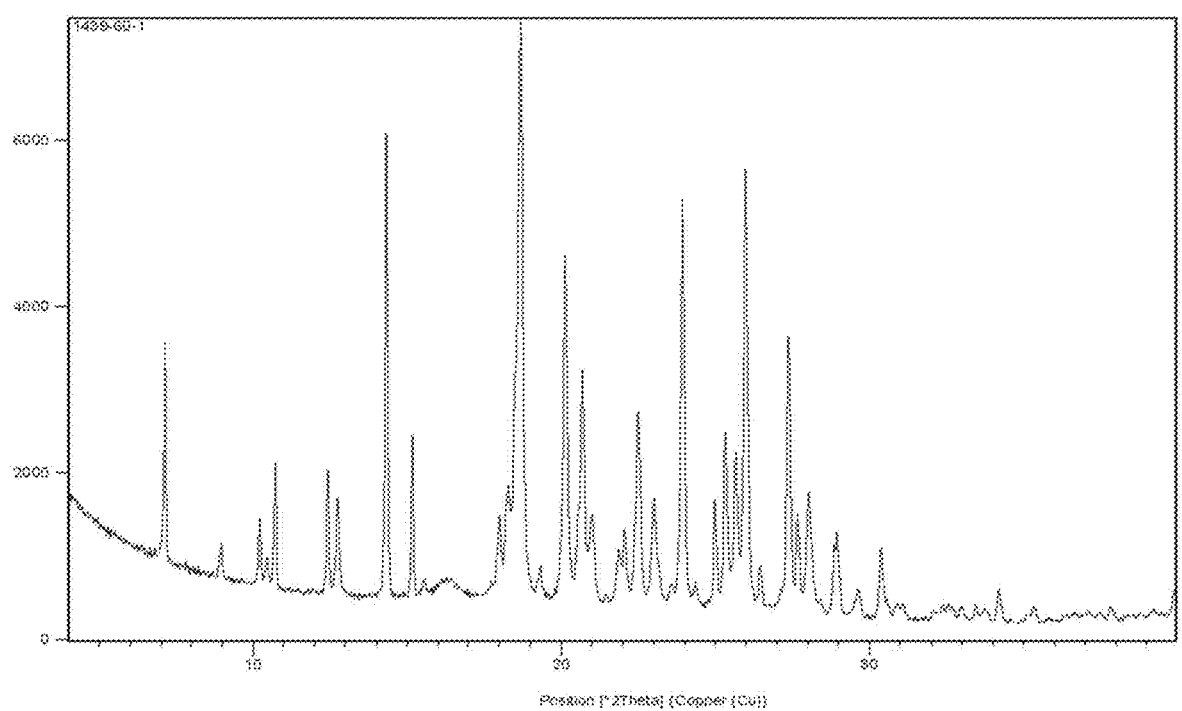

Related U.S. Application Data continuation of application No. 15/536,544, filed as application No. PCT/US2015/066396 on Dec. 17, 2015, now Pat. No. 10,219,998.

(60) Provisional application No. 62/093,801, filed on Dec. 18, 2014.

(51) Int. Cl.

| | |
|---|---|
| *A61K 47/10* | (2017.01) |
| *A61K 47/26* | (2006.01) |
| *C07D 471/04* | (2006.01) |
| *A61K 9/16* | (2006.01) |
| *A61K 9/50* | (2006.01) |
| *C07D 401/14* | (2006.01) |

(52) U.S. Cl.
CPC .............. *A61K 47/10* (2013.01); *A61K 47/26* (2013.01); *C07D 401/14* (2013.01); *C07D 471/04* (2013.01); *A61K 31/00* (2013.01); *C07B 2200/13* (2013.01)

(56) References Cited

U.S. PATENT DOCUMENTS

| | | | |
|---|---|---|---|
| 5,441,969 A | 8/1995 | Axelsson et al. | |
| 5,702,637 A | 12/1997 | Johnson et al. | |
| 5,972,241 A | 10/1999 | Johnson et al. | |
| 7,067,665 B2 | 6/2006 | Nazare et al. | |
| 7,312,214 B2 | 12/2007 | Qiao et al. | |
| 7,462,427 B2 | 12/2008 | Goodby et al. | |
| 7,465,825 B2 | 12/2008 | Van Zandt et al. | |
| 7,491,748 B2 | 2/2009 | Tani et al. | |
| 7,582,652 B2 | 9/2009 | Bonjouklian et al. | |
| 7,799,820 B2 | 9/2010 | Takahashi et al. | |
| 9,067,914 B1 * | 6/2015 | Kane, Jr. .............. | C07D 471/04 |
| 9,174,986 B2 | 11/2015 | Kane, Jr. et al. | |
| 9,611,265 B2 | 4/2017 | Kane, Jr. et al. | |
| 10,166,239 B2 | 1/2019 | Kane, Jr. et al. | |
| 10,219,998 B2 | 3/2019 | Lieberman et al. | |
| 11,110,055 B2 | 9/2021 | Lieberman et al. | |
| 2004/0002145 A1 | 1/2004 | Shewchuk et al. | |
| 2007/0185197 A1 | 8/2007 | Fujikura et al. | |
| 2008/0242695 A1 | 10/2008 | Morgan et al. | |
| 2009/0286984 A1 | 11/2009 | Raeppel et al. | |
| 2010/0204246 A1 | 8/2010 | Davies et al. | |
| 2012/0184535 A1 | 7/2012 | Brzozka et al. | |
| 2019/0013903 A1 | 1/2019 | Zhang et al. | |
| 2019/0183903 A1 | 6/2019 | Kane, Jr. et al. | |
| 2020/0048222 A1 | 2/2020 | Lieberman et al. | |
| 2021/0169894 A1 | 6/2021 | Kane, Jr. et al. | |

FOREIGN PATENT DOCUMENTS

| | | |
|---|---|---|
| EP | 186190 A2 | 7/1986 |
| JP | S60158180 | 8/1985 |
| JP | 2006273879 A | 10/2006 |
| JP | 6117569 | 4/2017 |
| WO | WO-9901454 A1 | 1/1999 |
| WO | WO-99000372 A1 | 1/1999 |
| WO | WO-02092575 A1 | 11/2002 |
| WO | WO-2004089951 A1 | 10/2004 |
| WO | WO-2005075478 A1 | 8/2005 |
| WO | WO-2005108384 A1 | 11/2005 |
| WO | WO-2006087530 A1 | 8/2006 |
| WO | WO-2007041863 A1 | 4/2007 |
| WO | WO-2010088518 A2 | 8/2010 |
| WO | WO-2011051452 A1 | 5/2011 |
| WO | WO-2011058139 A1 | 5/2011 |
| WO | WO-2012003576 A1 | 1/2012 |
| WO | WO-2012137089 A1 | 10/2012 |
| WO | WO-2013088256 A1 | 6/2013 |
| WO | WO-2013176970 A1 | 11/2013 |
| WO | WO-2015086509 A1 | 6/2015 |
| WO | WO-2015089139 A1 | 6/2015 |
| WO | WO-2016100677 A2 | 6/2016 |

OTHER PUBLICATIONS

Hameed P. Shahul, et al. "Aminoazabenzimidazoles, a Novel Class of Orally Active Antimalarial Agents," *J. Med. Chem.*, 57(13), pp. 5702-5713 (2014).

Office Action U.S. Appl. No. 16/239,904, "Pharmaceutical Formulations of Tropomyosin Related Kinase (TRK) Inhibitors," dated Jun. 8, 2020.

Arthritis Advisory Committee Meeting Announcement Mar. 12, 2012, Retrieved from the Internet: URL: http:/wwwJdapov/AdvisoryCommittees/Calendarucm286556_pdf.

Bertrand, et al., The Crystal Structures of TrkA and TrkB Suggest Key Regions for Achieving Selective Inhibition, *Journal of Molecular Biology*, vol. 423, No. 3, pp. 439-453 (2012).

Chemical Abstract Registry No. 782462-52-6, indexed in the Registry filed on STN CAS Online Nov. 17, 2004.

Chemical Abstracts Registry No. 215242-13-0, indexed in the Registry file on STN CAS Online Dec. 8, 1998.

Corrected Notice of Allowability for U.S. Appl. No. 14/741,017, "Tropomyosin-Related Kinase (TRK) Inhibitors," dated Dec. 6, 2016.

Final Office Action dated Dec. 19, 2019 for U.S. Appl. No. 16/194,696, "Tropomyosin-Related Kinase (TRK) Inhibitors," (5730. 1000-048).

Final Office Action U.S. Appl. No. 14/741,017, "Tropomyosin-Related Kinase (TRK) Inhibitors," dated May 9, 2016.

Final Office Action U.S. Appl. No. 15/436,195, "Tropomyosin-Related Kinase (TRK) Inhibitors," dated Feb. 20, 2018.

Golub, T.R., et al. "Molecular Classification of Cancer: Class Discovery and Class Prediction by Gene Expression Monitoring," *Science*, vol. 286, Oct. 15, 1999, pp. 531-537 (Year: 1999).

International Preliminary Report on Patentability for International Application No. PCT/US2014/069469, "Tropomyosin-Related Kinase (TRK) Inhibitors," dated Jun. 23, 2016.

International Preliminary Report on Patentability for International Application No. PCT/US2015/066396, "Pharmaceutical Formulations of Tropomyosin-Related Kinase (TRK) Inhibitors," dated Jun. 29, 2017.

International Search Report for International Application No. PCT/US2014/069469, "Tropomyosin-Related Kinase (TRK) Inhibitors," dated Feb. 11, 2015.

International Search Report for Internatonal Application No. PCT/US2015/066396, "Pharmaceutical Formulations of Tropomyosin-Related Kinase (TRK) Inhibitors," dated Jun. 21, 2016.

Karaman, et al."A Quantitative Analysis of Kinase Inhibitor Selectivity," *Nature Biotechnology*, vol. 26, No. 1, pp. 127-132 (2008).

Kishida et al., "Benzimidazole derivatives" Chemical Abstract 104: 186419, 2 pages, 1986.

Lane, et al. "Tanezumab for the Treatment of Pain from Osteoarthritis of the Knee," *The New England Journal of Medicine*, vol. 363, pp. 1521-1531 (2010).

Mizuno et al. "Design, Synthesis and Docking Studies of Novel Benzimidazoles for the Treatmentof Metabolic Syndrome," *J. Med. Chem.*, vol. 53, pp. 1076-1085 (2010).

Nicol, G.D., et al. "Unraveling the story of NGF-Mediated Sensitization of Nociceptive Sensory Neurons. ON or OFF the Trks?," *Molecular Interventions*, vol. 7(1), pp. 26-41 (2007).

Notice of Allowance for U.S. Appl. No. 14/564,773, "Tropomyosin-Related Kinase (TRK) Inhibitors," dated Feb. 9, 2015.

Notice of Allowance for U.S. Appl. No. 14/628,876, "Tropomyosin-Related Kinase (TRK) Inhibitors," dated Jun. 29, 2015.

Notice of Allowance for U.S. Appl. No. 14/741,017, "Tropomyosin-Related Kinase (TRK) Inhibitors," dated Nov. 18, 2016.

Notice of Allowance for U.S. Appl. No. 15/436,195, "Tropomyosin-Related Kinase (TRK) Inhibitors," dated Aug. 8, 2018.

Notice of Allowance for U.S. Appl. No. 15/536,544, "Tropomyosin-Related Kinase (TRK) Inhibitors," dated Oct. 4, 2018.

(56) References Cited

OTHER PUBLICATIONS

Office Action dated May 6, 2019 for U.S. Appl. No. 16/194,696, "Tropomyosin-Related Kinase (TRK) Inhibitors" (5730. 1000-048).
Office Action for U.S. Appl. No. 14/628,876, "Tropomyosin-Related Kinase (TRK) Inhibitors," dated Apr. 24, 2015.
Office Action for U.S. Appl. No. 14/741,017, "Tropomyosin-Related Kinase (TRK) Inhibitors," dated Mar. 25, 2016.
Office Action for U.S. Appl. No. 15/436,195, "Tropomyosin-Related Kinase (TRK) Inhibitors," dated Jul. 27, 2017.
Office Action for U.S. Appl. No. 16/194,696, "Tropomyosin-Related Kinase (TRK) Inhibitors," dated Mar. 27, 2020 (5730. 1000-048).
Supplemental Notice of Allowability for U.S. Appl. No. 14/564,773, "Tropomyosin-Related Kinase (TRK) Inhibitors," dated Mar. 10, 2015.
Written Opinion for International Application No. PCT/US2014/069469, "Tropomyosin-Related Kinase (TRK) Inhibitors," dated Feb. 11, 2015.
Written Opinion for International Application No. PCT/US2015/066396, "Pharmaceutical Formulations of Tropomyosin-Related Kinase (TRK) Inhibitors," dated Jun. 21, 2016.
Yadav et al. *Indian J. Pharm Sci.*, 2009;7(4):359-370, (Year: 2009).
Caira, M.R. (1998). Crystalline Polymorphism of Organic Compounds. In: , et al. Design of Organic Solids. Topics in Current Chemistry, vol. 198. Springer, Berlin, Heidelberg. (Abstract only).

\* cited by examiner

—— represents the EC$_{50}$ value (cell based) of 3-(3-methoxy-4-((4-methoxybenzyl)oxy)benzyl)-6-(1-methyl-1H-pyrazol-4-yl)-3H-imidazo[4,5-b]pyridin-2-amine of 1.4 ng/mL)

PHARMACEUTICAL FORMULATIONS OF TROPOMYOSIN RELATED KINASE (TRK) INHIBITORS

CROSS REFERENCE TO RELATED APPLICATIONS

This application is a continuation of U.S. application Ser. No. 16/239,904, filed Jan. 4, 2019, which is a continuation of U.S. application Ser. No. 15/536,544, filed Jun. 15, 2017, now U.S. Pat. No. 10,219,998, which is a 371 National Phase Entry application of International Application No. PCT/US2015/66396, filed Dec. 17, 2015, which claims the benefit of and priority to U.S. Provisional Application 62/093,801, filed Dec. 18, 2014; all of which are hereby incorporated by reference in their entirety.

BACKGROUND OF THE INVENTION

Field of the Invention

This invention relates to pharmaceutical formulations of 3-(3-methoxy-4-((4-methoxybenzyl)oxy)benzyl)-6-(1-methyl-1H-pyrazol-4-yl)-3H-imidazo[4,5-b]pyridin-2-amine, a tropomyosin-related kinase inhibitor ("Trk inhibitor"), and a monohydrate form of 3-(3-methoxy-4-((4-methoxybenzyl)oxy)benzyl)-6-(1-methyl-1H-pyrazol-4-yl)-3H-imidazo[4,5-b]pyridin-2-amine-3-(3-methoxy-4-((4-methoxybenzyl)oxy)benzyl)-6-(1-methyl-1H-pyrazol-4-yl)-3H-imidazo[4,5-b]pyridin-2-amine monohydrate. The monohydrate form has desirable properties which facilitate the preparation of 3-(3-methoxy-4-((4-methoxybenzyl)oxy)benzyl)-6-(1-methyl-1H-pyrazol-4-yl)-3H-imidazo[4,5-b]pyridin-2-amine into pharmaceutical formulations.

The Trk inhibitor microcrystalline solution pharmaceutical formulations comprise 3-(3-methoxy-4-((4-methoxybenzyl)oxy)benzyl)-6-(1-methyl-1H-pyrazol-4-yl)-3H-imidazo[4,5-b]pyridin-2-amine in its monohydrate form, which shows improved characteristics over the anhydrate form.

The instant invention also relates to extended release pharmaceutical formulations of the Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine, comprising 3-(3-methoxy-4-((4-methoxybenzyl)oxy)benzyl)-6-(1-methyl-1H-pyrazol-4-yl)-3H-imidazo[4,5-b]pyridin-2-amine-loaded microspheres.

This invention further relates to the use of these pharmaceutical formulations to treat diseases including inflammatory diseases, autoimmune disease, defects of bone metabolism, and cancer, as well as in the treatment of osteoarthritis (OA), pain, post-operative pain, and pain associated with OA.

The Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine and methods of producing the Trk inhibitor are disclosed in International Patent Application Number PCT/US14/69469 and U.S. patent application Ser. No. 14/564,773, each entitled Tropomyosin-Related Kinase (TRK) Inhibitors, which are incorporated herein by reference.

Related Art

Not applicable

BRIEF SUMMARY OF THE INVENTION

A first aspect of the invention relates to a crystalline form of the Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine, wherein the x-ray powder diffraction pattern contains the following 2θ peaks measured using CuK$_\alpha$ radiation: 7.14, 8.89, 10.22, 12.42, 12.73 and 14.31.

A second aspect of the invention relates to pharmaceutical formulations comprising the crystalline form of the Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine, wherein the x-ray powder diffraction pattern contains the following 2θ peaks measured using CuK$_\alpha$ radiation: 7.14, 8.89, 10.22, 12.42, 12.73 and 14.31, and a pharmaceutically acceptable excipient.

A third aspect of the invention relates to the monohydrate form of the Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine.

A fourth aspect of the invention relates to pharmaceutical formulations comprising the monohydrate form of the Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine and a pharmaceutically acceptable excipient.

A fifth aspect of the invention relates to extended release pharmaceutical formulations comprising 3-(3-methoxy-4-((4-methoxybenzyl)oxy)benzyl)-6-(1-methyl-1H-pyrazol-4-yl)-3H-imidazo[4,5-b]pyridin-2-amine-loaded microspheres.

In a sixth aspect, the invention relates to methods of manufacturing a crystalline form of 3-(3-methoxy-4-((4-methoxybenzyl)oxy)benzyl)-6-(1-methyl-1H-pyrazol-4-yl)-3H-imidazo[4,5-b]pyridin-2-amine comprising:
  a. Mixing 3-(3-methoxy-4-((4-methoxybenzyl)oxy)benzyl)-6-(1-methyl-1H-pyrazol-4-yl)-3H-imidazo[4,5-b]pyridin-2-amine with a solvent to form a suspension;
  b. Stirring the suspension;
  c. Collecting the solids in the suspension by filtration; and
  d. Drying the solids.

In a seventh aspect, the invention relates to methods of manufacturing a monohydrate form of 3-(3-methoxy-4-((4-methoxybenzyl)oxy)benzyl)-6-(1-methyl-1H-pyrazol-4-yl)-3H-imidazo[4,5-b]pyridin-2-amine comprising:
  a. Mixing 3-(3-methoxy-4-((4-methoxybenzyl)oxy)benzyl)-6-(1-methyl-1H-pyrazol-4-yl)-3H-imidazo[4,5-b]pyridin-2-amine with a solvent to form a suspension;
  b. Stirring the suspension;
  c. Collecting the solids in the suspension by filtration; and
  d. Drying the solids.

In an eighth aspect, the invention relates to methods of manufacturing 3-(3-methoxy-4-((4-methoxybenzyl)oxy)benzyl)-6-(1-methyl-1H-pyrazol-4-yl)-3H-imidazo[4,5-b]pyridin-2-amine-loaded microcapsules by solvent extraction, comprising:
  a. Dissolving the 3-(3-methoxy-4-((4-methoxybenzyl)oxy)benzyl)-6-(1-methyl-1H-pyrazol-4-yl)-3H-imidazo[4,5-b]pyridin-2-amine in an organic solvent to form a drug solution;
  b. Adding a polymer to the drug solution to form a polymer/3-(3-methoxy-4-((4-methoxybenzyl)oxy)benzyl)-6-(1-methyl-1H-pyrazol-4-yl)-3H-imidazo[4,5-b]pyridin-2-amine solution;
  c. Mixing the polymer/3-(3-methoxy-4-((4-methoxybenzyl)oxy)benzyl)-6-(1-methyl-1H-pyrazol-4-yl)-3H-imidazo[4,5-b]pyridin-2-amine solution into an aqueous solution to form an emulsion;
  d. Adding deionized water to the emulsion;
  e. Forming microspheres from the emulsion by solvent extraction; and
  f. Sieving the resulting microspheres using a surfactant solution.

And in a ninth aspect, the invention relates to methods of manufacturing 3-(3-methoxy-4-((4-methoxybenzyl)oxy)

benzyl)-6-(1-methyl-1H-pyrazol-4-yl)-3H-imidazo[4,5-b]pyridin-2-amine-loaded microcapsules by solvent extraction, comprising:
  a. Dispersing the 3-(3-methoxy-4-((4-methoxybenzyl)oxy)benzyl)-6-(1-methyl-1H-pyrazol-4-yl)-3H-imidazo[4,5-b]pyridin-2-amine in an organic solvent to form a drug suspension;
  b. Adding a polymer to the drug suspension to form a polymer/3-(3-methoxy-4-((4-methoxybenzyl)oxy)benzyl)-6-(1-methyl-1H-pyrazol-4-yl)-3H-imidazo[4,5-b]pyridin-2-amine dispersion;
  c. Mixing the polymer/3-(3-methoxy-4-((4-methoxybenzyl)oxy)benzyl)-6-(1-methyl-1H-pyrazol-4-yl)-3H-imidazo[4,5-b]pyridin-2-amine dispersion with an aqueous solution to form an emulsion;
  d. Adding deionized water to the emulsion;
  e. Forming microspheres from the emulsion by solvent extraction; and
  f. Sieving the resulting microspheres using a surfactant solution.

In an eleventh aspect, the invention relates to methods of manufacturing 3-(3-methoxy-4-((4-methoxybenzyl)oxy)benzyl)-6-(1-methyl-1H-pyrazol-4-yl)-3H-imidazo[4,5-b]pyridin-2-amine-loaded microcapsules by spray drying, comprising:
  a. Dissolving the 3-(3-methoxy-4-((4-methoxybenzyl)oxy)benzyl)-6-(1-methyl-1H-pyrazol-4-yl)-3H-imidazo[4,5-b]pyridin-2-amine in an organic solvent to form a drug solution;
  b. Adding a polymer to the drug solution to form a polymer/3-(3-methoxy-4-((4-methoxybenzyl)oxy)benzyl)-6-(1-methyl-1H-pyrazol-4-yl)-3H-imidazo[4,5-b]pyridin-2-amine solution; and
  c. Pumping the polymer/3-(3-methoxy-4-((4-methoxybenzyl)oxy)benzyl)-6-(1-methyl-1H-pyrazol-4-yl)-3H-imidazo[4,5-b]pyridin-2-amine solution through a sprayer into a dryer to form a spherical particle.

In a twelfth aspect, the invention relates to methods of manufacturing 3-(3-methoxy-4-((4-methoxybenzyl)oxy)benzyl)-6-(1-methyl-1H-pyrazol-4-yl)-3H-imidazo[4,5-b]pyridin-2-amine-loaded microcapsules by spray drying, comprising:
  a. Dispersing the 3-(3-methoxy-4-((4-methoxybenzyl)oxy)benzyl)-6-(1-methyl-1H-pyrazol-4-yl)-3H-imidazo[4,5-b]pyridin-2-amine in an organic solvent to form a drug suspension;
  b. Adding a polymer to the drug suspension to form a polymer/3-(3-methoxy-4-((4-methoxybenzyl)oxy)benzyl)-6-(1-methyl-1H-pyrazol-4-yl)-3H-imidazo[4,5-b]pyridin-2-amine dispersion; and
  c. Pumping the polymer/3-(3-methoxy-4-((4-methoxybenzyl)oxy)benzyl)-6-(1-methyl-1H-pyrazol-4-yl)-3H-imidazo[4,5-b]pyridin-2-amine dispersion through a sprayer into a dryer to form a spherical particle.

BRIEF DESCRIPTION OF THE SEVERAL VIEWS OF THE DRAWING(S)

FIG. 1: X-Ray Powder Diffraction (XRPD) of the Monohydrate Form of 3-(3-methoxy-4-((4-methoxybenzyl)oxy)benzyl)-6-(1-methyl-1H-pyrazol-4-yl)-3H-imidazo[4,5-b]pyridin-2-amine, 4-40°2θ. The XRPD of the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine shows unique peaks at 7.14, 8.89, 10.22, 12.42, 12.73 and 14.31 2θ peaks measured using $CuK_\alpha$.

Figure 2:
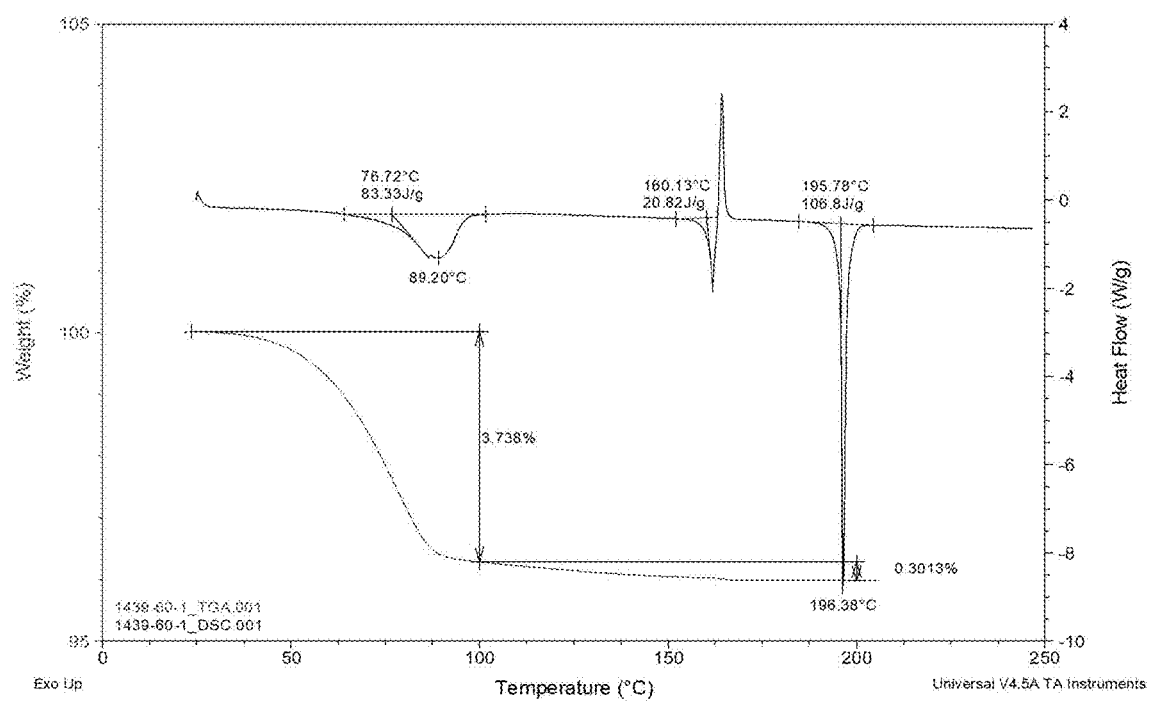

FIG. 2: Differential Scanning Calorimetry (DSC) and Thermal Gravimetric Analysis (TGA) Thermogram of the Monohydrate Form of 3-(3-methoxy-4-((4-methoxybenzyl)oxy)benzyl)-6-(1-methyl-1H-pyrazol-4-yl)-3H-imidazo[4,5-b]pyridin-2-amine, Heated at 10° C./min. The DSC thermogram exhibits three thermal events at 76.72, 160.13, and 195.78° C., the TGA thermogram shows 3.7% weight loss from 25-100° C.

Figure 3:
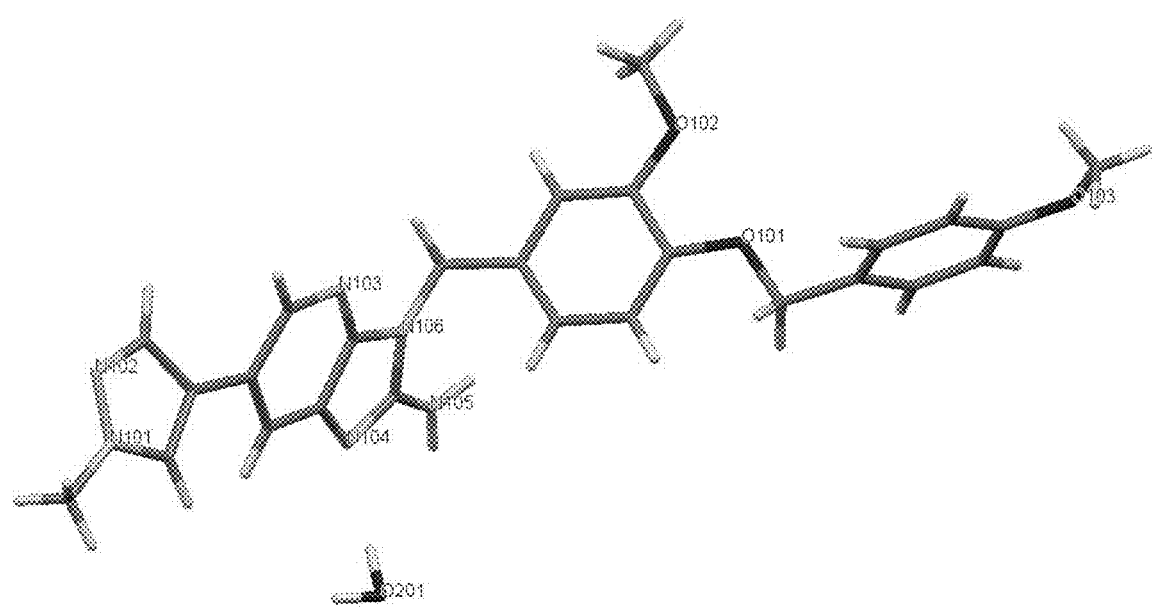

FIG. 3: Crystalline Structure of the Monohydrate Form of 3-(3-methoxy-4-((4-methoxybenzyl)oxy)benzyl)-6-(1-methyl-1H-pyrazol-4-yl)-3H-imidazo[4,5-b]pyridin-2-amine. The crystalline structure of the monohydrate form of the Trk inhibitor is displayed.

Figure 4:
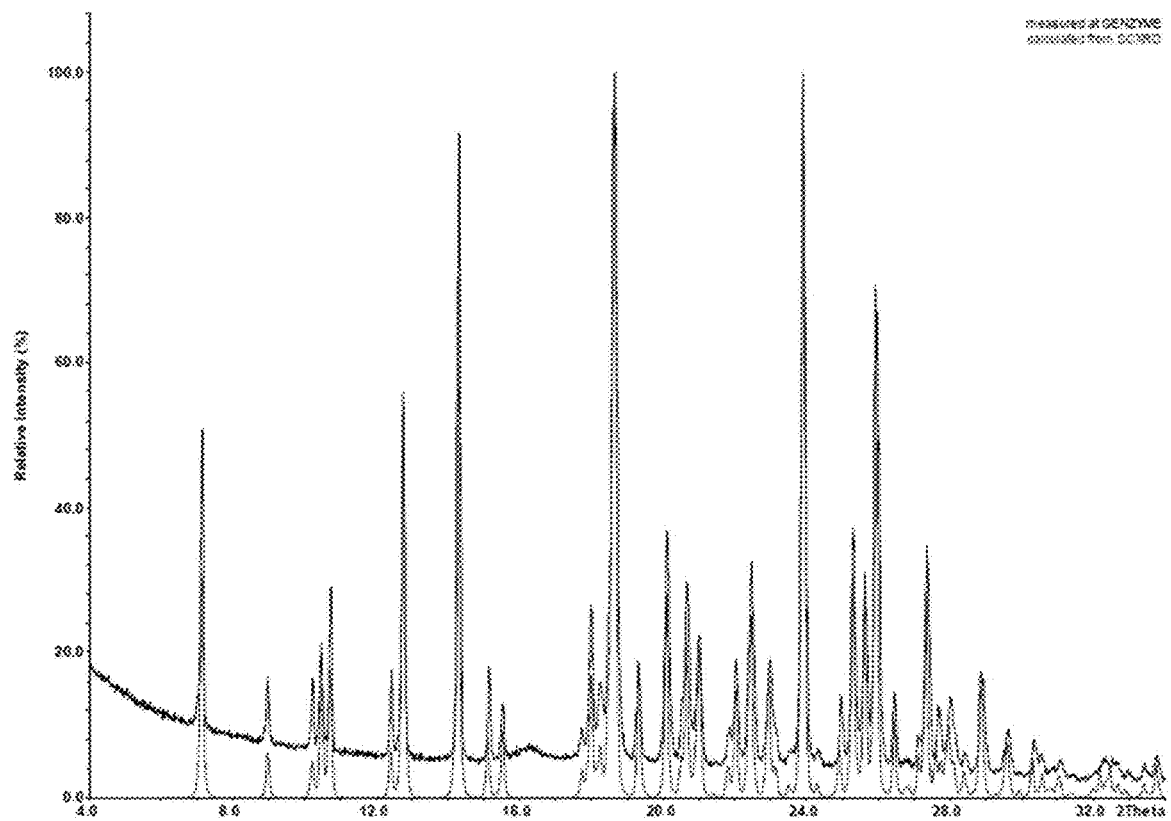

FIG. 4: Overlay of Experimental XRPD Pattern with the XRPD Pattern Calculated from the Single Crystal Structure. This figure displays an overlay of the experimental powder pattern with the one calculated from the single crystal structure. The strong degree of matching suggests that the single crystal structure is indicative of the bulk material.

Figure 5:
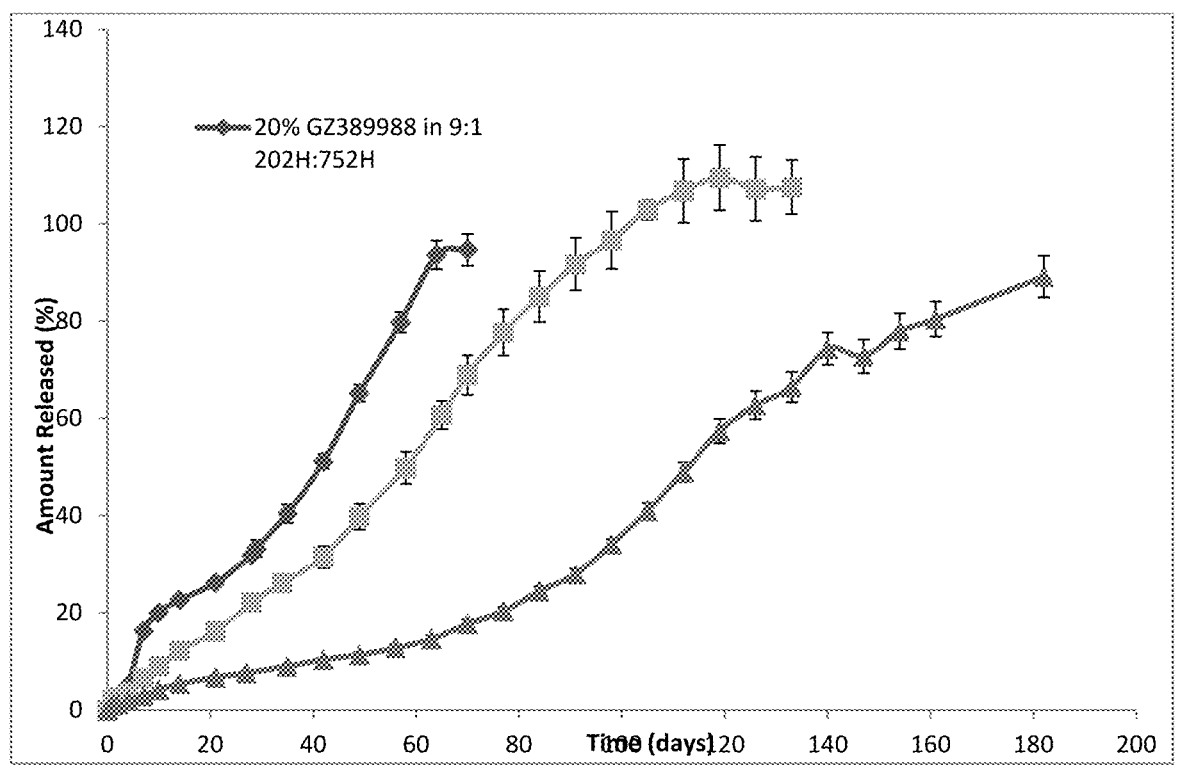

FIG. 5: Effect of API Loading on IVR Profile—12% API/9:1 R202H:752H, 16% API/9:1 R202H:752H and 20% API/9:1 R202H:752H Microspheres. This figure compares the effect of 3-(3-methoxy-4-((4-methoxybenzyl)oxy)benzyl)-6-(1-methyl-1H-pyrazol-4-yl)-3H-imidazo[4,5-b]pyridin-2-amine loading on the in vitro release profile of microspheres of varying composition.

Figure 6:
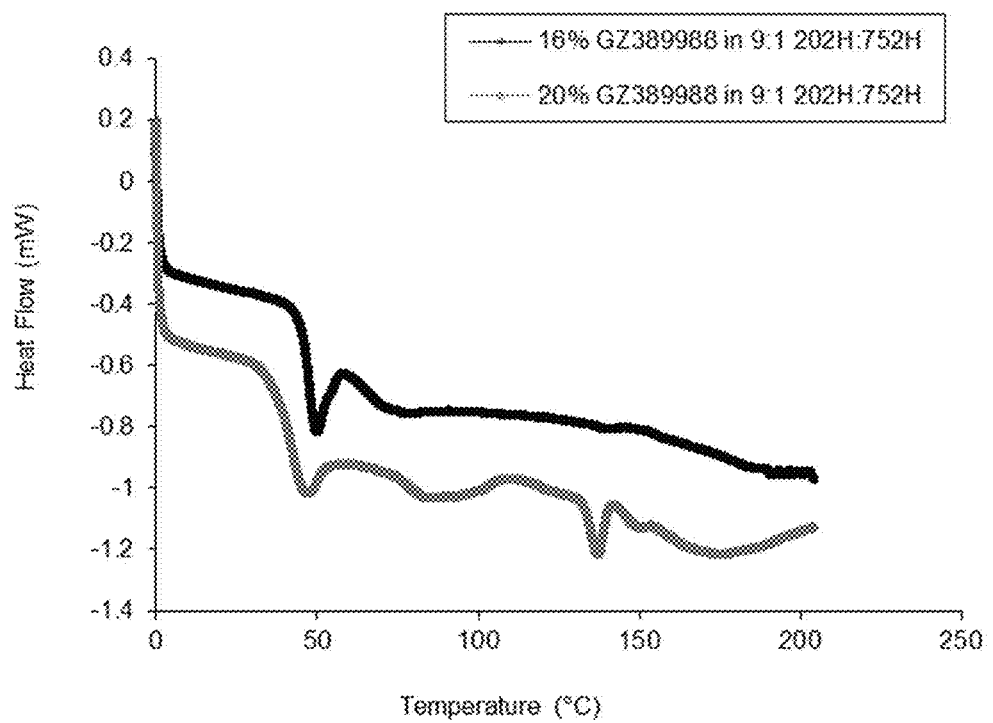

FIG. 6: DSC Thermograms of 16% API/9:1 R202H:752H and 20% API/9:1 R202H:752H Microspheres. The DSC thermogram demonstrates that 20% microspheres show a melting endotherm between 130 150° C. confirming the presence of surface drug crystals.

Figure 7:
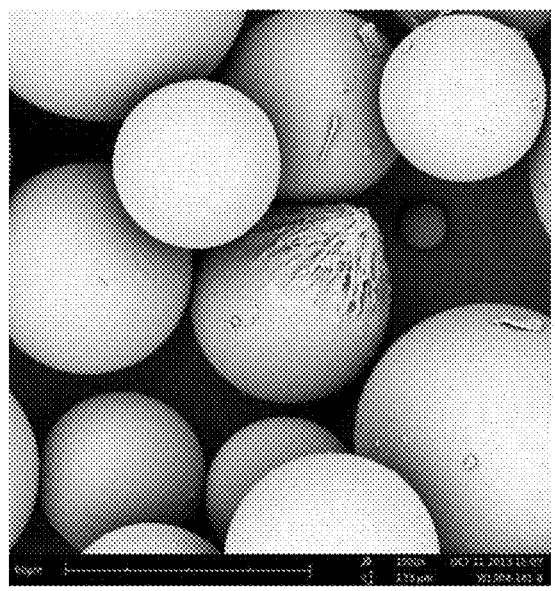

FIG. 7: Scanning Electron Microscopy (SEM) View of 16% API/9:1 R202H:752H Microspheres (1500×). The 16% drug-loaded microspheres show no drug crystals, indicating that the drug is amorphous.

Figure 8:
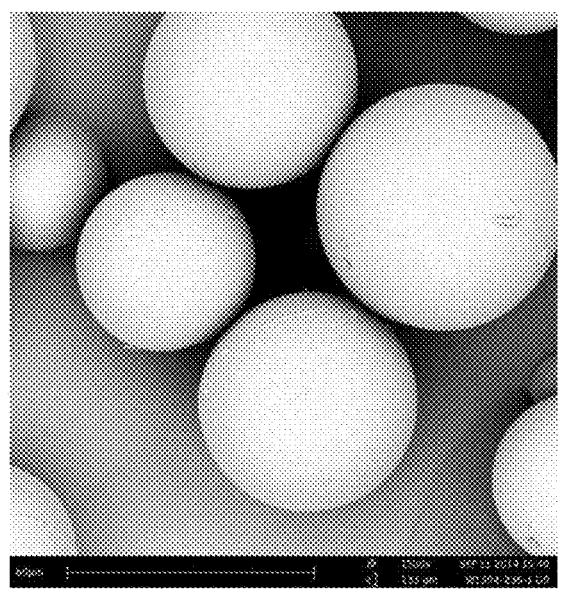

FIG. 8: Scanning Electron Microscopy (SEM) View of 20% API/9:1 R202H:752H Microspheres (1500×). The 20% drug-loaded microspheres show surface drug crystals.

Figure 9:
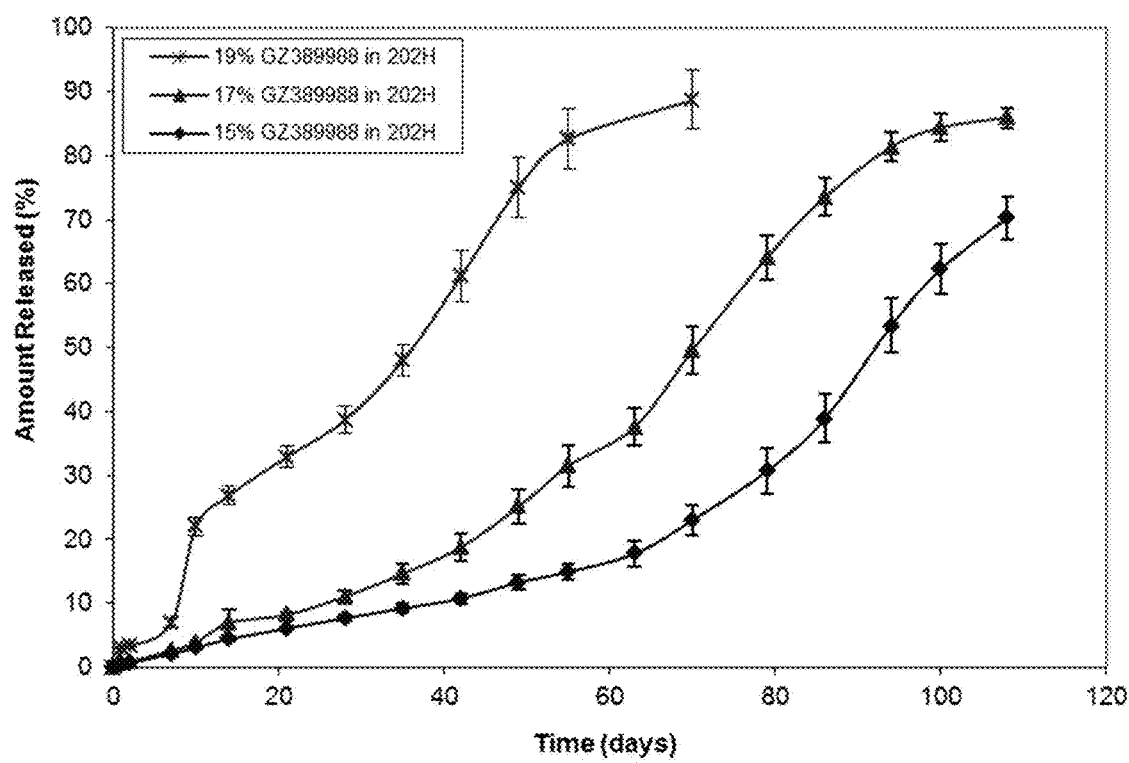

FIG. 9: Effect of API Loading on IVR Profile—15% API/R202H, 17% API/R202H and 19% API/R202H Microspheres. This figure compares the effect of 3-(3-methoxy-4-((4-methoxybenzyl)oxy)benzyl)-6-(1-methyl-1H-pyrazol-4-yl)-3H-imidazo[4,5-b]pyridin-2-amine loading on the in vitro release profile of microspheres of varying composition.

Figure 10:
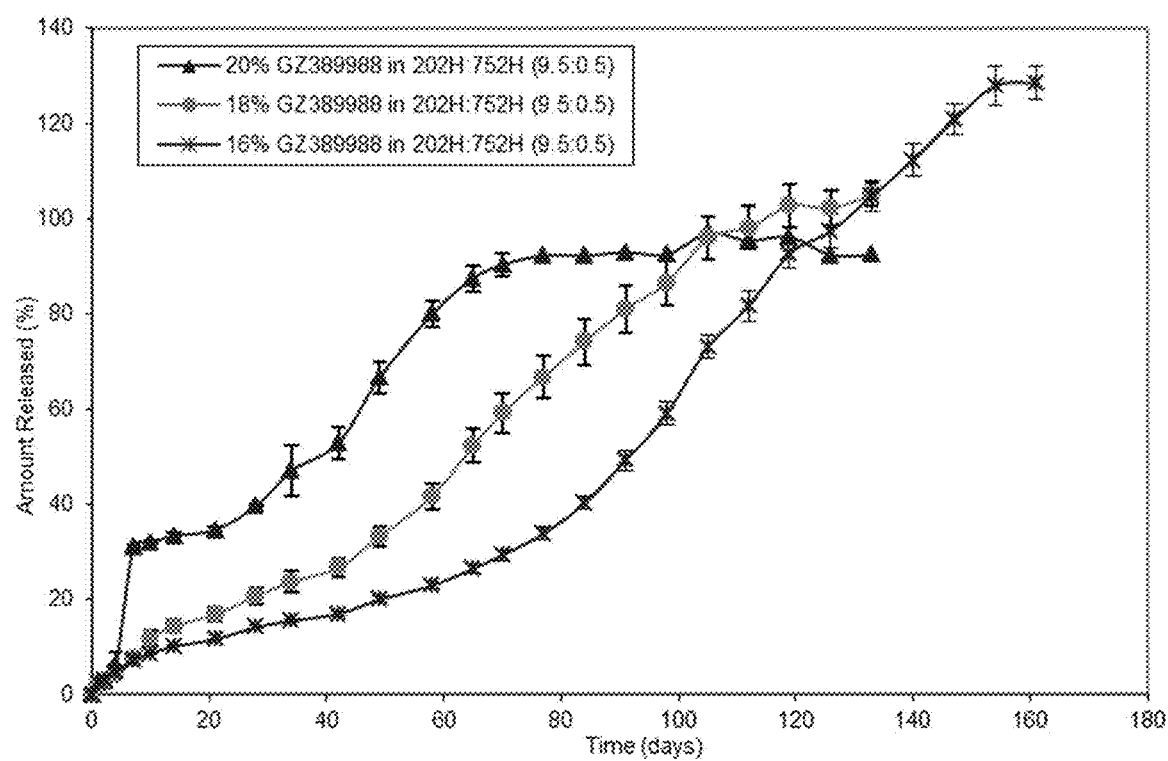

FIG. 10: Effect of API Loading on IVR Profile—16% API/9.5:0.5 R202H:752H, 18% API/9.5:0.5 R202H:752H and 20% API/9.5:0.5 R202H:752H Microspheres. This figure compares the effect of 3-(3-methoxy-4-((4-methoxybenzyl)oxy)benzyl)-6-(1-methyl-1H-pyrazol-4-yl)-3H-imidazo[4,5-b]pyridin-2-amine loading on the in vitro release profile of microspheres of varying composition.

Figure 11:
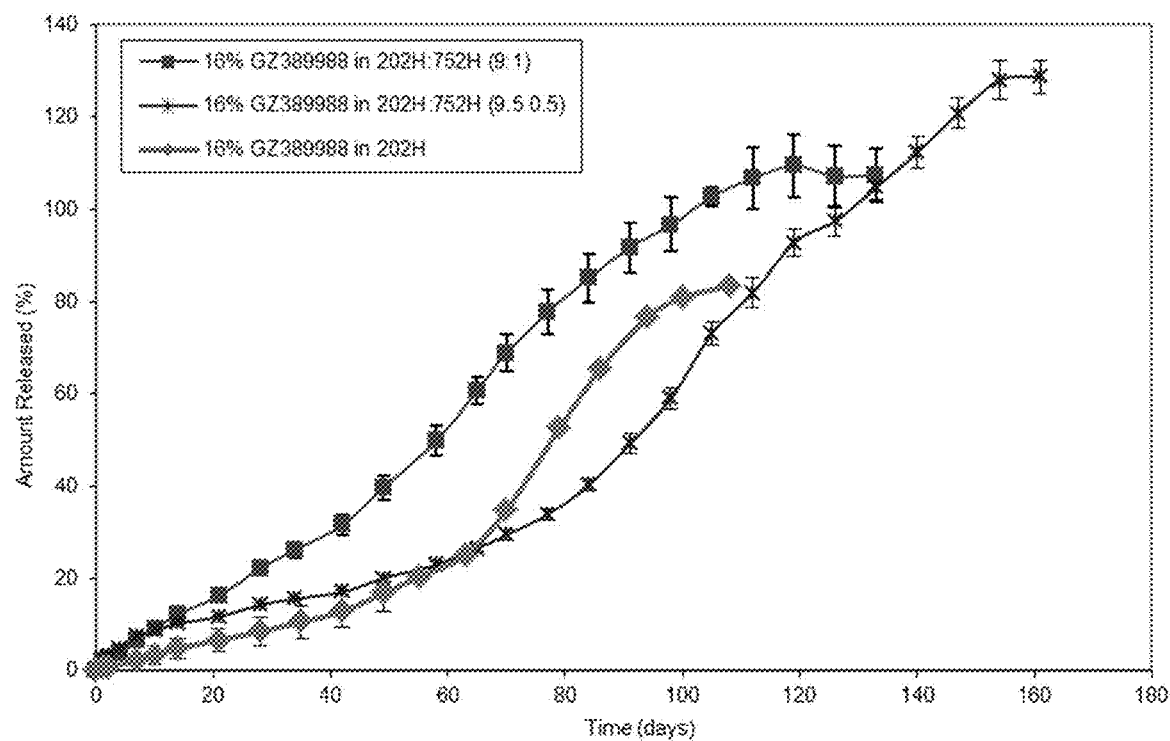

FIG. 11: Effect Polymer Blend on IVR Profile—16% API/R202H, 16% API/9.0:0.5 R202H:RG752H and 16% API/9:1 R202H:RG752H Microspheres. This figure compares the effect of the polymer blend on the in vitro release profile of microspheres of varying composition.

Figure 12:
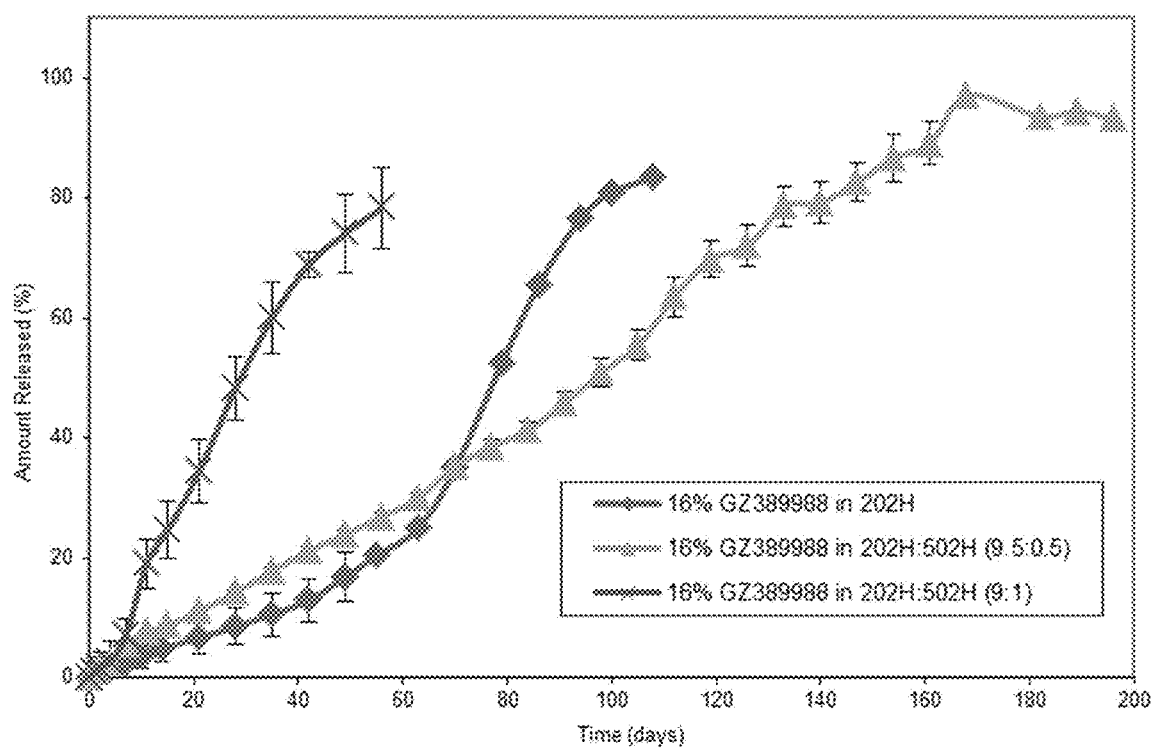

FIG. 12: Effect Polymer Blend on IVR Profile—16% API/R202H, 16% API/9.5:0.5 R202H:RG502H and 16% API/9:1 R202H:RG502H Microspheres. This figure compares the effect of the polymer blend on the in vitro release profile of microspheres of varying composition.

Figure 13:
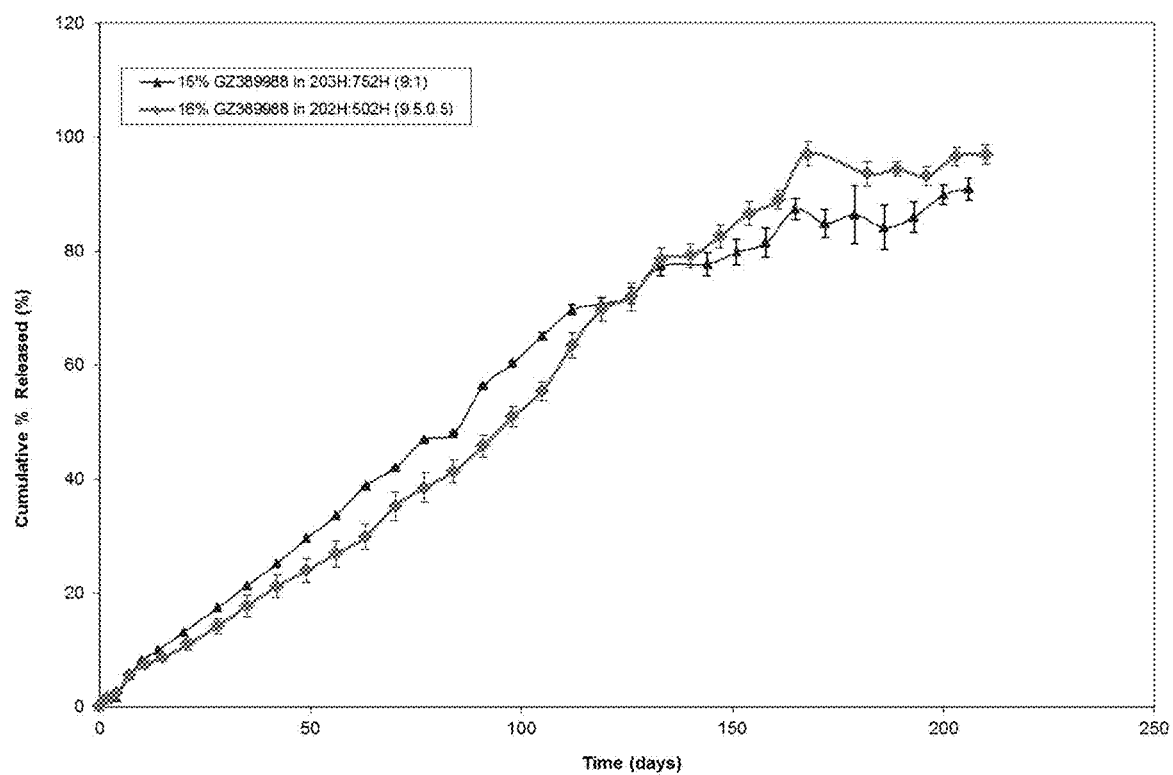

FIG. 13: Formulations Showing Zero-Order IVR Profile for 180 Days—15% API/9:1 R203H:RG752H and 16% API/9.5:0.5 R202H:RG502H Microspheres. Microspheres prepared using 15% 3-(3-methoxy-4-((4-methoxybenzyl)oxy)benzyl)-6-(1-methyl-1H-pyrazol-4-yl)-3H-imidazo[4,5-b]pyridin-2-amine in R203H:752H polymers at a ratio of 9:1 and 16% 3-(3-methoxy-4-((4-methoxybenzyl)oxy)benzyl)-6-(1-methyl-1H-pyrazol-4-yl)-3H-imidazo[4,5-b]pyridin-2-amine in R202H:RG502H polymers at a ratio of 9.5:0.5 exhibited a pseudo zero-order release profile over 6 months.

Figure 14:
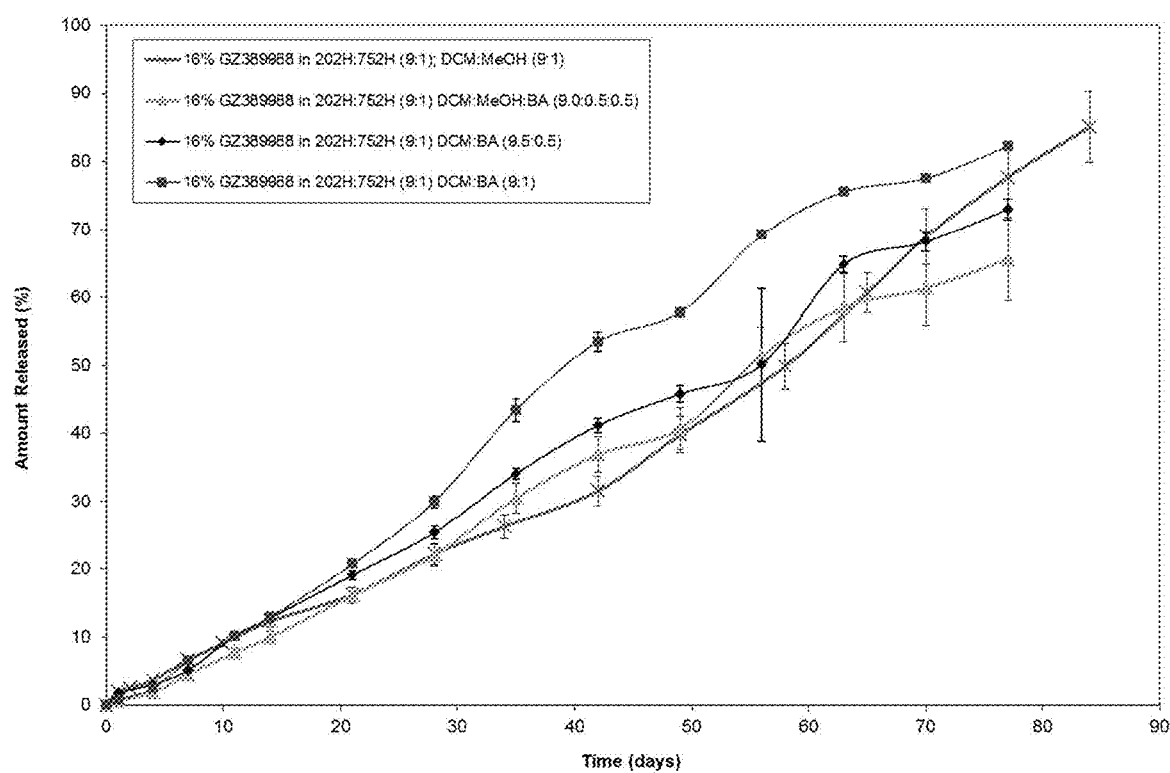

FIG. 14: Effect of Co-Solvent Systems in Preparation on IVR Profile—16% API/9:1 R203H:RG752H Microspheres—9:1 DCM:MeOH, 9:0.5:0.5 DCM:MeOH:BA, 9.5:05 DCM:BA, 9:1 DCM:BA. This figure compares the effect of the co-solvent system used in the preparation of the microspheres on the in vitro release profile of microspheres with 16% drug-loading and a polymer blend of 9:1 R203H:RG752H.

Figure 15:
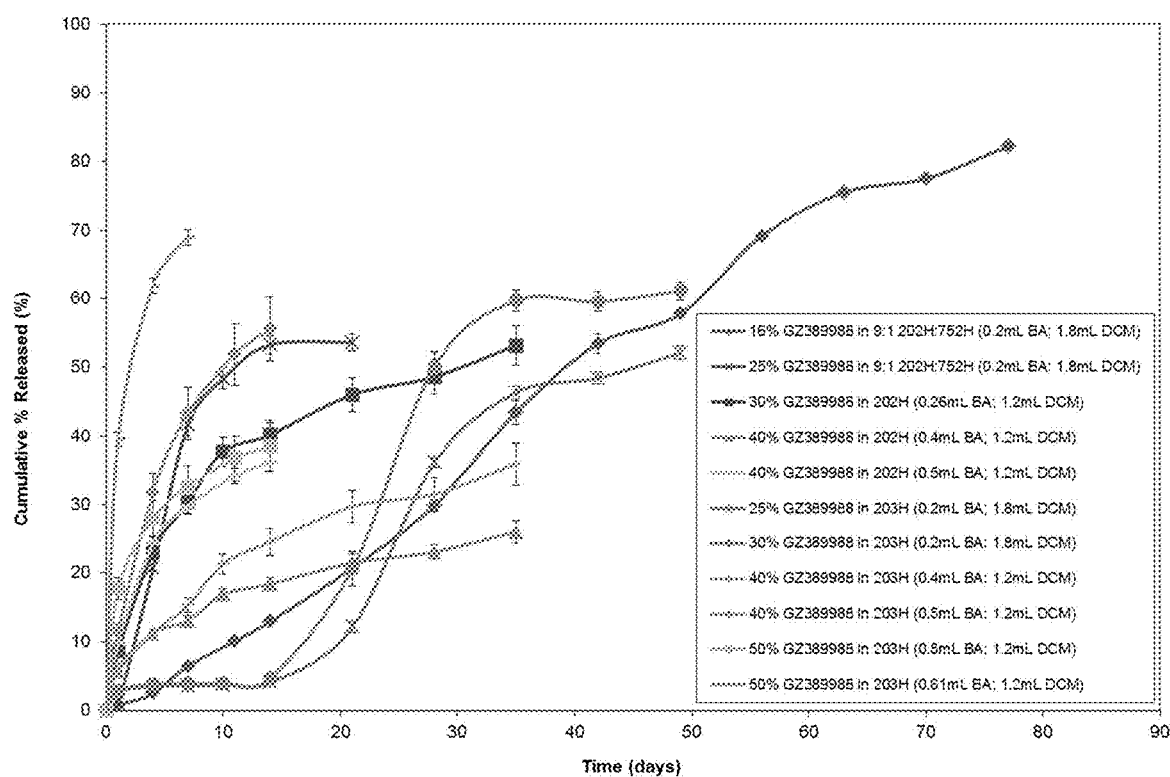

FIG. 15: Effect of DCM:BA Co-Solvent System to Increase API Loading on IVR Profile—16% API/9:1 R202H:RG752H, 25% API/9:1 R202H:RG752H, 30% API/R202H, 40% API/R202H, 25% API/R203H, 30% API/R203H, 40% API/R203H, 50% API/R203H Microspheres. This figure compares the effect of the co-solvent system used in the preparation of the microspheres to increase drug-loading on the in vitro release profile of microspheres varying polymer blends.

Figure 16:
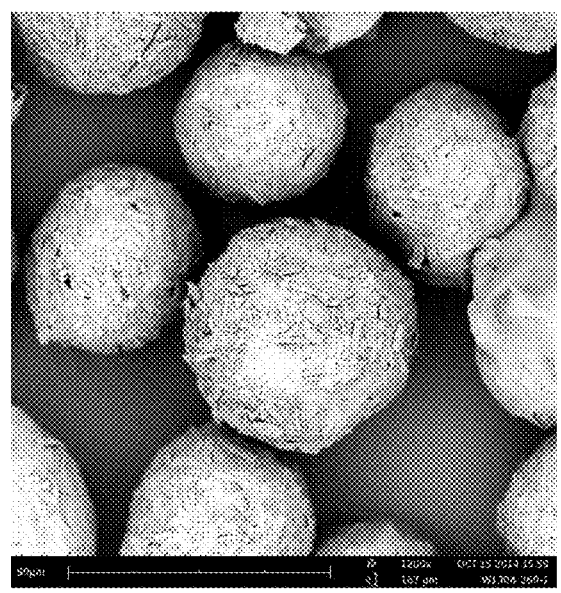

FIG. 16: Scanning Electron Microscopy (SEM) View of Microspheres Prepared with Micronized Suspension Microencapsulation Process (1500×). Microspheres produced by encapsulating a suspension of 3-(3-methoxy-4-((4-methoxybenzyl)oxy)benzyl)-6-(1-methyl-1H-pyrazol-4-yl)-3H-imidazo[4,5-b]pyridin-2-amine were spherical with a rough surface texture due to the presence of drug crystals embedded in the surface.

Figure 17:
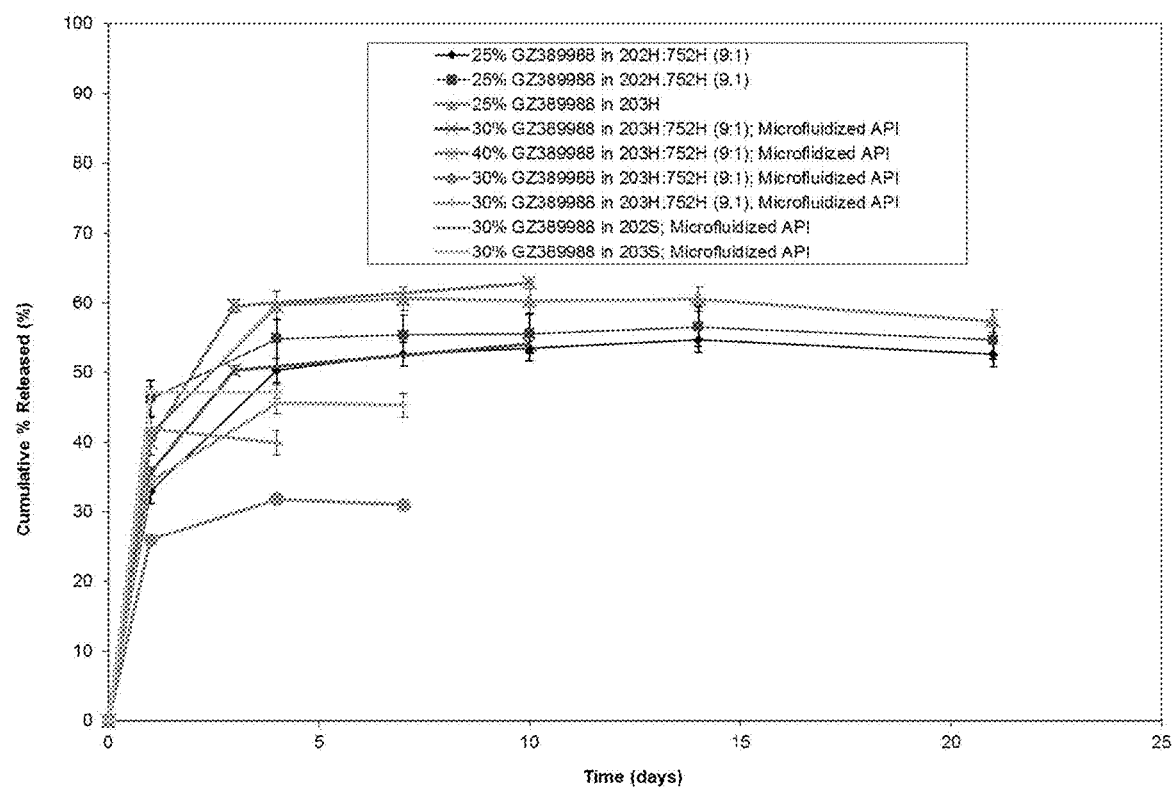

FIG. 17: Effect of Micronized Suspension Microencapsulation Process on IVR Profile—25% API/9:1 R202H:RG752H 39 mL 5% PVA+2.6 mL EA, 25% API/9:1 R202H:RG752H 39 mL 5% PVA+3.25 mL EA, 25% API/R203H 39 mL 5% PVA+2.0 mL EA, 30% Microfluidized API/9:1 R202H:RG752H 39 mL 5% PVA+2.0 mL EA, 40% Microfluidized API/9:1 R202H:RG752H 39 mL 5% PVA+2.0 mL EA, 30% Microfluidized API/9:1 R202H:RG752H 39 mL 5% PVA+2.0 mL EA, 30% Microfluidized API/9:1 R202H:RG752H 39 mL 5% PVA+2.3 mL EA, 30% Microfluidized API/R202S 39 mL 5% PVA+2.0 mL EA, 30% Microfluidized API/R203S 39 mL 5% PVA+2.0 mL Microspheres. This figure compares the micronized suspension microencapsulation process used in the preparation of the microspheres on the in vitro release profile of microspheres with varying drug-loading.

Figure 18:
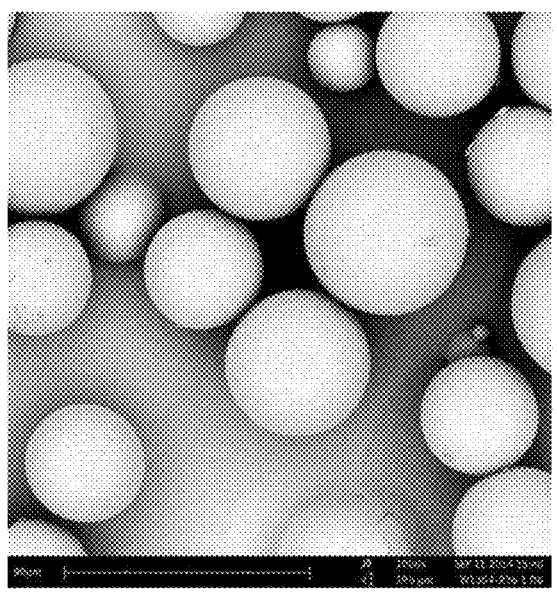

FIG. 18: Scanning Electron Microscopy (SEM) View of 16% API/9:1 R202H:RG752H Microspheres, Solvent Extraction (1000×). Solvent extraction microspheres were spherical with a smooth surface texture.

Figure 19:
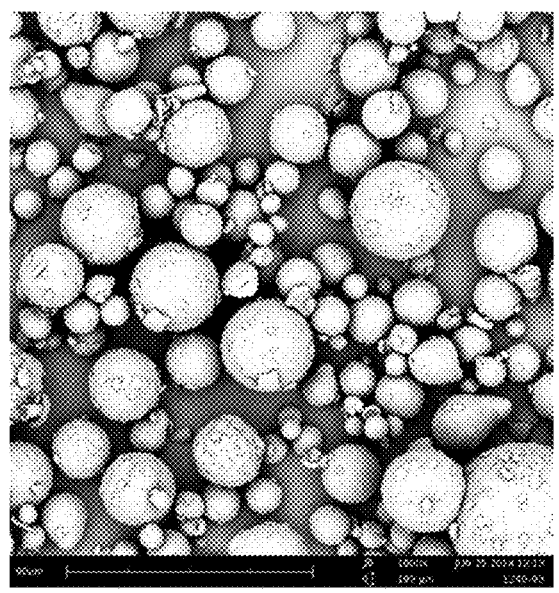

FIG. 19: Scanning Electron Microscopy (SEM) View of 16% API/9:1 R202H:RG752H Microspheres, Spray Drying (1000×). Spray dried microspheres were spherical with some surface texture.

Figure 20:
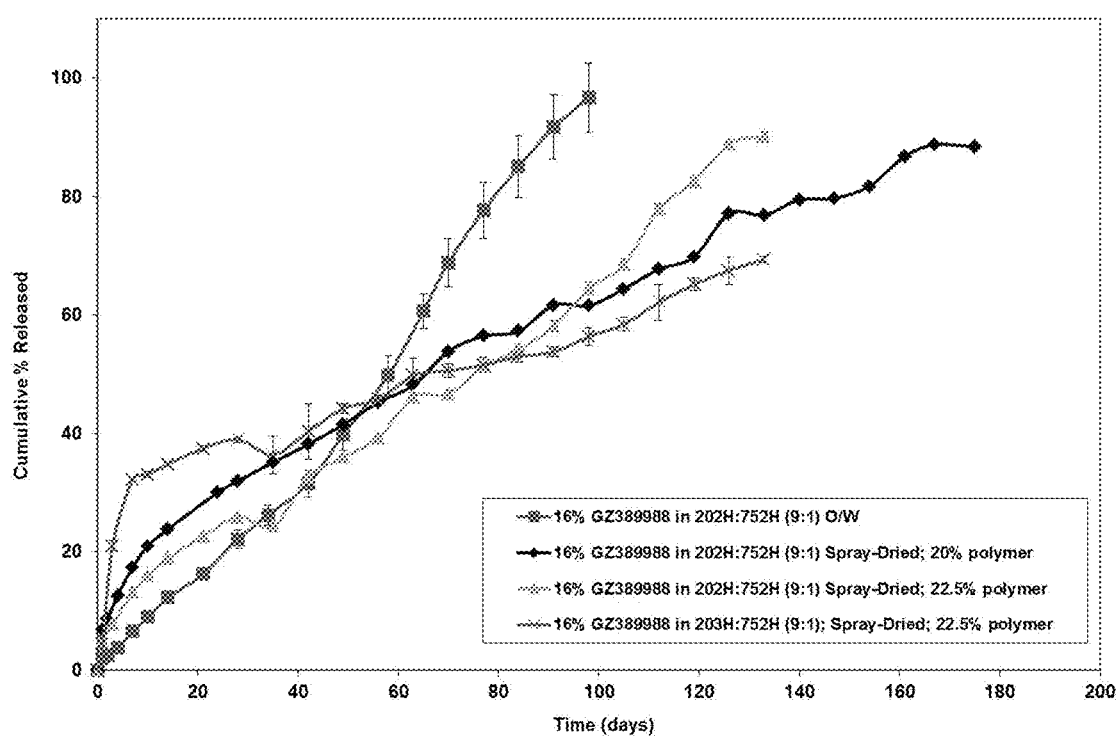

FIG. 20: Effect of Microencapsulation Process on IVR Profile—16% API/9:1 R202H:RG752H Microspheres by Solvent Extraction (OW), 16% API/9:1 R202H:RG752H Microspheres by Spray Drying (20% and 22.5% Polymer) and 16% API/9:1 R203H:RG752H Microspheres by Spray Drying (22.5% Polymer). This figure compares the in vitro release profile of 16% drug-loaded, 9:1 R202H:RG752H microspheres prepared by solvent extraction and spray drying. This shows the effect of the microencapsulation process on the on the in vitro release profile of microspheres of varying formulations.

Figure 21:
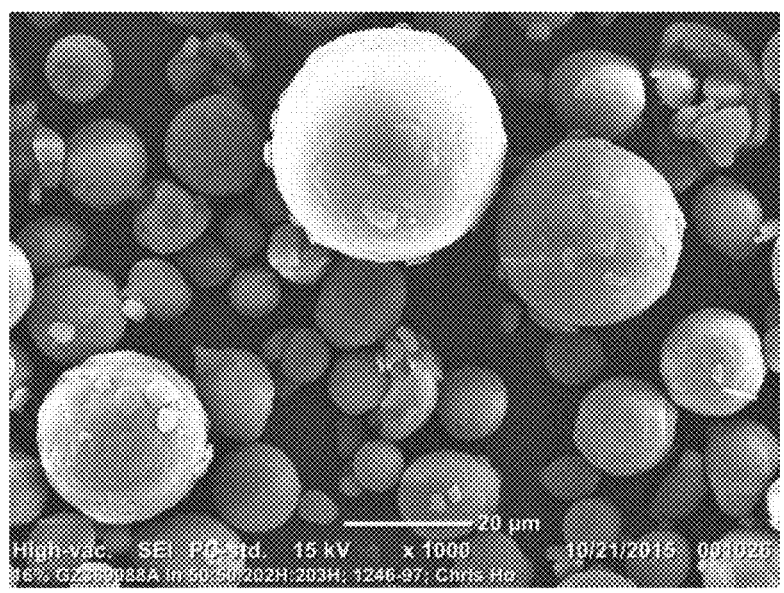

FIG. 21: Scanning Electron Microscopy (SEM) View of 16% API/1:1 R202H:R203H/No Additive Microspheres, Spray Dried (1000×). Spray dried microspheres of 16% API/1:1 R202H:R203H/No Additive are presented.

Figure 22:
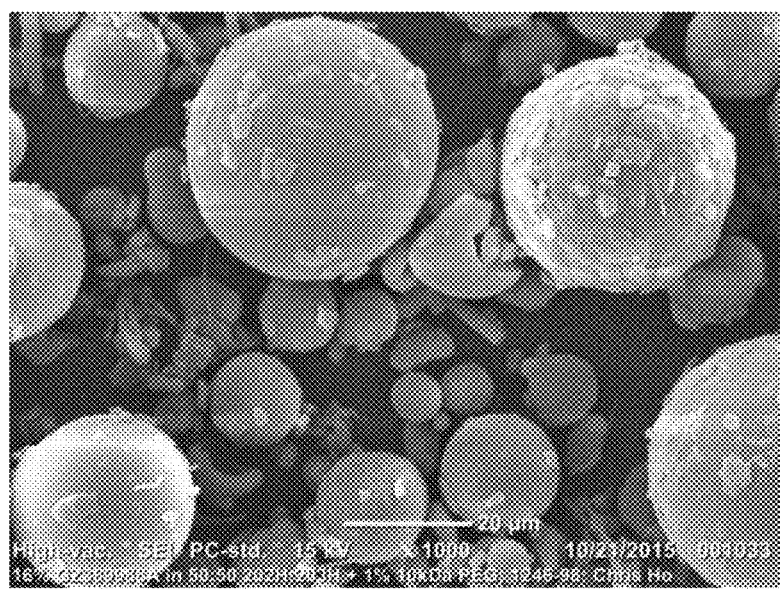

FIG. 22: Scanning Electron Microscopy (SEM) View of 16% API/1:1 R202H:R203H/31.25 mg PEG Microspheres, Spray Dried (1000×). Spray dried microspheres of 16% API/1:1 R202H:R203H/31.25 mg PEG are presented.

Figure 23:
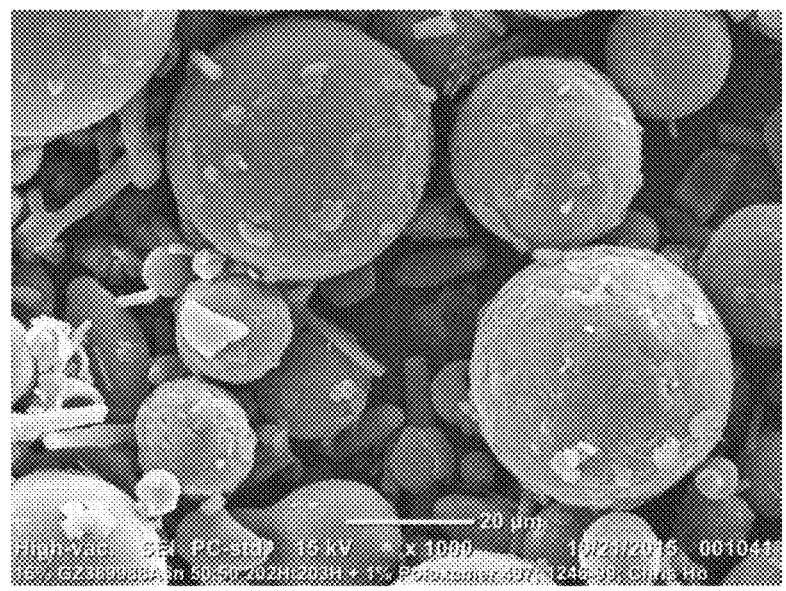

FIG. 23: Scanning Electron Microscopy (SEM) View of 16% API/1:1 R202H:R203H/31.25 mg Poloxamer 407 Microspheres, Spray Dried (1000×). Spray dried microspheres of 16% API/1:1 R202H:R203H/31.25 mg Poloxamer 407 are presented.

Figure 24:
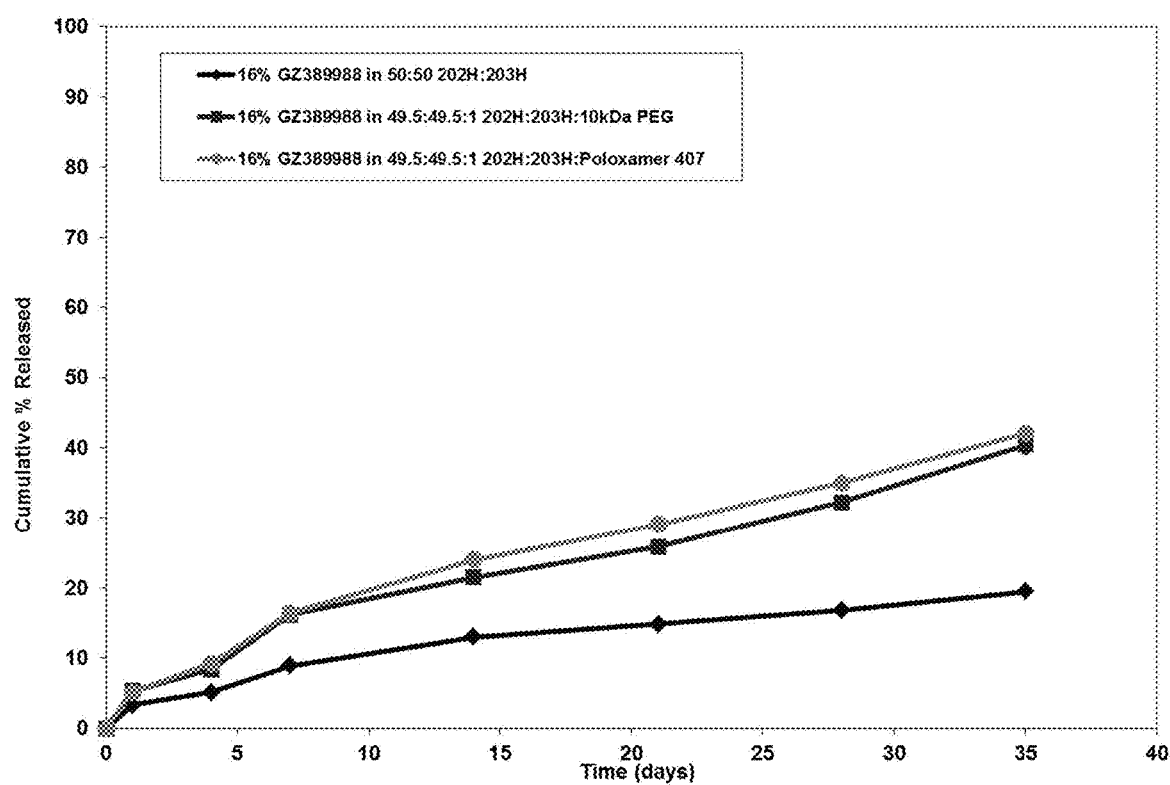

FIG. 24: Effect of % 10 kDa PEG or 1% Poloxamer 407 on IVR Profile—16% API/1:1 R202H:R203H/No Additive, 16% API/1:1 R202H:R203H/31.25 mg PEG, 16% API/1:1 R202H:R203H/31.25 mg Poloxamer 407. This figure compares the in vitro release profile of 16% API/1:1 R202H:R203H/No Additive microspheres, 16% API/1:1 R202H:R203H/31.25 mg PEG microspheres, and 16% API/1:1 R202H:R203H/31.25 mg Poloxamer 407 prepared by spray drying.

Figure 25:
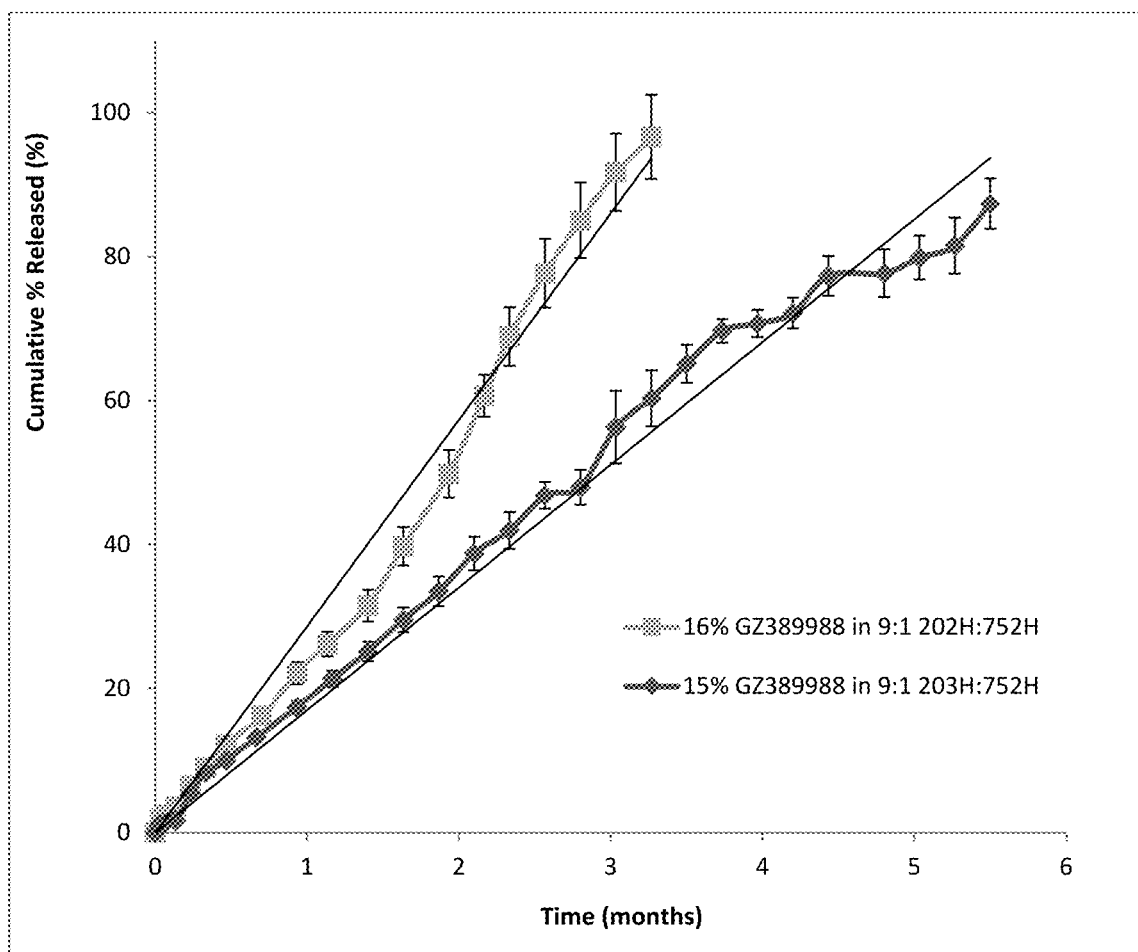

FIG. 25: In vivo (Rat) IVR Profile—16% API/9:1 202H:RG502H and 15% API/9:1 R203H:RG752H Microspheres. This figure shows a near-zero-order release in vivo over approximately 3-4 months and 5-6 months for 16% API/9:1 202:H:RG502H and 15% API/9:1 R203H:RG752H microspheres.

Figure 26:
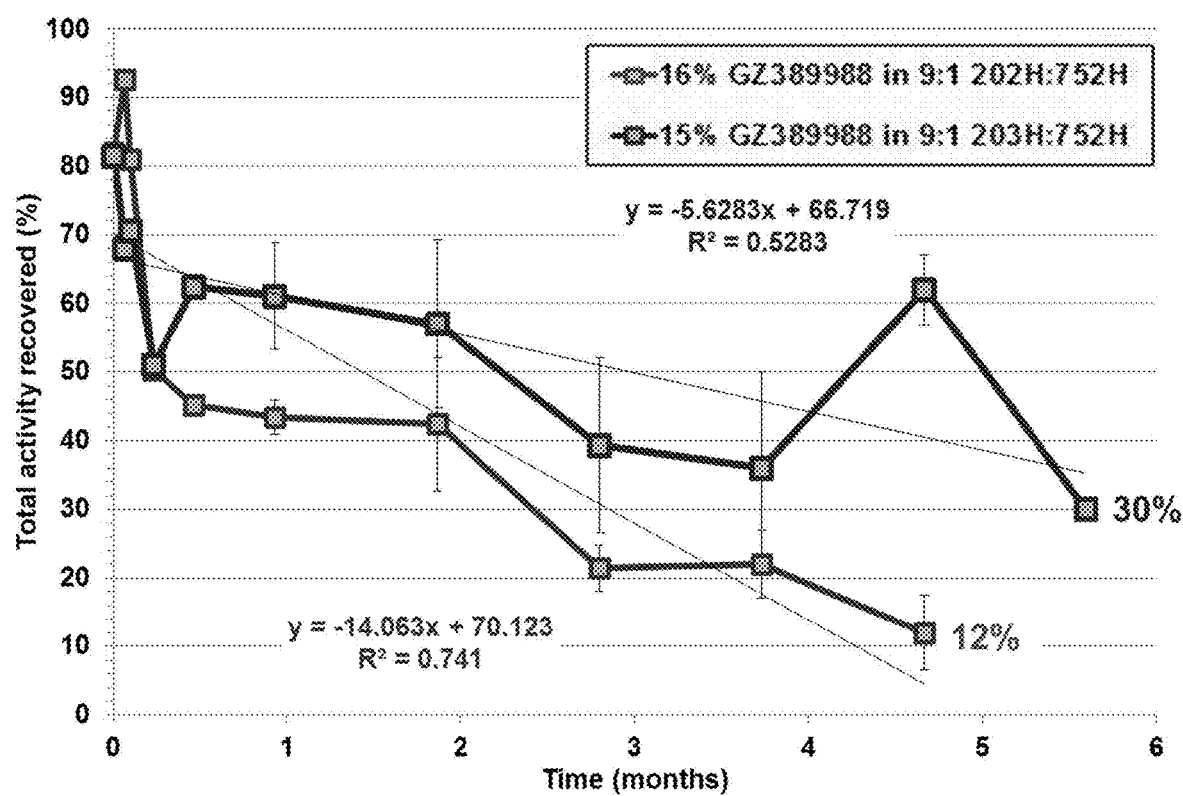

FIG. 26: [$^{14}$C] 3-(3-methoxy-4-((4-methoxybenzyl)oxy)benzyl)-6-(1-methyl-1H-pyrazol-4-yl)-3H-imidazo[4,5-b]pyridin-2-amine Remaining Over Time (Rat Knee Joint)—16% API/9:1 202H:RG502H and 15% API/9:1 203H:RG752H Microspheres. Following intra-articular administration into rat knee joints, for 16% API/9:1 202:H:RG502H and 15% API/9:1 R203H:RG752H microspheres showed drug release over 5 to 6 months; 16% API/9:1 202:H:RG502H showed 12% remaining in the joint after 5 months and 15% API/9:1 R203H:RG752H showed 30% of the drug remaining after 6 months.

Figure 27:
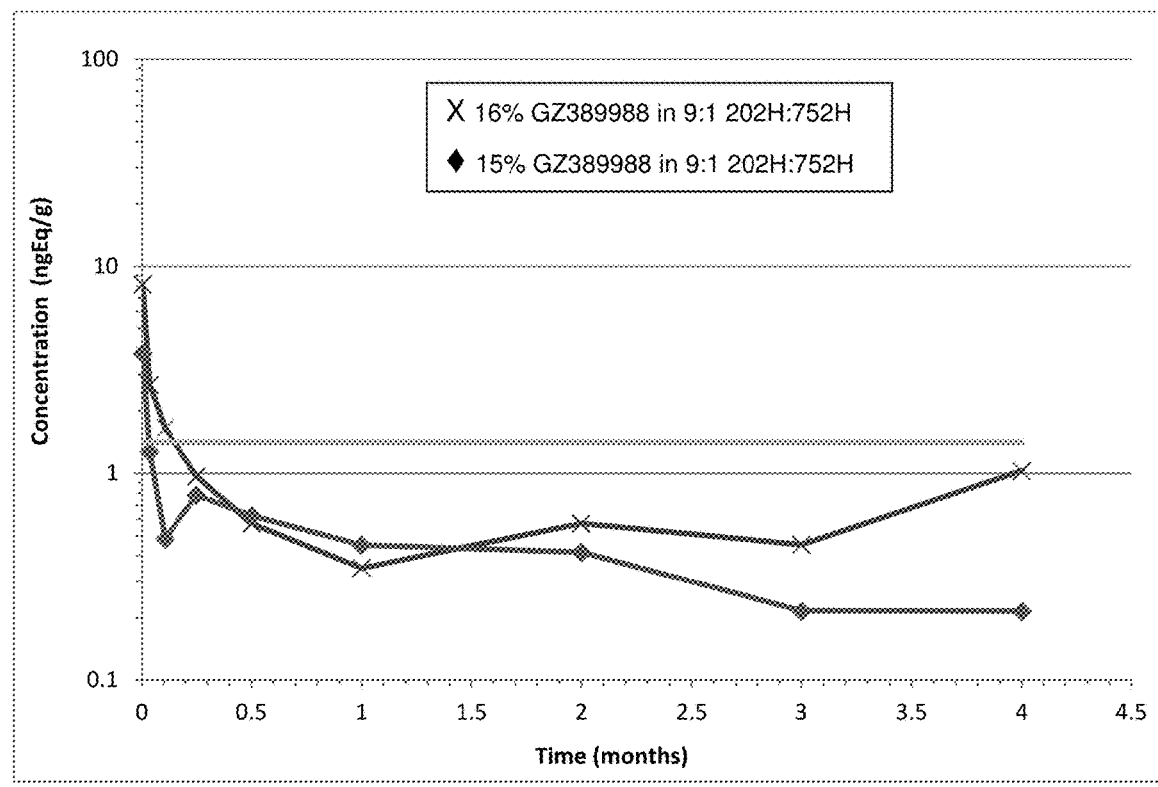

FIG. 27: 3-(3-methoxy-4-((4-methoxybenzyl)oxy)benzyl)-6-(1-methyl-1H-pyrazol-4-yl)-3H-imidazo[4,5-b]pyridin-2-amine Concentration-Time Profiles (Rat Blood)—16% API/9:1 202:H:RG502H and 15% API/9:1 R203H:RG752H Microspheres. This figure shows the drug concentration-time profile in blood following intra-articular administration of 3-(3-methoxy-4-((4-methoxybenzyl)oxy)benzyl)-6-(1-methyl-1H-pyrazol-4-yl)-3H-imidazo[4,5-b]pyridin-2-amine-loaded microspheres.

Figure 28:
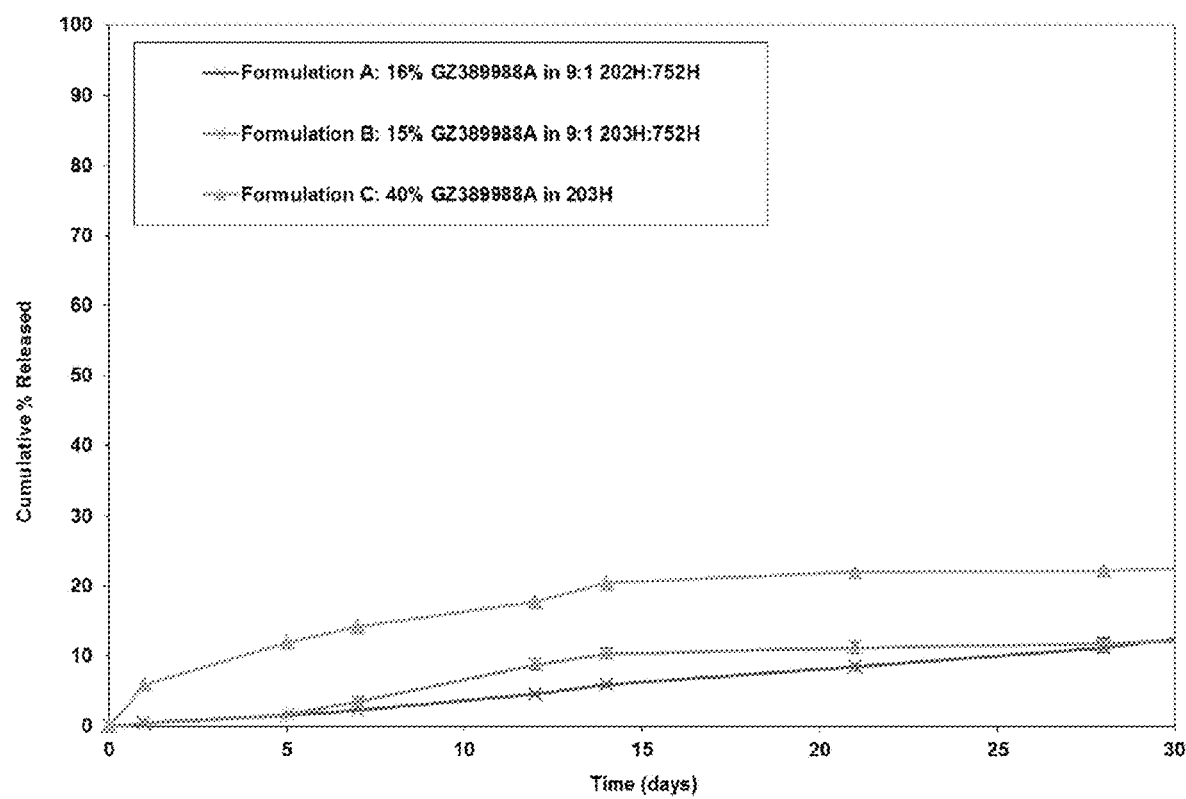

FIG. 28: IVR Profile—16% API/9:1 202:H:RG752H, 15% API/9:1 R203H:RG752H and 40% API/203H Microspheres.

Figure 29:
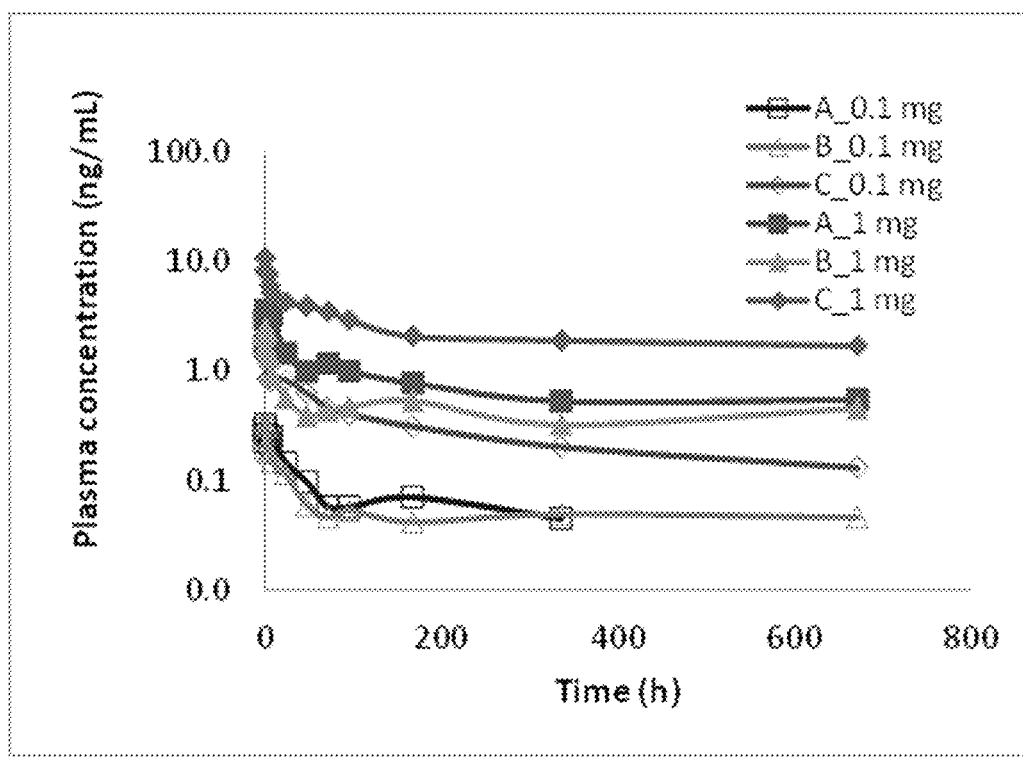

FIG. 29: 3-(3-methoxy-4-((4-methoxybenzyl)oxy)benzyl)-6-(1-methyl-1H-pyrazol-4-yl)-3H-imidazo[4,5-b]pyridin-2-amine Concentration-Time Profiles—16% API/9:1 202:H:RG752H, 15% API/9:1 R203H:RG752H and 40% API/203H Microspheres.

Figure 30:
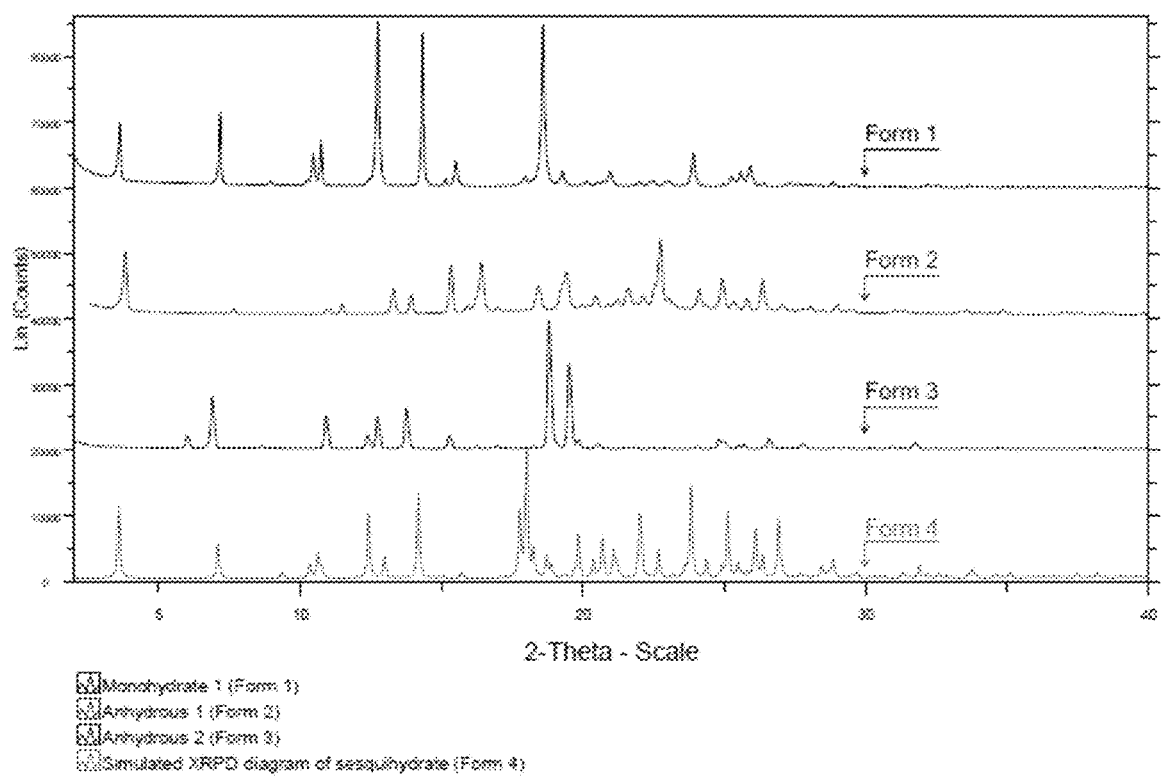

FIG. 30: Measured or Simulated XRPD of Forms 1 to 4 (Anhydrous and Hydrate). The XRPD of the anhydrous and hydrate forms of 3-(3-methoxy-4-((4-methoxybenzyl)oxy)benzyl)-6-(1-methyl-1H-pyrazol-4-yl)-3H-imidazo[4,5-b]pyridin-2-amine are presented.

Figure 31:
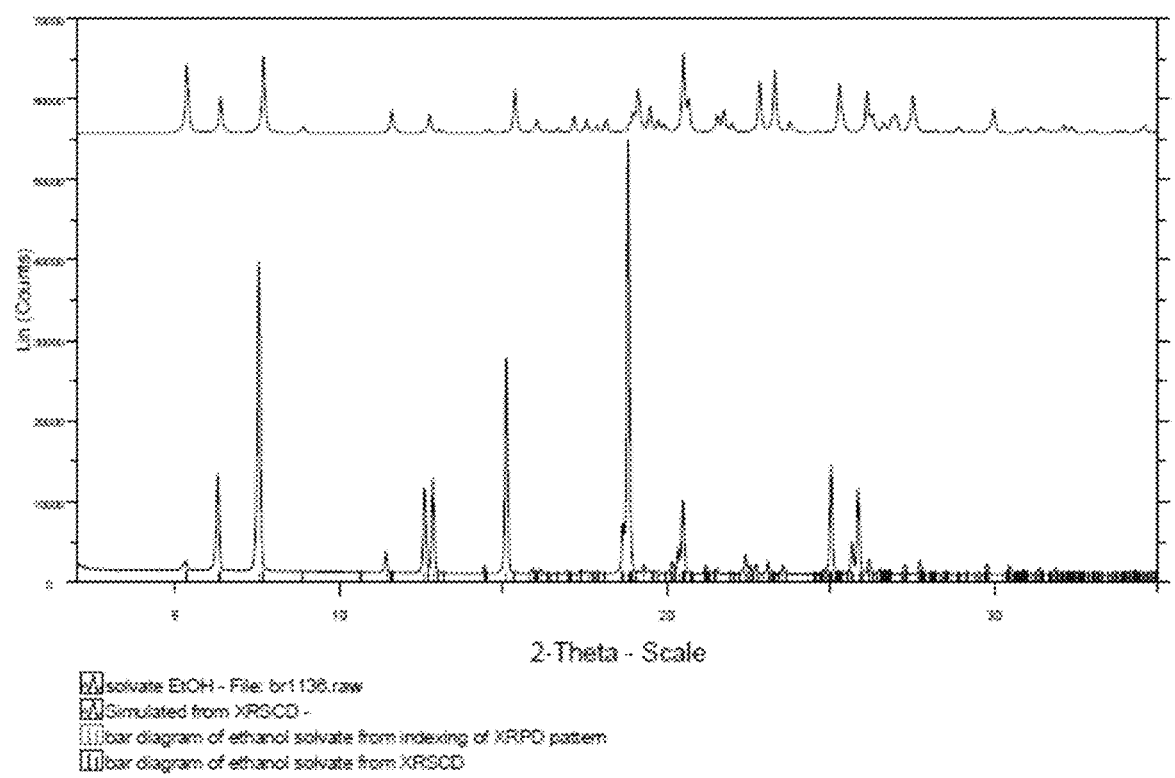

FIG. 31: The XRPD of Form 5 (Ethanol) of 3-(3-methoxy-4-((4-methoxybenzyl)oxy)benzyl)-6-(1-methyl-1H-pyrazol-4-yl)-3H-imidazo[4,5-b]pyridin-2-amine is presented.

Figure 32:
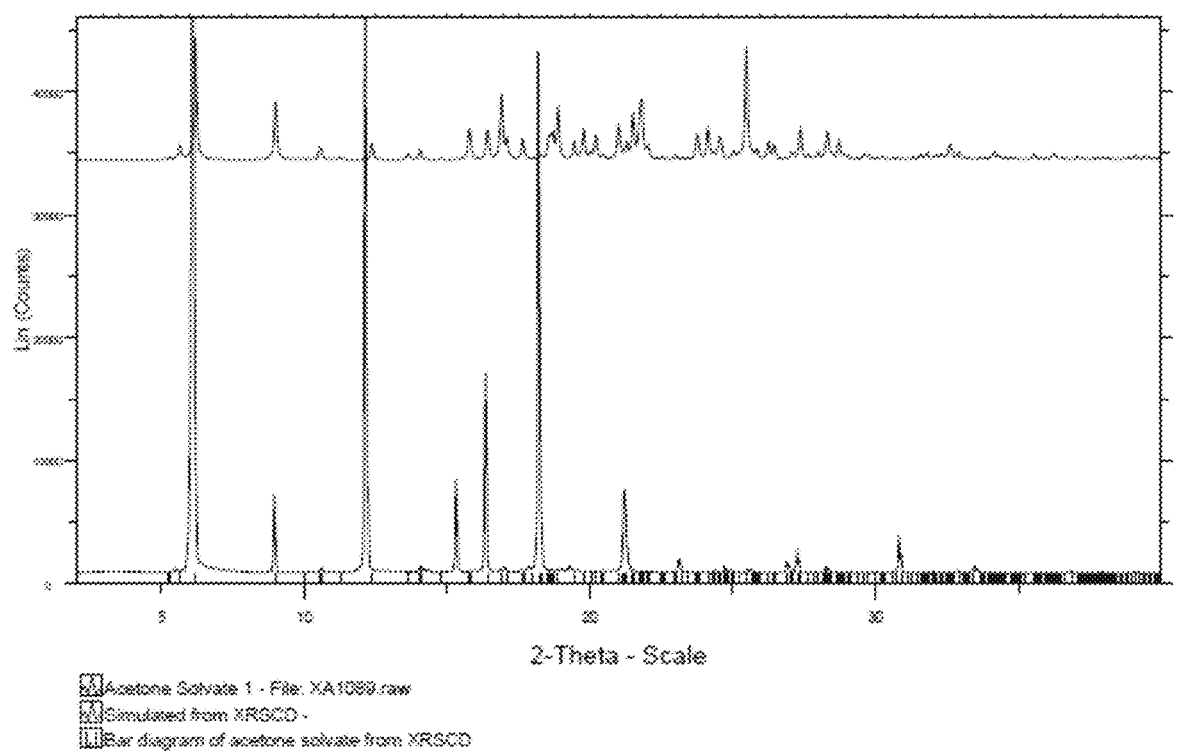

FIG. 32: The XRPD of Form 9 (Acetone) of 3-(3-methoxy-4-((4-methoxybenzyl)oxy)benzyl)-6-(1-methyl-1H-pyrazol-4-yl)-3H-imidazo[4,5-b]pyridin-2-amine is presented.

Figure 33:
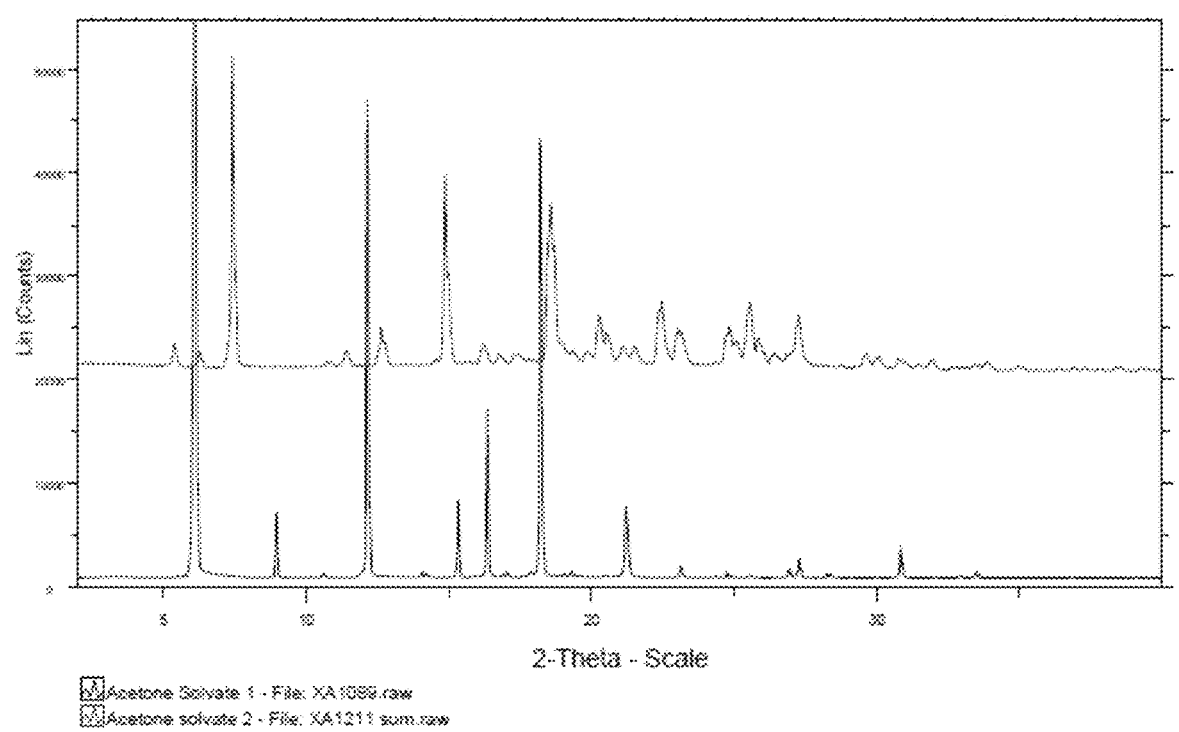

FIG. 33: XRPD Comparison of Form 10 (Acetone) and Form 9 (Acetone). This figure provides a comparison of the two forms of 3-(3-methoxy-4-((4-methoxybenzyl)oxy)benzyl)-6-(1-methyl-1H-pyrazol-4-yl)-3H-imidazo[4,5-b]pyridin-2-amine obtained in acetone.

Figure 34:
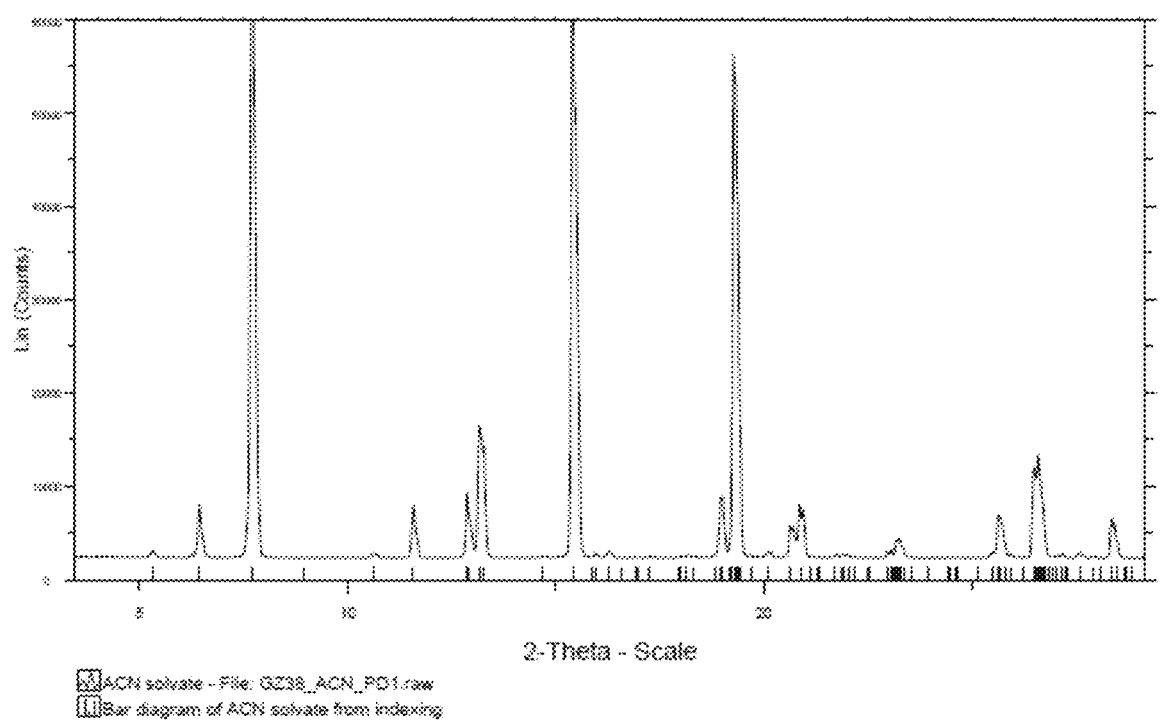

FIG. 34: XRPD of Form 11 (Acetonitrile). The XRPD of Form 11 (Acetonitrile) of 3-(3-methoxy-4-((4-methoxybenzyl)oxy)benzyl)-6-(1-methyl-1H-pyrazol-4-yl)-3H-imidazo[4,5-b]pyridin-2-amine is presented.

Figure 35:
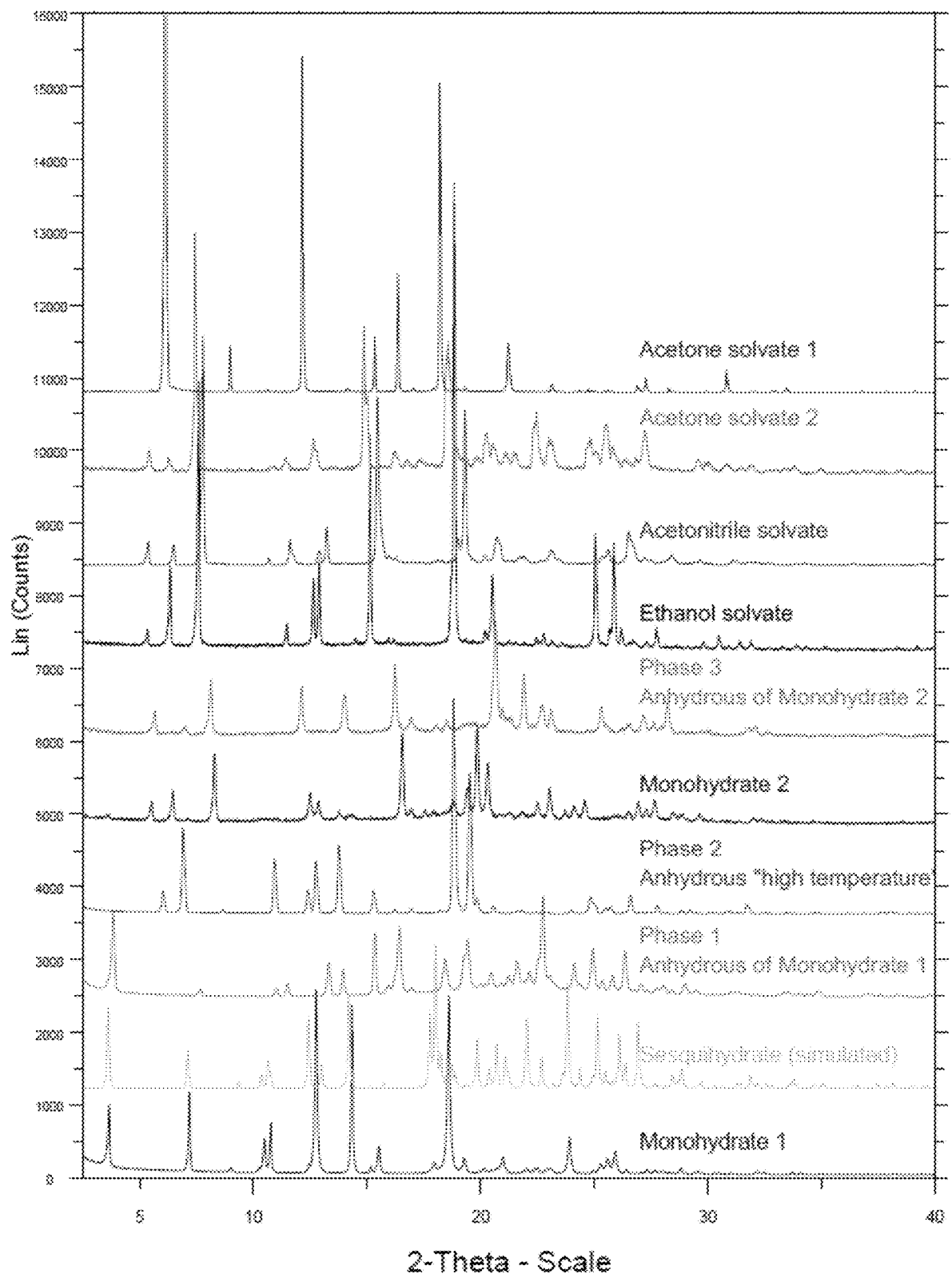

FIG. 35: Solid Crystalline Phases of 3-(3-methoxy-4-((4-methoxybenzyl)oxy)benzyl)-6-(1-methyl-1H-pyrazol-4-yl)-

3H-imidazo[4,5-b]pyridin-2-amine. This figure provides a comparison of the ten crystalline forms of 3-(3-methoxy-4-((4-methoxybenzyl)oxy)benzyl)-6-(1-methyl-1H-pyrazol-4-yl)-3H-imidazo[4,5-b]pyridin-2-amine obtained in experiments.

DETAILED DESCRIPTION OF THE INVENTION

This invention relates to pharmaceutical formulations of 3-(3-methoxy-4-((4-methoxybenzyl)oxy)benzyl)-6-(1-methyl-1H-pyrazol-4-yl)-3H-imidazo[4,5-b]pyridin-2-amine, a tropomyosin-related kinase inhibitor ("Trk inhibitor"), and a monohydrate form of 3-(3-methoxy-4-((4-methoxybenzyl)oxy)benzyl)-6-(1-methyl-1H-pyrazol-4-yl)-3H-imidazo[4,5-b]pyridin-2-amine.

The Trk inhibitor microcrystalline solution pharmaceutical formulations comprise 3-(3-methoxy-4-((4-methoxybenzyl)oxy)benzyl)-6-(1-methyl-1H-pyrazol-4-yl)-3H-imidazo[4,5-b]pyridin-2-amine in its monohydrate form, which shows improved characteristics over the anhydrate form.

The instant invention also relates to extended release pharmaceutical formulations of the Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine, comprising 3-(3-methoxy-4-((4-methoxybenzyl)oxy)benzyl)-6-(1-methyl-1H-pyrazol-4-yl)-3H-imidazo[4,5-b]pyridin-2-amine-loaded microspheres.

This invention further relates to the use of these pharmaceutical formulations to treat diseases including inflammatory diseases, autoimmune disease, defects of bone metabolism, and cancer, as well as in the treatment of osteoarthritis (OA), pain, post-operative pain, and pain associated with OA.

The pharmaceutical formulations of the Trk inhibitor of the instant invention inhibit tropomyosin-related kinase A (TrkA), tropomyosin-related kinase B (TrkB), tropomyosin-related kinase C (TrkC), and c-FMS (the cellular receptor for colony stimulating factor-1 (CSF-1)). Tropomyosin-related kinases (Trk) are high affinity receptors activated by soluble growth factors called neutrophins (NT). TrkA, also known as neurotrophic tyrosine kinase receptor type 1, is activated by nerve growth factor (NGF). TrkB is activated by brain derived growth factor and NT-4/5. TrkC is activated by NT3. The activation of Trk leads to the activation of downstream kinases that are implicated in cell signaling, including cell proliferation, survival, angiogenesis and metastasis. Trk have been implicated in a number of diseases, including OA.

The pharmaceutical formulations of the Trk inhibitor of the instant invention can also inhibit c-FMS (the cellular receptor for colony stimulating factor-1 (CSF-1). C-FMS plays a role in the regulation of macrophage function, and is believed to play a role in inflammatory diseases, autoimmune disease, defects of bone metabolism and cancer (Burns and Wilks, 2011, Informa Healthcare).

OA is a prevalent and debilitating joint disease characterized by chronic pain and destruction of articular cartilage. Recent clinical trials have confirmed a role for blocking NGF in OA knee pain, demonstrating significant pain relief and high responder rates in patients treated by intravenous infusion with anti-NGF blocking antibodies (Lane, 2010, *N Engl J Med*). However, this modality may lead to an increased risk for adverse events due to systemic inhibition of NGF signaling (FDA Arthritis Advisory Committee Meeting to Discuss Safety Issues Related to the Anti-Nerve Growth Factor Agents; http://www.fda.gov/AdvisoryCommittees/Calendar/ucm286556.htm) Accordingly, a novel approach toward targeting NGF-mediated OA pain has been adopted through the development of Trk inhibitors, specifically TrkA inhibitors, the high-affinity receptor for NGF (Nicol, 2007, Molecular Interv). The Trk inhibitors of the present invention are delivered locally and thereby avoid the systemic distribution observed with intravenous anti-NGF administration. This treatment strategy provides enhanced dosing convenience, as well greater safety by allowing for the maintenance of physiologically necessary NGF signaling (i.e. sensory/sympathetic nerve maintenance, angiogenesis) at non-local sites.

This invention relates to pharmaceutical formulations of the Trk inhibitor and methods of treating disease with pharmaceutical formulations of the Trk inhibitor. More particularly, the invention pertains to methods of treating pain, OA, pain associated with OA, post-operative pain, inflammatory diseases, autoimmune disease, defects of bone metabolism and cancer with pharmaceutical formulations of the Trk inhibitors. The pharmaceutical compositions of Trk inhibitors can be administered in multiple dosage forms, including an injection for local delivery both as a microcrystalline suspension and in extended release formulations. The Trk inhibitor is the active pharmaceutical ingredient in pharmaceutical compositions comprising the Trk inhibitor. The Trk inhibitor can also be co-administered and/or co-formulated with other active ingredients for the treatment of disease, including the treatment of pain, OA and pain associated with OA.

The pharmaceutical formulations of the Trk inhibitor of the present invention comprise 3-(3-methoxy-4-((4-methoxybenzyl)oxy)benzyl)-6-(1-methyl-1H-pyrazol-4-yl)-3H-imidazo[4,5-b]pyridin-2-amine, represented by Formula (I) below, as the active pharmaceutical ingredient. 3-(3-methoxy-4-((4-methoxybenzyl)oxy)benzyl)-6-(1-methyl-1H-pyrazol-4-yl)-3H-imidazo[4,5-b]pyridin-2-amine is also known as GZ389988.

Formula (I)

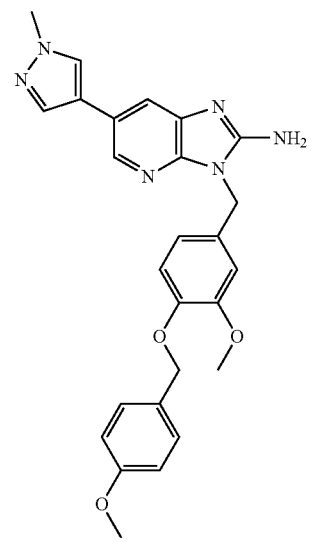

3-(3-methoxy-4-((4-methoxybenzyl)-oxy)benzyl)-6-(1-methyl-1H-pyrazol-4-yl)-3H-imidazo[4,5-b]pyridin-2-amine (GZ389988)

The problem to be solved with this invention is the difficulty in formulating compositions comprising 3-(3- methoxy-4-((4-methoxybenzyl)oxy)benzyl)-6-(1-methyl-1H-pyrazol-4-yl)-3H-imidazo[4,5-b]pyridin-2-amine. The solution to this problem is the discovery that the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine has improved physical and chemical properties, including better physical stability and slower aqueous dissolution, compared to the anhydrate form. The anhydrate form of 3-(3-methoxy-4-((4-methoxybenzyl)oxy)benzyl)-6-(1-methyl-1H-pyrazol-4-yl)-3H-imidazo[4,5-b]pyridin-2-amine proved relatively unstable in solution, yielding issues with its formulation into a pharmaceutical composition. The anhydrate form exhibits variable solid form changes under certain conditions, including conversion to the hydrate. The monohydrate form of 3-(3-methoxy-4-((4-methoxybenzyl)oxy)benzyl)-6-(1-methyl-1H-pyrazol-4-yl)-3H-imidazo[4,5-b]pyridin-2-amine allowed for additional stability and is essential to avoid polymorphic conversion upon long term storage and during processing, and lead to enhanced physical stability. Further, slower dissolution in aqueous solution with the monohydrate form was observed. The monohydrate form of 3-(3-methoxy-4-((4-methoxybenzyl)oxy)benzyl)-6-(1-methyl-1H-pyrazol-4-yl)-3H-imidazo[4,5-b]pyridin-2-amine, also known as GZ389988A, is represented by Formula (II) below.

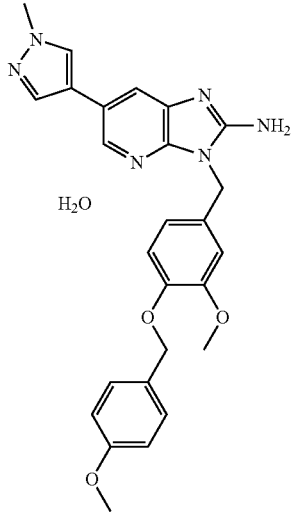

Formula (II)

Monohydrate Form of
3-(3-methoxy-4-((4-methoxybenzyl)-
oxy)benzyl)-6-(1-methyl-1H-pyrazol-
4-yl)-3H-imidazo[4,5-b]pyridin-
2-amine (GZ389988A)

The molecular weight of 3-(3-methoxy-4-((4-methoxybenzyl)oxy)benzyl)-6-(1-methyl-1H-pyrazol-4-yl)-3H-imidazo[4,5-b]pyridin-2-amine is 470.54 g/mol, and the elemental formula is $C_{26}H_{26}N_6O_3$. The monohydrate form of 3-(3-methoxy-4-((4-methoxybenzyl)oxy)benzyl)-6-(1-methyl-1H-pyrazol-4-yl)-3H-imidazo[4,5-b]pyridin-2-amine is an off-white powder and under a polarized light microscope it appears to be fine needles or fiber-like particles.

The monohydrate form of 3-(3-methoxy-4-((4-methoxybenzyl)oxy)benzyl)-6-(1-methyl-1H-pyrazol-4-yl)-3H-imidazo[4,5-b]pyridin-2-amine is synthesized according to Example 1.

A particular embodiment of this invention is a crystalline form of 3-(3-methoxy-4-((4-methoxybenzyl)oxy)benzyl)-6-(1-methyl-1H-pyrazol-4-yl)-3H-imidazo[4,5-b]pyridin-2-amine, wherein the x-ray powder diffraction pattern (XRPD) contains the following 2θ peaks measured using $CuK_\alpha$ radiation: 7.14, 8.89, 10.22, 12.42, 12.73 and 14.31. Details on the method of obtaining the XRPD calculations are provided in Example 1. Another embodiment of the invention is a pharmaceutical formulation comprising the crystalline form of the Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine and a pharmaceutically acceptable excipient.

Another embodiment of this invention relates to the other crystal forms of the Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine in other solvents, including ethanol, acetone, acetonitrile, and mixed solvents. Details on the other forms of 3-(3-methoxy-4-((4-methoxybenzyl)oxy)benzyl)-6-(1-methyl-1H-pyrazol-4-yl)-3H-imidazo[4,5-b]pyridin-2-amine and the method of obtaining the XRPD calculations are provided in Example 4.

The invention also relates to a composition comprising the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine, represented by Formula (I), and pharmaceutical formulation comprising the monohydrate form of the Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine and a pharmaceutically acceptable excipient.

The pharmaceutical formulations of the Trk inhibitor may comprise one or more pharmaceutically acceptable excipients. Modes of administration of the pharmaceutical formulations of the Trk inhibitor include oral, sublingual, intravenous, subcutaneous, intramuscular, intra-articular, transdermal, rectal, inhalation, intrathecal/intraventricular, and topical. Accordingly, the pharmaceutical formulations of the Trk inhibitor may be formulated, for example, as a capsule, tablet, powder, solution, suspension, emulsion, lyophilized powder, or an extended release formulation comprising injectable microcapsules. The excipients used in the pharmaceutical formulations of the Trk inhibitor will depend on the route of administration for which the pharmaceutical formulation of the Trk inhibitor is intended.

Suitable excipients include, but are not limited to, inorganic or organic materials such as diluents, solvents, gelatin, albumin, lactose, starch, stabilizers, melting agents, emulsifying agents, suspending agents, salts and buffers. Suitable pharmaceutically acceptable excipients for intra-articular formulations such as solutions or suspensions include, but are not limited to, commercially available inert gels or liquids.

Given the low solubility of the Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine and the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine, a suspending agent is needed to make a microcrystalline suspension formulation for intra-articular injection comprising the Trk inhibitor as the active pharmaceutical ingredient Commonly used pharmaceutically acceptable suspending agents include: acacia, agar, alginic acid, bentonite, calcium stearate, carbomer, carboxymethylcellulose (calcium and sodium), carrageenan, cellulose (microcrystalline, microcrystalline and carboxymethylcellulose sodium, powdered), colloidal silicone dioxide, destrin, gelatin, guar gum, hectorite, hydrophobic colloidal silica, hydroxyethyl cellulose, hydroxymethyl cellulose, hydroxypropyl cellulose, hypromellose, kaolin, magnesium aluminum silicate, maltitol solutions, medium-chain triglycerides, methylcellulose, phenylmercuric borate, phospholipids, poycarbophil, polyethylene glycol, polyoxyethylene sorbitan fatty acid esters, povidone (polyvinylpyrrolidone), propylene glycol alginate, saponite, sesame oil, sodium alginate, sorbitan esters, sucrose, tragacanth, vitamin E polyethylene glycol succinate, and xanthan gum (Handbook of Pharmaceutical Excipients, $6^{th}$ Edition).

Buffering agents are also used in the formulation of a solution for intra-articular administration where the active ingredient is the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine, the Trk inhibitor. Pharmaceutically acceptable buffering agents include: adipic acid, ammonia solution, boric acid, calcium carbonate, calcium hydroxide, calcium lactate, calcium phosphate, tribasic, citric acid monohydrate, dibasic sodium phosphate, diethanolamine, glycine, maleic Acid, malic acid, methionine, monobasic sodium phosphate, monoethanolamine, monosodium glutamate, phosphoric acid, potassium citrate, sodium acetate, sodium bicarbonate, sodium borate, sodium carbonate, sodium citrate dihydrate, sodium hydroxide, sodium lactate, and triethanolamine (Handbook of Pharmaceutical Excipients, $6^{th}$ Edition).

As the pharmaceutical formulations of the Trk inhibitor of the instant invention are formulations for intra-articular administration, they also may contain diluents. Suitable diluents for applications as in the instant invention include: malitol, sunflower oil, ammonium alginate, calcium carbonate, calcium lactate, calcium phosphatedibasic anhydrous, dibasic dihydrate, tribasic, calcium silicate, calcium sulfate, cellulose (powdered, silicified microcrystalline), cellulose acetate, compressible sugar, confectioner's sugar, corn starch and pregelatinized starch, dextrates, dextrin, dextrose, erythritol, ethylcellulose, fructose, fumaric acid, glyceryl palmitostearate, inhalation lactose, isomalt, kaolin, lactitol, lactose (anhydrous, monohydrate and corn starch, monohydrate and microcrystalline cellulose, spray dried), magnesium carbonate, magnesium oxide, maltodextrin, maltose, mannitol, medium-chain triglycerides, microcrystalline cellulose, polydextrose, polymethacrylates, simethicone, sodium alginate, sodium chloride, sorbitol, starch (pregelatinized, sterilizable maize), sucrose, sugar spheres, sulfobutylether b-cyclodextrin, talc, tragacanth, trehalose, xylitol (Handbook of Pharmaceutical Excipients, 6th Edition).

Microcrystalline suspension pharmaceutical formulations of the Trk inhibitor with the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine as the active ingredient are described in Example 2.

This invention also relates to methods of manufacturing a crystalline form of 3-(3-methoxy-4-((4-methoxybenzyl) oxy)benzyl)-6-(1-methyl-1H-pyrazol-4-yl)-3H-imidazo[4, 5-b]pyridin-2-amine and manufacturing the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine comprising:
a. Mixing 3-(3-methoxy-4-((4-methoxybenzyl)oxy)benzyl)-6-(1-methyl-1H-pyrazol-4-yl)-3H-imidazo[4,5-b] pyridin-2-amine with a solvent to form a suspension;
b. Stirring the suspension;
c. Collecting the solids in the suspension by filtration; and
d. Drying the solids.

In this method, the solvent used to form the suspension may be a mixture of acetone and water. Further, the suspension may be stirred overnight, and the solids that are collected may be air dried.

Extended release pharmaceutical formulations of the Trk inhibitor may comprise either 3-(3-methoxy-4-((4-methoxybenzyl)oxy)benzyl)-6-(1-methyl-1H-pyrazol-4-yl)-3H-imidazo[4,5-b]pyridin-2-amine or the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine as, in the case of formulations produced from drug solutions, the Trk inhibitor is dissolved in solvent prior to microencapsulation and formulation, and in the case of formulations produced from drug suspensions, the Trk inhibitor is suspended in solvent prior to microencapsulation and formulation. A solution or suspension containing the active ingredient is then combined with various polymers, as set forth in the Example 3, in order to microencapsulate the 3-(3-methoxy-4-((4-methoxybenzyl)oxy)benzyl)-6-(1-methyl-1H-pyrazol-4-yl)-3H-imidazo[4,5-b]pyridin-2-amine. The microencapsulation of 3-(3-methoxy-4-((4-methoxybenzyl)oxy)benzyl)-6-(1-methyl-1H-pyrazol-4-yl)-3H-imidazo[4,5-b]pyridin-2-amine helps to provide a formulation with an extended effect, up to and over 3 months in duration, and to provide sustained therapeutic effect in the patient.

In a particular embodiment of the invention, the pharmaceutical formulation comprising the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine comprises a pharmaceutically acceptable diluent, a pharmaceutically acceptable suspending agent and a pharmaceutically acceptable buffering agent. In certain embodiments of the pharmaceutical formulations of the instant invention, the diluent is sorbitol, the suspending agent is povidone, and the buffering agent is phosphoric acid.

The instant invention also relates to extended release pharmaceutical formulations comprising 3-(3-methoxy-4-((4-methoxybenzyl)oxy)benzyl)-6-(1-methyl-1H-pyrazol-4-yl)-3H-imidazo[4,5-b]pyridin-2-amine-loaded microspheres. In these extended release formulations, the Trk inhibitor may be either 3-(3-methoxy-4-((4-methoxybenzyl) oxy)benzyl)-6-(1-methyl-1H-pyrazol-4-yl)-3H-imidazo[4, 5-b]pyridin-2-amine or the monohydrate form of the compound. The drug-loaded microspheres may further comprise a polymer.

In a specific embodiment of a Trk inhibitor-loaded microsphere comprising a polymer, the polymer is selected from poly(D,L-lactide), poly(D,L-lactide-co-glycolide) and a combination of both poly(D,L-lactide) and poly(D,L-lactide-co-glycolide). In certain embodiments of the invention, the poly(D,L-lactide) used in the extended release formulation has an inherent viscosity of 0.16-0.35 dL/g. In another embodiment, poly(D,L-lactide) has an inherent viscosity of 0.16-0.24 dL/g. In yet another embodiment, the poly(D,L-lactide) has an inherent viscosity of 0.25-0.35 dL/g. In certain embodiments of the invention, the poly(D,L-lactide-co-glycolide) has an inherent viscosity of 0.14-0.24 dL/g. In one embodiment, poly(D,L-lactide-co-glycolide) has an inherent viscosity of 0.14-0.22 dL/g. In another embodiment the poly(D,L-lactide-co-glycolide) has an inherent viscosity of 0.16-0.24 dL/g.

In an extended release formulation comprising both poly (D,L-lactide) and poly(D,L-lactide-co-glycolide), the poly (D,L-lactide) has an inherent viscosity of 0.16-0.35 dL/g and the poly(D,L-lactide-co-glycolide) has an inherent viscosity of 0.14-0.24 dL/g. In one embodiment, the poly(D,L-lactide)

has an inherent viscosity of 0.16-0.24 dL/g and the poly(D, L-lactide-co-glycolide) has an inherent viscosity of 0.14-0.22 dL/g. In another embodiment, the poly(D,L-lactide) has an inherent viscosity of 0.16-0.24 dL/g and the poly(D,L-lactide-co-glycolide) has an inherent viscosity of 0.16-0.24 dL/g. In yet another embodiment, the poly(D,L-lactide) has an inherent viscosity of 0.25-0.35 dL/g and the poly(D,L-lactide-co-glycolide) has an inherent viscosity of 0.14-0.22 dL/g. And in yet another embodiment, the poly(D,L-lactide) has an inherent viscosity of 0.25-0.35 dL/g and the poly(D, L-lactide-co-glycolide) has an inherent viscosity of 0.16-0.24 dL/g.

In another embodiment, the extended release pharmaceutical formulations comprising Trk inhibitor-loaded microspheres comprise a 9:1 ratio of poly(D,L-lactide) and poly(D,L-lactide-co-glycolide). In these extended release formulations, the poly(D,L-lactide) has an inherent viscosity of 0.16-0.35 dL/g and the poly(D,L-lactide-co-glycolide) has an inherent viscosity of 0.14-0.24 dL/g.

In another embodiment, the extended release pharmaceutical formulations comprising Trk inhibitor-loaded microspheres comprise a 9.5:0.5 ratio of poly(D,L-lactide) and poly(D,L-lactide-co-glycolide). In these formulations, the poly(D,L-lactide) has an inherent viscosity of 0.16-0.35 dL/g and the poly(D,L-lactide-co-glycolide) has an inherent viscosity of 0.14-0.24 dL/g.

In the extended release pharmaceutical formulation comprising Trk inhibitor-loaded microspheres, the microspheres are loaded with 1% w/w to 99% w/w 3-(3-methoxy-4-((4-methoxybenzyl)oxy)benzyl)-6-(1-methyl-1H-pyrazol-4-yl)-3H-imidazo[4,5-b]pyridin-2-amine. In a more specific embodiment, the microspheres are loaded with 12% w/w to 50% w/w 3-(3-methoxy-4-((4-methoxybenzyl)oxy)benzyl)-6-(1-methyl-1H-pyrazol-4-yl)-3H-imidazo[4,5-b]pyridin-2-amine. In yet another embodiment, the microspheres are loaded with 12% w/w to 50% w/w 3-(3-methoxy-4-((4-methoxybenzyl)oxy)benzyl)-6-(1-methyl-1H-pyrazol-4-yl)-3H-imidazo[4,5-b]pyridin-2-amine. In more specific embodiments, the microspheres are loaded with 12% w/w, 15% w/w, 16% w/w, 17% w/w, 18% w/w, 19% w/w, 20% w/w, 25% w/w, 30% w/w, 40% w/w or even 50% w/w 3-(3-methoxy-4-((4-methoxybenzyl)oxy)benzyl)-6-(1-methyl-1H-pyrazol-4-yl)-3H-imidazo[4,5-b]pyridin-2-amine.

This invention also relates to methods of manufacturing 3-(3-methoxy-4-((4-methoxybenzyl)oxy)benzyl)-6-(1-methyl-1H-pyrazol-4-yl)-3H-imidazo[4,5-b]pyridin-2-amine-loaded microcapsules by solvent extraction and by spray drying.

One solvent extraction method of the instant invention relates to forming Trk inhibitor-loaded microspheres from a solution of 3-(3-methoxy-4-((4-methoxybenzyl)oxy)benzyl)-6-(1-methyl-1H-pyrazol-4-yl)-3H-imidazo[4,5-b]pyridin-2-amine. This method comprises:

a. Dissolving the 3-(3-methoxy-4-((4-methoxybenzyl)oxy)benzyl)-6-(1-methyl-1H-pyrazol-4-yl)-3H-imidazo[4,5-b]pyridin-2-amine in an organic solvent to form a drug solution;

b. Adding a polymer to the drug solution to form a polymer/3-(3-methoxy-4-((4-methoxybenzyl)oxy)benzyl)-6-(1-methyl-1H-pyrazol-4-yl)-3H-imidazo[4,5-b]pyridin-2-amine solution;

c. Mixing the polymer/3-(3-methoxy-4-((4-methoxybenzyl)oxy)benzyl)-6-(1-methyl-1H-pyrazol-4-yl)-3H-imidazo[4,5-b]pyridin-2-amine solution into an aqueous solution to form an emulsion;

d. Adding deionized water to the emulsion;

e. Forming microspheres from the emulsion by solvent extraction; and f. Sieving the resulting microspheres using a surfactant solution.

In this method, the organic solvent may comprise (i) dichloromethane and methanol, (ii) dichloromethane, (iii) benzyl alcohol and methanol, (iv) dichloromethane and benzyl alcohol, (v) chloroform, (v) chloroform and methanol, or (vii) chloroform and benzyl alcohol. The polymer in this method may be poly(D,L-lactide), poly(D,L-lactide-co-glycolide), or a combination of poly(D,L-lactide) and poly(D,L-lactide-co-glycolide). The aqueous solution in this method may be polyvinyl alcohol in water. The surfactant solution in this method may be poloxamer 407 in water, polysorbate 80 in water, or polysorbate 20 in water.

Another solvent extraction method of the instant invention relates to forming Trk inhibitor-loaded microspheres from a suspension of 3-(3-methoxy-4-((4-methoxybenzyl)oxy)benzyl)-6-(1-methyl-1H-pyrazol-4-yl)-3H-imidazo[4,5-b]pyridin-2-amine. This method comprises:

a. Dispersing the 3-(3-methoxy-4-((4-methoxybenzyl)oxy)benzyl)-6-(1-methyl-1H-pyrazol-4-yl)-3H-imidazo[4,5-b]pyridin-2-amine in an organic solvent to form a drug suspension;

b. Adding a polymer to the drug suspension to form a polymer/3-(3-methoxy-4-((4-methoxybenzyl)oxy)benzyl)-6-(1-methyl-1H-pyrazol-4-yl)-3H-imidazo[4,5-b]pyridin-2-amine dispersion;

c. Mixing the polymer/3-(3-methoxy-4-((4-methoxybenzyl)oxy)benzyl)-6-(1-methyl-1H-pyrazol-4-yl)-3H-imidazo[4,5-b]pyridin-2-amine dispersion with an aqueous solution to form an emulsion;

d. Adding deionized water to the emulsion;

e. Forming microspheres from the emulsion by solvent extraction; and f. Sieving the resulting microspheres using a surfactant solution.

In this method, the organic solvent may comprise (i) ethyl acetate, (ii) dichloromethane, (iii) chloroform, (iv) ethyl acetate and dichloromethane, (v) ethyl acetate and chloroform, (vi) dichloromethane and chloroform or (vii) ethyl acetate, dichloromethane and chloroform. The polymer in this method may be poly(D,L-lactide), poly(D,L-lactide-co-glycolide), or a combination of poly(D,L-lactide) and poly(D,L-lactide-co-glycolide). The aqueous solution in this method may be polyvinyl alcohol in water. The surfactant solution in this method may be poloxamer 407 in water, polysorbate 80 in water, or polysorbate 20 in water.

In another aspect, the invention relates to a method of forming Trk inhibitor-loaded microspheres from a solution of 3-(3-methoxy-4-((4-methoxybenzyl)oxy)benzyl)-6-(1-methyl-1H-pyrazol-4-yl)-3H-imidazo[4,5-b]pyridin-2-amine-loaded microcapsules by spray drying. This method comprises:

a. Dissolving the 3-(3-methoxy-4-((4-methoxybenzyl)oxy)benzyl)-6-(1-methyl-1H-pyrazol-4-yl)-3H-imidazo[4,5-b]pyridin-2-amine in an organic solvent to form a drug solution;

b. Adding a polymer to the drug solution to form a polymer/3-(3-methoxy-4-((4-methoxybenzyl)oxy)benzyl)-6-(1-methyl-1H-pyrazol-4-yl)-3H-imidazo[4,5-b]pyridin-2-amine solution; and c. Pumping the polymer/3-(3-methoxy-4-((4-methoxybenzyl)oxy)benzyl)-6-(1-methyl-1H-pyrazol-4-yl)-3H-imidazo[4,5-b]pyridin-2-amine solution through a sprayer into a dryer to form a spherical particle.

In this method, the organic solvent may comprise (i) dichloromethane and methanol, (ii) dichloromethane, (iii) benzyl alcohol and methanol, (iv) dichloromethane and benzyl alcohol, (v) chloroform, (v) chloroform and methanol, or (vii) chloroform and benzyl alcohol. The polymer in this method may be poly(D,L-lactide), poly(D,L-lactide-coglycolide), or a combination of poly(D,L-lactide) and poly (D,L-lactide-co-glycolide). Additional parameters of this method relate to the spray rate and atomizing nitrogen flow of the sprayer. The spray rate may be 0.7 mL/min; the atomizing nitrogen flow may be 4 L/min. The temperature at various points in the dryer are also elements that may be controlled to impact the resulting microsphere size. In this method, the dryer may have an inlet temperature of 50° C., a chamber temperature of 40-45° C., and an exhaust temperature of 20-30° C. In a more specific embodiment, the chamber temperature is 40-43° C.; more specifically the chamber temperature is 41-43° C. In another embodiment, the exhaust temperature is 22-28° C.

In yet another aspect, the invention relates to a method of forming Trk inhibitor-loaded microspheres from a suspension of 3-(3-methoxy-4-((4-methoxybenzyl)oxy)benzyl)-6-(1-methyl-1H-pyrazol-4-yl)-3H-imidazo[4,5-b]pyridin-2-amine-loaded microcapsules by spray drying. This method comprises:
  a. Dispersing the 3-(3-methoxy-4-((4-methoxybenzyl)oxy)benzyl)-6-(1-methyl-1H-pyrazol-4-yl)-3H-imidazo[4,5-b]pyridin-2-amine in an organic solvent to form a drug suspension;
  b. Adding a polymer to the drug suspension to form a polymer/3-(3-methoxy-4-((4-methoxybenzyl)oxy)benzyl)-6-(1-methyl-1H-pyrazol-4-yl)-3H-imidazo[4,5-b] pyridin-2-amine dispersion; and
  c. Pumping the polymer/3-(3-methoxy-4-((4-methoxybenzyl)oxy)benzyl)-6-(1-methyl-1H-pyrazol-4-yl)-3H-imidazo[4,5-b]pyridin-2-amine dispersion through a sprayer into a dryer to form a spherical particle.

In this method, the organic solvent may comprise (i) ethyl acetate, (ii) dichloromethane, (iii) chloroform, (iv) ethyl acetate and dichloromethane, (v) ethyl acetate and chloroform, (vi) dichloromethane and chloroform or (vii) ethyl acetate, dichloromethane and chloroform. The polymer in this method may be poly(D,L-lactide), poly(D,L-lactide-coglycolide), or a combination of poly(D,L-lactide) and poly (D,L-lactide-co-glycolide). Additional parameters of this method relate to the spray rate and atomizing nitrogen flow of the sprayer. The spray rate may be 0.7 mL/min; the atomizing nitrogen flow may be 4 L/min. The temperature at various points in the dryer are also elements that may be controlled to impact the resulting microsphere size. In this method, the dryer may have an inlet temperature of 50° C., a chamber temperature of 40-45° C., and an exhaust temperature of 20-30° C. In a more specific embodiment, the chamber temperature is 40-43° C.; more specifically the chamber temperature is 41-43° C. In another embodiment, the exhaust temperature is 22-28° C.

The following non-limiting Examples illustrate the various embodiments of the invention, including methods for preparing the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine, pharmaceutical formulations with the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine, extended release pharmaceutical formulations of 3-(3-methoxy-4-((4-methoxybenzyl)oxy)benzyl)-6-(1-methyl-1H-pyrazol-4-yl)-3H-imidazo[4,5-b]pyridin-2-amine and methods for producing these extended release formulations.

EXAMPLES

Example 1: The Monohydrate Form of 3-(3-Methoxy-4-((4-methoxybenzyl)oxy)benzyl)-6-(1-methyl-1H-pyrazol-4-yl)-3H-imidazo[4,5-b]pyridin-2-amine

Example 1-1: Synthesis of the Monohydrate Form of 3-(3-Methoxy-4-((4-methoxybenzyl)oxy)benzyl)-6-(1-methyl-1H-pyrazol-4-yl)-3H-imidazo[4,5-b]pyridin-2-amine To a stirred solution of 3-methoxy-4-(4-methoxybenzyloxy)phenyl)methanamine (2.00 g, 7.32 mmol) and 5-bromo-2-chloro-3-nitropyridine (1.66 g, 6.97 mmol) in acetonitrile (50 mL) was added N,N-diisopropylethylamine (1.13 g, 8.71 mmol). The resulting mixture was heated to reflux and allowed to stir. After 64 h, the reaction mixture was allowed to cool to room temperature and was diluted with water. The mixture was extracted twice with dichloromethane. The combined organic phases were dried over magnesium sulfate, filtered, and concentrated to provide 3.34 g (>100%) of 5-bromo-N-(3-methoxy-4-(4-methoxybenzyloxy)benzyl)-3-nitropyridin-2-amine as a yellow-brown solid.

To a stirred solution of 5-bromo-N-(3-methoxy-4-(4-methoxybenzyloxy)benzyl)-3-nitropyridin-2-amine in tetrahydrofuran (40 mL), ethanol (40 mL), and water (40 mL) was added sodium hydrosulfite (6.09 g, 34.99 mmol). The resulting mixture was heated to reflux and allowed to stir. After 4 h, the reaction mixture was allowed to cool to room temperature and was diluted with water. The yellow mixture was extracted three times with dichloromethane. The combined organic phases were washed with brine, dried (magnesium sulfate), filtered, and concentrated to provide 3.10 g of a yellow-brown solid. Chromatographic purification (Combi-Flash 40 g SiO$_2$ gold column, 1-2.5% methanol/dichloromethane) afforded 1.28 g (51%) of 5-bromo-N$^2$-(3-methoxy-4-(4-methoxybenzyloxy)benzyl)pyridine-2,3-diamine as a yellow solid.

To a stirred solution of 5-bromo-N$^2$-(3-methoxy-4-(4-methoxybenzyloxy)benzyl)pyridine-2,3-diamine (0.850 g, 1.91 mmol) in dichloromethane (30 mL) and methanol (30 mL) was added cyanogen bromide (5.0 M in acetonitrile, 573 μL, 2.87 mmol). The resulting solution was allowed to stir at room temperature. After 24 h, a second aliquot of cyanogen bromide solution was added (600 μL) and stirring continued. After 48 h, a third aliquot of cyanogen bromide solution (600 μL) was added and stirring continued. After a total of 72 h, the reaction mixture was concentrated, and the residue was dissolved in dichloromethane. The solution was washed with 1N sodium hydroxide solution, dried over magnesium sulfate, filtered, and concentrated to provide 1.17 g of a brown solid. Chromatographic purification (Combi-Flash, 40 g SiO$_2$ gold column, 1-10% 2M ammonia in methanol/dichloromethane) afforded 0.28 g (32%) of 6-bromo-3-(3-methoxy-4-(4-methoxybenzyloxy)benzyl)-3H-imidazo[4,5-b]pyridin-2-amine as a brown solid.

To a stirred solution of 6-bromo-3-(3-methoxy-4-(4-methoxybenzyloxy)benzyl)-3H-imidazo[4,5-b]pyridin-2-amine (0.25 g, 0.53 mmol) in 1,4-dioxane (10 mL) and water (4 mL) was added 1-methyl-4-(4,4,5,5-tetramethyl-1,3,2-dioxaborolan-2-yl)-1H-pyrazole (0.14 g, 0.66 mmol), potassium phosphate tribasic (0.39 g, 1.84 mmol), tricyclohexylphosphine (0.015 g, 0.052 mmol), palladium(II) acetate (0.005 g, 0.026 mmol). The reaction mixture heated to 125° C. in a microwave reactor. After 15 min, the reaction mixture was allowed to cool to room temperature and was diluted with water. The mixture was extracted twice with ethyl acetate. The combined organic phases were washed with brine, dried over magnesium sulfate, filtered, and concentrated to provide 0.36 g of a greenish brown solid. Chromatographic purification (Combi-Flash, 12 g $SiO_2$ gold column, 1-10% 2M ammonia in methanol/dichloromethane) afforded 0.10 g (41%) of the product as a light green solid.

3-(3-methoxy-4-((4-methoxybenzyl)oxy)benzyl)-6-(1-methyl-1H-pyrazol-4-yl)-3H-imidazo[4,5-b]pyridin-2-amine was added to a mixture of acetone (2 mL) and water (0.1 mL). The suspension was stirred by a magnetic stirring bar at room temperature overnight. The solids were collected by filtration and dried in the air. The structure was confirmed by proton NMR. The differential scanning calorimetry (DSC) thermogram exhibits three thermal events at 76.72, 160.13, and 195.78° C., the thermal gravimetric analysis (TGA) thermogram shows 3.7% weight loss from 25-100° C., and the X-ray powder diffraction analysis (XRPD) shows unique peaks at 3.6, 7.1, 8.9, 10.4, 10.7, 12.4, 12.7 and 14.3 2θ peaks measured using $CuK_\alpha$ (accuracy ±0.2°).

Example 1-2: Identification of the Crystalline Structure of the Monohydrate Form of 3-(3-Methoxy-4-((4-methoxybenzyl)oxy)benzyl)-6-(1-methyl-1H-pyrazol-4-yl)-3H-imidazo[4,5-b]pyridin-2-amine The crystalline structure of the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine was also solved. Crystals of the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine were recrystallized from acetone/water. A crystal 0.20*0.08*0.03 mm in size yielded to suitable diffraction frames when it was placed on the top of a MiTeGen MicroMount. X-ray diffraction data were collected on a Bruker/AXS three circle diffractometer, equipped with a SMART APEX area-detector, a low temperature device (model LT 2) and a copper-K microfocus generator, operated at 45 kV/650 μA and a focusing beam Montel multilayer optic with an image focus spot diameter of ~250 μm (Wiesmann et al., 2007). Data were collected using the program package SMART V 5.628 (Bruker AXS, 2001), and processed with the program SAINT+Release 6.45 (Bruker AXS, 2003). This analysis yielded 2459 reflections ($\vartheta_{min}$=1.78, $\vartheta_{max}$=50.21; 0<h<24, −4<k<0, −19<l<19) of which all 2459 reflections were unique ($R_{int}$=n.a., $R_\sigma$=0.1583). Refinement of the cell parameters was performed using 1405 reflections. An empirical absorption correction was applied and the phase problem was solved with the "structure-solution" module of the APEX2 suite.

The structure was refined by least-squares methods (minimization of $(F_o^2-F_c^2)^2$) using the XL module of the APEX2 suite (Bruker AXS, 2011). The positions of all hydrogen atoms were calculated, $S_{goodness\ of\ fit}$=1.085, $R_{all\ data}$=0.1329 ($R_{obs.\ data}$=0.0920 for 1614 reflections with $|F_{obs}|$>4σ, $wR2_{all\ data}$=0.2710, $wR2_{obs.\ data}$=0.2377). The largest unassigned peaks in the difference map correspond to −0.348 versus +0.386 electrons per Å$^3$. The average estimated standard deviation (e.s.d.) of a C—C bond is 0.009 Å, that of an O—C bond is 0.009 Å and that of a N—C bond is 0.009 Å. The average e.s.d. of C—C—C bond angles is 0.7 and that of C—C—C—C torsion angles 1.004°.

The crystalline structure of the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine is presented in FIG. 3. FIG. 4 shows an overlay of the experimental powder pattern with the one calculated from the single crystal structure. The strong degree of matching suggests that the single crystal structure is indicative of the bulk material.

Example 2: 3-(3-Methoxy-4-((4-methoxybenzyl)oxy)benzyl)-6-(1-methyl-1H-pyrazol-4-yl)-3H-imidazo[4,5-b]pyridin-2-amine Monohydrate Microcrystalline Suspension Formulations Microcrystalline suspension pharmaceutical formulations of the Trk inhibitor, where the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine is the active ingredient, were developed. These formulations were developed as a suspension of the insoluble 3-(3-methoxy-4-((4-methoxybenzyl)oxy)benzyl)-6-(1-methyl-1H-pyrazol-4-yl)-3H-imidazo[4,5-b]pyridin-2-amine particles to sustain the delivery of the Trk inhibitor to the body over time. This approach relies on the poor solubility of the active ingredient and dose to control the duration of release; it also shows sustained delivery of approximately 1 month of 3-(3-methoxy-4-((4-methoxybenzyl)oxy)benzyl)-6-(1-methyl-1H-pyrazol-4-yl)-3H-imidazo[4,5-b]pyridin-2-amine in vivo.

Example 2-1: 20 mg/mL 3-(3-Methoxy-4-((4-methoxybenzyl)oxy)benzyl)-6-(1-methyl-1H-pyrazol-4-yl)-3H-imidazo[4,5-b]pyridin-2-amine Monohydrate Microcrystalline Suspension for Injection A pharmaceutical formulation comprising 20 mg of the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine per mL of solution was prepared. The composition of the 20 mg/mL microcrystalline suspension is provided in Table 1 below.

TABLE 1

| 20 mg/mL Microcrystalline Suspension Formulation | | |
|---|---|---|
| Component | Composition per Unit | Function |
| Monohydrate form of 3-(3-methoxy-4-((4-methoxybenzyl)oxy)benzyl)-6-(1-methyl-1H-pyrazol-4-yl)-3H-imidazo[4,5-b]pyridin-2-amine | 72 mg | Active ingredient |
| Sorbitol | 162 mg | Diluent |
| Povidone K17 pyrogen free | 72 mg | Suspending agent |
| Phosphate buffer (10 mM, pH 7.4) | 3.6 mL† | Buffering agent |

†An overfilling of 10% is applied

Example 2-2: Method of Manufacturing the 20 mg/mL 3-(3-Methoxy-4-((4-methoxybenzyl)oxy)benzyl)-6-(1-methyl-1H-pyrazol-4-yl)-3H-imidazo[4,5-b]pyridin-2-amine Monohydrate Microcrystalline Suspension Formulation The 20 mg/mL solution of the monohydrate form of 3-(3-methoxy-4-((4-methoxybenzyl)oxy)benzyl)-6-(1- methyl-1H-pyrazol-4-yl)-3H-imidazo[4,5-b]pyridin-2-amine was prepared according to the following steps:

1. A phosphate buffer 10 mM pH 7.4 is prepared by combining appropriate amounts of Water for Injection (WFI) and sodium dihydrogenophosphate, stirring to complete dissolution, and then adjusting the pH to 7.4 (±0.2) with sodium hydroxide 1N solution.
2. A vehicle is prepared by combining the appropriate amounts of sorbitol and Povidone K17 pyrogen, adding the phosphate buffer 10 mM pH 7.4 and stirring until complete dissolution.
3. The resulting vehicle is then filtered through a 0.22 µm PVDF [polyvinylidene fluoride] hydrophilic filter.
4. A concentrated suspension is obtained by mixing the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine with approximately the vehicle to obtain a 30 mg/mL concentrated suspension.
5. The concentrated suspension, kept under agitation, is filtered on a 75 µm stainless steel sieve.
6. The pre-filtered suspension remains under agitation and is filtered on a 40 µm stainless steel sieve to obtain the concentrate suspension.
7. The concentrate suspension is adjusted with the filtered vehicle to obtain a 20 mg/mL suspension.
8. The final suspension is filled, into sterile and depyrogenated colorless type I glass vials to a 3.6 mL filling volume. Vials are closed with sterile and depyrogenated ETFE coated bromo-butyl stoppers. Stoppers are crimped with sterile aluminum caps and sterile white plastic lids onto the vials.
9. The filled vials are sterilized in autoclaving equipment.

Example 2-3: Clinical Doses of the 20 mg/mL 3-(3-Methoxy-4-((4-methoxybenzyl)oxy)benzyl)-6-(1-methyl-1H-pyrazol-4-yl)-3H-imidazo[4,5-b]pyridin-2-amine Monohydrate Microcrystalline Suspension Formulation The 20 mg/mL microcrystalline suspension of the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine is further modified to achieve the dose and volume to be administered to the patient in the finished drug product configurations. The target doses are reconstituted as necessary from the 20 mg/mL microcrystalline suspension. A summary of the various dosage and volume formats are provided in Table 2.

TABLE 2

Clinical Presentations of the 20 mg/mL 3-(3-Methoxy-4-((4-methoxybenzyl)oxy)benzyl)-6-(1-methyl-1H-pyrazol-4-yl)-3H-imidazo[4,5-b]pyridin-2-amine Monohydrate Microcrystalline Suspension

| Targeted Dose (mg) | Total Volume of Reconstituted Vial (mL) | Final Concentration in Vial (mg/mL) | Volume Administered to Patient (mL) |
|---|---|---|---|
| 3 | 3.47 | 0.98 | 3.2 |
| 10 | 3.95 | 3.29 | 3.2 |
| 30 | 6.60 | 10 | 3.2 |
| 60 | n/a† | 20 | 3.2 |
| 100 | n/a† | 20 | 5.4‡ |

†Reconstitution not required to achieve final concentration.
‡2 × 2.7 mL vials

Example 3: 3-(3-Methoxy-4-((4-methoxybenzyl)oxy)benzyl)-6-(1-methyl-1H-pyrazol-4-yl)-3H-imidazo[4,5-b]pyridin-2-amine Extended Release Formulations In some cases, the duration of drug release is desired to be extended, for example to greater than 3 month exposure time. Accordingly, extended release formulations of the Trk inhibitor 3-(3-methoxy-4-((4-methoxybenzyl)oxy)benzyl)-6-(1-methyl-1H-pyrazol-4-yl)-3H-imidazo[4,5-b]pyridin-2-amine as the active ingredient are produced and formulated using either the anhydrate or monohydrate form of the compound. The extended release formulation approach uses poly(D,L-lactide) (PLA), poly(D,L-lactide-co-glycolide) (PLGA) polymers or a combination of PLA-PLGA polymers to encapsulate 3-(3-methoxy-4-((4-methoxybenzyl)oxy)benzyl)-6-(1-methyl-1H-pyrazol-4-yl)-3H-imidazo[4,5-b]pyridin-2-amine (the active pharmaceutical ingredient [API] or drug substance [DS]) to produce a drug product [DP] solution of injectable microcapsules. These formulations can provide sustained, or greater than 3 months, exposure of the drug to the body. A summary of the different polymers used in the preparation of the extended release formulations of this example is provided in Table 3.

TABLE 3

Polymers Used in 3-(3-Methoxy-4-((4-methoxybenzyl)oxy)benzyl)-6-(1-methyl-1H-pyrazol-4-yl)-3H-imidazo[4,5-b]pyridin-2-amine Monohydrate Extended Release Formulations

| Evonik Polymer Reference Code | Polymer Name | General Structure | Inherent Viscosity* (g/mol) | End Group |
|---|---|---|---|---|
| R202H | Poly(D,L-lactide) [PLA] | 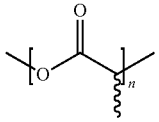 | 0.16-0.24 | Acid |
| R202S | Poly(D,L-lactide) [PLA] | 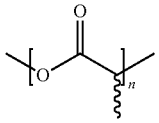 | 0.16-0.24 | Ester |

TABLE 3-continued

Polymers Used in 3-(3-Methoxy-4-((4-methoxybenzyl)oxy)benzyl)-6-(1-methyl-1H-pyrazol-4-yl)-3H-imidazo[4,5-b]pyridin-2-amine Monohydrate Extended Release Formulations

| Evonik Polymer Reference Code | Polymer Name | General Structure | Inherent Viscosity* (g/mol) | End Group |
|---|---|---|---|---|
| R203H | Poly(D,L-lactide) [PLA] | | 0.25-0.35 | Acid |
| R203S | Poly(D,L-lactide) [PLA] | | 0.25-0.35 | Ester |
| RG502H | Poly(D,L-lactide-co-glycolide) 50:50 [PLGA] | | 0.16-0.24 | Acid |
| RG752H | Poly(D,L-lactide-co-glycolide) 75:25 [PLGA] | | 0.14-0.22 | Acid |

*Inherent Viscosity is measured at 0.1% w/v in CHCl$_3$ at 25° C., with a Ubbelhode size 0c glass capillary viscometer.

Source: http://www.resomer.com/product/biodegradable-polymers/en/pharma-polymers/products/pages/bioresorbable-polymer.aspx The extended release pharmaceutical formulations of Trk inhibitors with 3-(3-methoxy-4-((4-methoxybenzyl)oxy)benzyl)-6-(1-methyl-1H-pyrazol-4-yl)-3H-imidazo[4,5-b]pyridin-2-amine as the active ingredient use bioerodible polymers, poly(D,L-lactide) and/or poly(D,L-lactide-co-glycolide), to alter the control of release of the active ingredient from drug particle dissolution to polymer hydrolysis. Using the appropriate combination of polymers and active ingredient loading, the drug release rate can be controlled to result in 3 or more months of exposure. Particular combinations of PLGA/PLA polymers and 3-(3-methoxy-4-((4-methoxybenzyl)oxy)benzyl)-6-(1-methyl-1H-pyrazol-4-yl)-3H-imidazo[4,5-b]pyridin-2-amine are combined in a manner that extends the duration of drug release to greater than 3 months; these formulations are discussed further in this example.

Example 3-1: Effect of 3-(3-methoxy-4-((4-methoxybenzyl)oxy)benzyl)-6-(1-methyl-1H-pyrazol-4-yl)-3H-imidazo[4,5-b]pyridin-2-amine Loading on in vitro Release Profile Pharmaceutical compositions comprising microspheres of 3-(3-methoxy-4-((4-methoxybenzyl)oxy)benzyl)-6-(1-methyl-1H-pyrazol-4-yl)-3H-imidazo[4,5-b]pyridin-2-amine were prepared by solvent extraction. The amounts of 3-(3-methoxy-4-((4-methoxybenzyl)oxy)benzyl)-6-(1-methyl-1H-pyrazol-4-yl)-3H-imidazo[4,5-b]pyridin-2-amine and PLA/PGLA polymer masses used to prepare each batch are presented in Table 4. The in vitro release (IVR) kinetics of these various formulations were examined.

TABLE 4

Compositions of Microspheres[‡] - 12% API/9:1 R202H:752H, 16% API/9:1 R202H:752H and 20% API/9:1 R202H:752H

| Batch# | GZ389988[†] Loading | GZ389988 weight (mg) | Polymer Ratio | Polymer Amount (mg)* |
|---|---|---|---|---|
| 1 | 12% | 36 | 9:1 R202H:752H | 234:26 |
| 2 | 16% | 50 | 9:1 R202H:752H | 234:26 |
| 3 | 20% | 65 | 9:1 R202H:752H | 234:26 |

[‡]Prepared by solvent extraction
[†]GZ389988 = 3-(3-methoxy-4-((4-methoxybenzyl)oxy)benzyl)-6-(1-methyl-1H-pyrazol-4-yl)-3H-imidazo[4,5-b]pyridin-2-amine
*Total Polymer Amount = 260 mg 3-(3-methoxy-4-((4-methoxybenzyl)oxy)benzyl)-6-(1-methyl-1H-pyrazol-4-yl)-3H-imidazo[4,5-b]pyridin-2-amine was dissolved in 2 mL of 9:1 dichloromethane (DCM):methanol (MeOH) with gentle heating (~30 minutes). Polymers were added and dissolved over 30 minutes. Separately, 39 mL of cold, sterile-filtered polyvinylamine (PVA) solution (5% w/v in water) was placed in a 250 mL beaker equipped with a 7.9×38.1 mm Teflon magnetic stir bar. The beaker was placed in an ice bath on an IKA RCT basic stir plate set at 500 rpm. The polymer/drug solution was filtered into the PVA solution using a Pall Acrodisc 0.2 μm PTFE syringe filter attached to a 5 cc glass Hamilton syringe. Upon addition, the polymer/drug solution formed an emulsion. After 1 minute, 160 mL of cold deionized water was added. After 5 minutes, the stir speed was decreased to 300 rpm. The microspheres were formed by solvent extraction over 3 hours. Microspheres were sieved through 75 μm and 38 μm stacked sieves using cold 0.1% Kolliphor P 407 in deionized water; the 38-75 μm fraction was collected and the excess rinse solution was removed. The microspheres were frozen at −80° C. and lyophilized.

The IVR kinetics of the release of 3-(3-methoxy-4-((4-methoxybenzyl)oxy)benzyl)-6-(1-methyl-1H-pyrazol-4-yl)-3H-imidazo[4,5-b]pyridin-2-amine from the microsphere formulations was determined by preparing a 2% (w/v) aqueous suspension of microspheres in 0.2% hyaluronic acid+0.2% Kolliphor P 407, intended to mimic the intra-articular environment of the knee. In triplicate, volumes of the suspensions containing a theoretical loading of 500 μg 3-(3-methoxy-4-((4-methoxybenzyl)oxy)benzyl)-6-(1-methyl-1H-pyrazol-4-yl)-3H-imidazo[4,5-b]pyridin-2-amine were pipeted into separate 50 mL glass centrifuge tubes containing 0.5% sodium dodecyl sulfate in PBS, pH 7.4 release media. The tubes were placed on their side in a reciprocal shaker incubator at 37° C. At each timepoint, the microspheres were allowed to settle and 1 mL of release media was sampled and replaced. To determine the actual total mass of 3-(3-methoxy-4-((4-methoxybenzyl)oxy)benzyl)-6-(1-methyl-1H-pyrazol-4-yl)-3H-imidazo[4,5-b]pyridin-2-amine in the IVR samples, the same volumes of suspensions used for the release study were sampled (in triplicate) and 10 mL dimethyl sulfoxide was added. The samples were sonicated, gently heated and placed on a rocker at room temperature to dissolve. These samples were analyzed for total 3-(3-methoxy-4-((4-methoxybenzyl)oxy)benzyl)-6-(1-methyl-1H-pyrazol-4-yl)-3H-imidazo[4,5-b]pyridin-2-amine content using HPLC-UV. A cumulative IVR profile was plotted as percentage of actual 3-(3-methoxy-4-((4-methoxybenzyl)oxy)benzyl)-6-(1-methyl-1H-pyrazol-4-yl)-3H-imidazo[4,5-b]pyridin-2-amine loading versus time.

3-(3-methoxy-4-((4-methoxybenzyl)oxy)benzyl)-6-(1-methyl-1H-pyrazol-4-yl)-3H-imidazo[4,5-b]pyridin-2-amine encapsulation efficiency was determined by dividing the actual drug loading by the theoretical loading. To determine the actual loading, accurately weighed masses of 3-(3-methoxy-4-((4-methoxybenzyl)oxy)benzyl)-6-(1-methyl-1H-pyrazol-4-yl)-3H-imidazo[4,5-b]pyridin-2-amine loaded microspheres were dissolved in dimethyl sulfoxide and the 3-(3-methoxy-4-((4-methoxybenzyl)oxy)benzyl)-6-(1-methyl-1H-pyrazol-4-yl)-3H-imidazo[4,5-b]pyridin-2-amine concentration was measured by HPLC-UV.

IVR profiles showed that drug loading levels above 16% (w/w) showed a burst release (FIG. 5). The cause for this burst was identified by differential scanning calorimetry (DSC) and scanning electron microscopy (SEM). DSC analysis indicated that drug loading levels above 16% (w/w) showed drug crystallization in the microspheres as evidenced by a melt endotherm at 130-150° C. (FIG. 6). Drug crystallization was also revealed by SEM, where drug loading levels above 16% showed drug crystals on microsphere surfaces (FIG. 7).

FIG. 6 demonstrates that 20% microspheres show a melting endotherm between 130 150° C. confirming the presence of surface drug crystals. FIG. 7 and FIG. 8 show SEMs of 3-(3-methoxy-4-((4-methoxybenzyl)oxy)benzyl)-6-(1-methyl-1H-pyrazol-4-yl)-3H-imidazo[4,5-b]pyridin-2-amine-loaded microspheres at 1500×. FIG. 7, 16% drug-loaded microspheres, shows no drug crystals (drug is amorphous); FIG. 8, 20% drug-loaded microspheres, shows surface drug crystals.

The effect of drug crystallization on IVR was also demonstrated using related microsphere compositions. FIG. 9 shows the IVR of 3-(3-methoxy-4-((4-methoxybenzyl)oxy)benzyl)-6-(1-methyl-1H-pyrazol-4-yl)-3H-imidazo[4,5-b]pyridin-2-amine from microspheres prepared with R202H polymer. FIG. 10 shows the IVR of 3-(3-methoxy-4-((4-methoxybenzyl)oxy)benzyl)-6-(1-methyl-1H-pyrazol-4-yl)-3H-imidazo[4,5-b]pyridin-2-amine from microspheres prepared with a 9.5:0.5 ratio of R202H and RG752H polymers. In these examples, drug loading levels above 16% (w/w) showed burst release; the extent of drug burst was directly related to the drug loading level.

Example 3-2: Effect Poly-Lactide and Poly-Lactide-co-Glycolide Polymer Blends on In Vitro Release Profile of 3-(3-methoxy-4-((4-methoxybenzyl)oxy)benzyl)-6-(1-methyl-1H-pyrazol-4-yl)-3H-imidazo[4,5-b]pyridin-2-amine Example 3-2-1: 16% API/R202H, 16% API/9.0:0.5 R202H:RG752H and 16% API/9:1 R202H:752H Microspheres Pharmaceutical compositions comprising 16% 3-(3-methoxy-4-((4-methoxybenzyl)oxy)benzyl)-6-(1-methyl-1H-pyrazol-4-yl)-3H-imidazo[4,5-b]pyridin-2-amine in R202H, 9.0:0.5 R202H:RG752H and 9:1 R202H:752H and 16% 3-(3-methoxy-4-((4-methoxybenzyl)oxy)benzyl)-6-(1-methyl-1H-pyrazol-4-yl)-3H-imidazo[4,5-b]pyridin-2-amine in R202H, 9.0:0.5 R202H:RG502H and 9:1 R202H:RG502H were prepared to assess the effect of differing polymer blends on the in vitro release kinetics of 3-(3-methoxy-4-((4-methoxybenzyl)oxy)benzyl)-6-(1-methyl-1H-pyrazol-4-yl)-3H-imidazo[4,5-b]pyridin-2-amine. Table 5 presents the drug and polymer masses used to prepare each batch. The method used to prepare these formulations is described in Example 3-1.

TABLE 5

3-(3-methoxy-4-((4-methoxybenzyl)oxy)benzyl)-6-(1-methyl-1H-pyrazol-4-yl)-3H-imidazo[4,5-b]pyridin-2-amine Microsphere Formulations with Poly-lactide and Poly-lactide-co-glycolide Polymer Blends (16% API/R202H, 16% API/9.0:0.5 R202H:RG752H and 16% API/9:1 R202H:RG752H)

| Batch# | GZ389988† Loading | GZ389988 weight (mg) | Polymer Ratio | Polymer Amount (mg)* |
|---|---|---|---|---|
| 4 | 16% | 50 mg | R202H | 260 |
| 5 | 16% | 50 mg | 9.5:0.5 R202H:RG752H | 247:13 |
| 6 | 16% | 50 mg | 9:1 R202H:RG752H | 234:26 |

‡Prepared by solvent extraction
†GZ389988 = 3-(3-methoxy-4-((4-methoxybenzyl)oxy)benzyl)-6-(1-methyl-1H-pyrazol-4-yl)-3H-imidazo[4,5-b]pyridin-2-amine
*Total Polymer Amount = 260 mg Encapsulation efficiency and IVR analyses were performed as described in Example 3-1. The encapsulation efficiency for formulations 4, 5, and 6 were 96.1±2.6%, 87.8±6.3%, and 77.7±8.6% respectively.

Microspheres prepared using 16% 3-(3-methoxy-4-((4-methoxybenzyl)oxy)benzyl)-6-(1-methyl-1H-pyrazol-4-yl)-

3H-imidazo[4,5-b]pyridin-2-amine in R202H polymer exhibited a biphasic release rate, with a slow initial release rate from 0-70 days followed by a faster secondary release rate from 70-110 days (FIG. 11). The blending of a more hydrophilic polymer, RG752H (75:25 PLGA), into the PLA microsphere formulations increased the initial rate of release. This PLGA polymer allowed faster water uptake into the microspheres leading to the rate increase. At the ratio of 9:1 R202H:RG752H, the initial release matched the secondary release rate, producing a pseudo zero-order release profile over 3 months (FIG. 11).

Example 3-2-2: 16% API/R202H, 16% API/9.5:0.5 R202H:RG502H and 16% API/9:1 R202H:RG502H Microspheres Pharmaceutical compositions comprising 16% 3-(3-methoxy-4-((4-methoxybenzyl)oxy)benzyl)-6-(1-methyl-1H-pyrazol-4-yl)-3H-imidazo[4,5-b]pyridin-2-amine in R202H, 9.0:0.5 R202H:RG502H and 9:1 R202H:RG502H were prepared to assess the effect of differing polymer blends on the in vitro release kinetics of 3-(3-methoxy-4-((4-methoxybenzyl)oxy)benzyl)-6-(1-methyl-1H-pyrazol-4-yl)-3H-imidazo[4,5-b]pyridin-2-amine. Table 6 presents the drug and polymer masses used to prepare each batch. The method used to prepare these formulations is described in Example 3-1.

TABLE 6

Compositions of Microspheres‡ - 16% API/R202H, 16% API/9.5:0.5 R202H:RG502H and 16% API/9:1 R202H:RG502H

| Batch# | GZ389988† Loading | GZ389988 weight (mg) | Polymer Ratio | Polymer Amount (mg)* |
|---|---|---|---|---|
| 7 | 16% | 50 mg | R202H | 260 |
| 8 | 16% | 50 mg | 9.5:0.5 R202H:RG502H | 247:13 |
| 9 | 16% | 50 mg | 9:1 R202H:RG502H | 234:26 |

‡Prepared by solvent extraction
†GZ389988 = 3-(3-methoxy-4-((4-methoxybenzyl)oxy)benzyl)-6-(1-methyl-1H-pyrazol-4-yl)-3H-imidazo[4,5-b]pyridin-2-amine
*Total Polymer Amount = 260 mg Encapsulation efficiency and IVR analyses were performed as described in Example 3-1. The encapsulation efficiency for formulations 7, 8, and 9 were 96.1±2.6%, 91.7±3.3%, and 94.2±2.5% respectively.

Microspheres prepared using 16% 3-(3-methoxy-4-((4-methoxybenzyl)oxy)benzyl)-6-(1-methyl-1H-pyrazol-4-yl)-3H-imidazo[4,5-b]pyridin-2-amine in R202H polymer exhibited a biphasic release rate, with a slow initial release rate from 0-70 days followed by a faster secondary release rate from 70-110 days (FIG. 12). The blending of a more hydrophilic 50:50 PLGA polymer (RG752H) into the PLA microsphere formulations increased the initial rate of release. RG752H allowed faster water uptake into the microspheres, leading to this rate increase. At the ratio of 9.5:0.5 R202H:RG502H, the initial release matched the secondary release rate, producing a pseudo zero-order release profile over 6 months (FIG. 12).

Example 3-3: Preparation and Characterization of Microsphere Formulations Showing Zero-Order In Vitro Release Kinetics Over 180 Days Pharmaceutical compositions comprising 15% 3-(3-methoxy-4-((4-methoxybenzyl)oxy)benzyl)-6-(1-methyl-1H-pyrazol-4-yl)-3H-imidazo[4,5-b]pyridin-2-amine in 9:1 R203H:RG752H and 16% 3-(3-methoxy-4-((4-methoxybenzyl)oxy)benzyl)-6-(1-methyl-1H-pyrazol-4-yl)-3H-imidazo[4,5-b]pyridin-2-amine in 9.0:0.5 R202H:RG502H were prepared and analyzed for in vitro release kinetics. Table 7 presents the drug and polymer masses used to prepare each batch.

TABLE 7

Compositions of Microspheres‡ - 15% API/9:1 R203H:RG502H and 16% API/9.5.0.5 R202H:RG502H)

| Batch# | GZ389988† Loading | GZ389988 weight (mg) | Polymer Ratio | Polymer Amount (mg)* |
|---|---|---|---|---|
| 10 | 15% | 46 mg | 9:1 R203H:RG752H | 234:26 |
| 11 | 16% | 50 mg | 9.5:0.5 R202H:RG502H | 247:13 |

‡Prepared by solvent extraction
†GZ389988 = 3-(3-methoxy-4-((4-methoxybenzyl)oxy)benzyl)-6-(1-methyl-1H-pyrazol-4-yl)-3H-imidazo[4,5-b]pyridin-2-amine
*Total Polymer Amount = 260 mg Encapsulation Efficiency and IVR Analyses were Performed as Described in Example 3-1. The encapsulation efficiency for formulations 10 and 11 were 89.7±2.1% and 91.7±3.3% respectively.

Microspheres prepared using 15% 3-(3-methoxy-4-((4-methoxybenzyl)oxy)benzyl)-6-(1-methyl-1H-pyrazol-4-yl)-3H-imidazo[4,5-b]pyridin-2-amine in R203H:752H polymers at a ratio of 9:1 and 16% 3-(3-methoxy-4-((4-methoxybenzyl)oxy)benzyl)-6-(1-methyl-1H-pyrazol-4-yl)-3H-imidazo[4,5-b]pyridin-2-amine in R202H:RG502H polymers at a ratio of 9.5:0.5 exhibited a pseudo zero-order release profile over 6 months (FIG. 13).

Example 3-4: Effect of Co-Solvent Systems in Preparation on In Vitro Release Profile of 3-(3-methoxy-4-((4-methoxybenzyl)oxy)benzyl)-6-(1-methyl-1H-pyrazol-4-yl)-3H-imidazo[4,5-b]pyridin-2-amine

Example 3-4-1: 16% API/9:1 R202H:RG752H as Prepared in 9:1 DCM:MeOH, 9:0.5:0.5 DCM:MeOH:BA, 9:5 DCM:BA and 9:1 DCM:BA Pharmaceutical compositions comprising 16% 3-(3-methoxy-4-((4-methoxybenzyl)oxy)benzyl)-6-(1-methyl-1H-pyrazol-4-yl)-3H-imidazo[4,5-b]pyridin-2-amine loaded microspheres in 9:1 R202H:RG752H were prepared using various co-solvent solutions with differing ratios of the solvents dichloromethane (DCM), methanol (MeOH) and benzyl alcohol (BA). The ratios used were 9:1 DCM:MeOH, 9:0.5:0.5 DCM:MeOH:BA, 9.5:0.5 DCM:BA, and 9:1 DCM:BA. Refer to Table 8 for drug, polymers and co-solvents used to prepare each batch. The method used to prepare these formulations is described in Example 3-1.

TABLE 8

Compositions of Microspheres[‡] Prepared with Various
Co-Solvent Systems - 16% API/9:1 R203H:RG752H

| Batch# | GZ389988[†] Loading | GZ389988 weight (mg) | Polymer Ratio | Polymer Amount. (mg)* | Co-Solvent System |
|---|---|---|---|---|---|
| 12 | 16% | 50 mg | 9:1 R202H:RG752H | 234:26 | 9:1 DCM:MeOH |
| 13 | 16% | 50 mg | 9:1 R202H:RG752H | 234:26 | 9:0.5:0.5 DCM:MeOH:BA |
| 14 | 16% | 50 mg | 9:1 R202H:RG752H | 234:26 | 9.5:0.5 DCM:BA |
| 15 | 16% | 50 mg | 9:1 R202H:RG752H | 234:26 | 9:1 DCM:BA |

[‡]Prepared by solvent extraction (various co-solvent systems)
[†]GZ389988 = 3-(3-methoxy-4-((4-methoxybenzyl)oxy)benzyl)-6-(1-methyl-1H-pyrazol-4-yl)-3H-imidazo[4,5-b]pyridin-2-amine
*Total Polymer Amount = 260 mg Encapsulation efficiency and IVR analyses were performed as described in Example 3-1. The encapsulation efficiency for bathes 12, 13, 14, and 15 were 77.7±8.6%, 94.9±2.0%, 90.5±2.6%, and 94.4±1.5% respectively. Benzyl alcohol was chosen to incorporate into the co-solvent systems due to its enhanced ability to solubilize 3-(3-methoxy-4-((4-methoxybenzyl)oxy)benzyl)-6-(1-methyl-1H-pyrazol-4-yl)-3H-imidazo[4,5-b]pyridin-2-amine. FIG. 14 and FIG. 15 show that benzyl alcohol can be used as part of a co-solvent system with dichloromethane or dichloromethane and methanol to produce microspheres without affecting the rates of release. This may be useful in reducing potential recrystallization of 3-(3-methoxy-4-((4-methoxybenzyl)oxy)benzyl)-6-(1-methyl-1H-pyrazol-4-yl)-3H-imidazo[4,5-b]pyridin-2-amine during microsphere production.

Example 3-4-2: Use of DCM:BA to Increase 3-(3-methoxy-4-((4-methoxybenzyl)oxy)benzyl)-6-(1-methyl-1H-pyrazol-4-yl)-3H-imidazo[4,5-b]pyridin-2-Amine Loading Pharmaceutical compositions comprising 16% and 25% 3-(3-methoxy-4-((4-methoxybenzyl)oxy)benzyl)-6-(1-methyl-1H-pyrazol-4-yl)-3H-imidazo[4,5-b]pyridin-2-amine in 9:1 R202H:RG752H, 30% and 40% 3-(3-methoxy-4-((4-methoxybenzyl)oxy)benzyl)-6-(1-methyl-1H-pyrazol-4-yl)-3H-imidazo[4,5-b]pyridin-2-amine in R202H, and 25%, 30%, 40% and 50% 3-(3-methoxy-4-((4-methoxybenzyl)oxy)benzyl)-6-(1-methyl-1H-pyrazol-4-yl)-3H-imidazo[4,5-b]pyridin-2-amine in R203H were prepared using varying volumes of dichloromethane (DCM) and benzyl alcohol (BA). Refer to Table 9 for drug and polymer masses and solvent volumes used to prepare each batch. The method used to prepare these formulations is described in Example 3-1.

TABLE 9

Compositions of Microspheres[‡] Prepared with DCM:BA
Co-Solvent System - 16% API/9:1 R202H:RG752H, 25% API/9:1
R202H:RG752H, 30% API/R202H, 40% API/R202H, 25% API/R203H,
30% API/R203H, 40% API/R203H, 50% API/R203H

| Batch# | GZ389988[†] Loading | GZ389988 weight (mg) | Polymer Ratio | Polymer Amount (mg)* | Co-Solvent System [volume of solvent + volume of solvent (mL)] |
|---|---|---|---|---|---|
| 16 | 16% | 50 mg | 9:1 R202H:RG752H | 234:26 | 0.2 mL BA + 1.8 mL DCM |
| 17 | 25% | 84 mg | 9:1 R202H:RG752H | 234:26 | 0.2 mL BA + 1.8 mL DCM |
| 18 | 30% | 112 mg | R202H | 260 | 0.26 mL BA + 1.2 mL DCM |
| 19 | 40% | 174 mg | R202H | 260 | 0.4 mL BA + 1.2 mL DCM |
| 20 | 40% | 174 mg | R202H | 260 | 0.5 mL BA + 1.2 mL DCM |
| 21 | 25% | 84 mg | R203H | 260 | 0.2 mL BA + 1.8 mL DCM |
| 22 | 30% | 112 mg | R203H | 260 | 0.2 mL BA + 1.8 mL DCM |
| 23 | 40% | 174 mg | R203H | 260 | 0.4 mL BA + 1.2 mL DCM |
| 24 | 40% | 174 mg | R203H | 260 | 0.5 mL BA + 1.2 mL DCM |

TABLE 9-continued

Compositions of Microspheres‡ Prepared with DCM:BA
Co-Solvent System - 16% API/9:1 R202H:RG752H, 25% API/9:1
R202H:RG752H, 30% API/R202H, 40% API/R202H, 25% API/R203H,
30% API/R203H, 40% API/R203H, 50% API/R203H

| Batch# | GZ389988† Loading | GZ389988 weight (mg) | Polymer Ratio | Polymer Amount (mg)* | Co-Solvent System [volume of solvent + volume of solvent (mL)] |
|---|---|---|---|---|---|
| 25 | 50% | 260 mg | R203H | 260 | 0.5 mL BA + 1.2 mL DCM |
| 26 | 50% | 26 mg | R203H | 260 | 0.61 mL BA + 1.2 mL DCM |

‡Prepared by solvent extraction
†GZ389988 = 3-(3-methoxy-4-((4-methoxybenzyl)oxy)benzyl)-6-(1-methyl-1H-pyrazol-4-yl)-3H-imidazo[4,5-b]pyridin-2-amine
*Total Polymer Amount = 260 mg Encapsulation efficiency and IVR analyses were performed as described in Example 3-1. The encapsulation efficiency for the formulations produced with varying volumes of dichloromethane (DCM) and benzyl alcohol (BA) were:

| Batch | Encapsulation Efficiency |
|---|---|
| 16 | 94.4 ± 1.5% |
| 17 | 96.0 ± 1.8% |
| 18 | 99.2 ± 3.6% |
| 19 | 94.0 ± 1.0% |
| 20 | 100.5 ± 1.0% |
| 21 | 91.2 ± 0.5% |
| 22 | 90.2 ± 2.8% |
| 23 | 95.5 ± 6.8% |
| 24 | 95.4 ± 3.1% |
| 25 | 95.0 ± 0.8% |
| 26 | 94.7 ± 1.7% |

Benzyl alcohol was chosen to incorporate into the co-solvent systems due to its enhanced ability to solubilize 3-(3-methoxy-4-((4-methoxybenzyl)oxy)benzyl)-6-(1-methyl-1H-pyrazol-4-yl)-3H-imidazo[4,5-b]pyridin-2-amine. FIG. 10 shows that benzyl alcohol can be used as part of a co-solvent system with dichloromethane to produce microspheres with loadings as high as 50% (w/w). Some of the release profiles shown have minimal burst release and kinetics that should achieve 3-6 month duration. The volume of benzyl alcohol used in the process effects the burst release of 3-(3-methoxy-4-((4-methoxybenzyl)oxy)benzyl)-6-(1-methyl-1H-pyrazol-4-yl)-3H-imidazo[4,5-b]pyridin-2-amine. Reducing the amount of benzyl alcohol in the solvent system, while still maintaining the solubility of the API, 3-(3-methoxy-4-((4-methoxybenzyl)oxy)benzyl)-6-(1-methyl-1H-pyrazol-4-yl)-3H-imidazo[4,5-b]pyridin-2-amine, in the polymer solution, reduces the burst effect. Increasing API loading provides benefit by decreasing the amount of polymer administered to the patient. This is expected to improve the biocompatibility of the implant and reduce the potential for polymer accumulation after repeated administrations. In addition, increased API loadings should translate into lower per-unit manufacturing costs.

Example 3-5: Effect of Micronized Suspension Microencapsulation Process on in vitro Release Profile of 3-(3-methoxy-4-((4-methoxybenzyl)oxy)benzyl)-6-(1-methyl-1H-pyrazol-4-yl)-3H-imidazo[4,5-b]pyridin-2-amine Pharmaceutical compositions comprising 25% 3-(3-methoxy-4-((4-methoxybenzyl)oxy)benzyl)-6-(1-methyl-1H-pyrazol-4-yl)-3H-imidazo[4,5-b]pyridin-2-amine (monohydrate form) in 9:1 R202H:RG752H, 30% and 40% 3-(3-methoxy-4-((4-methoxybenzyl)oxy)benzyl)-6-(1-methyl-1H-pyrazol-4-yl)-3H-imidazo[4,5-b]pyridin-2-amine in 9:1 R203H:RG752H, 25% 3-(3-methoxy-4-((4-methoxybenzyl)oxy)benzyl)-6-(1-methyl-1H-pyrazol-4-yl)-3H-imidazo[4,5-b]pyridin-2-amine in R202H, 30% 3-(3-methoxy-4-((4-methoxybenzyl)oxy)benzyl)-6-(1-methyl-1H-pyrazol-4-yl)-3H-imidazo[4,5-b]pyridin-2-amine in R202S, and 30% 3-(3-methoxy-4-((4-methoxybenzyl)oxy)benzyl)-6-(1-methyl-1H-pyrazol-4-yl)-3H-imidazo[4,5-b]pyridin-2-amine in R203S were prepared with the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine. Refer to Table 10 for drug and polymer masses used to prepare each batch. Batches 27, 28 and 29 were prepared using 3-(3-methoxy-4-((4-methoxybenzyl)oxy)benzyl)-6-(1-methyl-1H-pyrazol-4-yl)-3H-imidazo[4,5-b]pyridin-2-amine from manufacturing bathes, while Batches 30, 31, 32, 33, 34 and 35 were prepared using 3-(3-methoxy-4-((4-methoxybenzyl)oxy)benzyl)-6-(1-methyl-1H-pyrazol-4-yl)-3H-imidazo[4,5-b]pyridin-2-amine that was micronized using a microfluidization process to ensure the particle size was less than 10 µm diameter. This example compares the difference in microspheres obtained when the polymer is dispersed in a polyvinyl alcohol (PVA) solution with or without ethyl acetate (EA), as well as API loading, polymer composition and varying polymer solution concentrations (by varying EA volume).

TABLE 10

Compositions of Microspheres[‡] Prepared with Micronized Suspension Microencapsulation Process - 16% API/9:1 R202H:RG752H, 25% API/9:1 R202H:RG752H, 30% API/R202H, 40% API/R202H, 25% API/R203H, 30% API/R203H, 40% API/R203H, 50% API/R203H

| Batch# | GZ389988[†] Loading | GZ389988 weight (mg) | Polymer Ratio | Polymer Amount (mg)* | Volume and Composition of Dispersion Solution (mL) | Ethyl Acetate Volume (mL) |
|---|---|---|---|---|---|---|
| 27 | 25% | 84 mg | 9:1 R202H:RG752H | 234:26 | 39 mL of 5% PVA | 2.6 |
| 28 | 25% | 84 mg | 9:1 R202H:RG752H | 234:26 | 39 mL of 5% PVA | 3.25 |
| 29 | 25% | 84 mg | R203H | 260 | 39 mL of 5% PVA | 2.0 |
| 30 | 30% | 112 mg | 9:1 R203H:RG752H | 234:26 | 39 mL of 5% PVA + 2.5% Ethyl Acetate | 2.0 |
| 31 | 40% | 174 mg | 9:1 R203H:RG752H | 234:26 | 39 mL of 5% PVA + 2.5% Ethyl Acetate | 2.0 |
| 32 | 30% | 112 mg | 9:1 R203H:RG752H | 234:26 | 39 mL of 5% PVA + 2.5% Ethyl Acetate | 2.0 |
| 33 | 30% | 112 mg | 9:1 R203H:RG752H | 234:26 | 39 mL of 5% PVA + 2.5% Ethyl Acetate | 2.3 |
| 34 | 30% | 112 mg | R202S | 260 | 39 mL of 5% PVA + 2.5% Ethyl Acetate | 2.0 |
| 35 | 30% | 112 mg | R203S | 260 | 39 mL of 5% PVA + 2.5% Ethyl Acetate | 2.0 |

[‡]Prepared by solvent extraction
[†]GZ389988 = 3-(3-methoxy-4-((4-methoxybenzyl)oxy)benzyl)-6-(1-methyl-1H-pyrazol-4-yl)-3H-imidazo[4,5-b]pyridin-2-amine
*Total Polymer Amount = 260 mg SEM analyses showed that the microspheres produced by encapsulating a suspension of 3-(3-methoxy-4-((4-methoxybenzyl)oxy)benzyl)-6-(1-methyl-1H-pyrazol-4-yl)-3H-imidazo[4,5-b]pyridin-2-amine were spherical with a rough surface texture due to the presence of drug crystals embedded in the surface (FIG. 16). Encapsulation efficiency and IVR analyses were performed as described in Example 3-1. The encapsulation efficiency for batch numbers 30, 31, 32, 33, 34, and 35 were 103.3±3.8%, 101.6±5.3%, 94.7±4.0%, 97.1±0.2%, 35.6±0.8% and 62.5±3.0%, respectively. Encapsulation efficiency was not performed on batches 27, 28 or 29.

The IVR profiles showed burst release ranging from 25% to 47%, followed by a lack of release after 4 days (FIG. 17). Batches were evaluated for up to 21 days.

Example 3-6: Effect of Microencapsulation Process on In Vitro Release Profile of 3-(3-methoxy-4-((4-methoxybenzyl)oxy)benzyl)-6-(1-methyl-1H-pyrazol-4-yl)-3H-imidazo[4,5-b]pyridin-2-amine Pharmaceutical compositions comprising 16% and 25% 3-(3-methoxy-4-((4-methoxybenzyl)oxy)benzyl)-6-(1-methyl-1H-pyrazol-4-yl)-3H-imidazo[4,5-b]pyridin-2-amine in 9:1 R202H:RG752H and 25% and 30% 3-(3-methoxy-4-((4-methoxybenzyl)oxy)benzyl)-6-(1-methyl-1H-pyrazol-4-yl)-3H-imidazo[4,5-b]pyridin-2-amine in R203H were prepared using a 9:1 ratio of dichloromethane (DCM):benzyl alcohol (BA). Refer to Table 11 for drug and polymer masses used to prepare each batch. The method used to prepare Batch 23 is described in Example 3-1, Batch 2. Batch 24 was prepared by dissolving 3-(3-methoxy-4-((4-methoxybenzyl)oxy)benzyl)-6-(1-methyl-1H-pyrazol-4-yl)-3H-imidazo[4,5-b]pyridin-2-amine in 5.016 g of 9:1 DCM/MeOH with gentle sonication. The two polymers were then added and dissolved.

TABLE 11

Compositions of Microspheres Prepared by Solvent Extraction and Spray Drying - 16% API/9:1 R202H:RG752H and No API/9:1 R202H:RG752H

| Batch# | GZ389988[†] Loading | GZ389988 weight (mg) | Polymer Ratio | Polymer Amount (mg)* | Microencapsulation Process |
|---|---|---|---|---|---|
| 36 | 16% | 50 mg | 9:1 R202H:RG752H | 234:26 | Solvent extraction |
| 37 | 16% | 238.8 mg | 9:1 R202H:RG752H | 1140:114 | Spray drying |
| 38 | 16% | 238.8 mg | 9:1 R202H:RG752H | 1140:114 | Spray drying |
| 39 | 16% | 238.8 mg | 9:1 R203H:RG752H | 1140:114 | Spray drying |

[†]GZ389988 = 3-(3-methoxy-4-((4-methoxybenzyl)oxy)benzyl)-6-(1-methyl-1H-pyrazol-4-yl)-3H-imidazo[4,5-b]pyridin-2-amine
*Total Polymer Amount = 260 mg for batch 23 and 1254 mg for batch 24

Spray drying was performed using a ProCepT, 4M8 unit equipped with a two fluid nozzle with a 0.4 mm opening. The spray drying conditions and parameters are listed below:

|  | Batch# | | |
| --- | --- | --- | --- |
|  | 37 | 38 | 39 |
| GZ389988 Load (%, w/w) | 16 | 16 | 16 |
| Solvent (Methylene Chloride:Methanol (v/v) | 90:10 | 90:10 | 90:10 |
| PLGA Solution Concentration (%, w/v): | 20 | 22.5 | 22.5 |
| Spray Rate (mL/min): | 0.7 | 0.7 | 0.7 |
| Atomizing Nitrogen Flow (L/min): | 4 | 4 | 4 |
| Spray Amount (g): | 6.4 | 5.8 | 5.8 |
| Inlet Temperature (° C.): | 50 | 50 | 50 |
| Chamber Temperature (° C.): | 41-43 | 40.7 | 40.0 |
| Exhaust Temperature (° C.): | 27.4 | 22.0 | 22.1 |
| Nitrogen Flow (m³/min): | 0.35 | 0.35 | 0.35 |
| Transfer Tube Pressure (mBar): | 31-32 | 31-32 | 32 |
| Yield (%, w/w) | 72.8 | 76.7 | 51.6 |

SEM analyses showed that solvent extraction microspheres were spherical with a smooth surface texture and spray dried microspheres were spherical with some surface texture (FIG. 18 and FIG. 19). Encapsulation efficiency and IVR analyses were performed as described in Example 3-1. The encapsulation efficiencies for solvent extraction batch 36 and spray drying batches 37 and 38 were 107.4±11.6%, 91.4±4.3%, and 92.6±3.6%, respectively.

The two microencapsulation processes produced microspheres with near-zero-order release profiles. FIG. 18 and FIG. 19 show SEMs of 3-(3-methoxy-4-((4-methoxybenzyl)oxy)benzyl)-6-(1-methyl-1H-pyrazol-4-yl)-3H-imidazo[4,5-b]pyridin-2-amine-loaded microspheres at 1000×. The IVR profiles show different release rates (FIG. 20); the spray dried formulation achieves the desired duration of delivery of 3-6 months.

Example 3-7: Effect 1% 10 kDa PEG or 1% Poloxamer 407 on In Vitro Release Profile of Spray Dried Microspheres of 16% (w/w) 3-(3-methoxy-4-((4-methoxybenzyl)oxy)benzyl)-6-(1-methyl-1H-pyrazol-4-yl)-3H-imidazo[4,5-b]pyridin-2-amine This experiment was performed to determine if the addition of a hydrophilic additive can be used to accelerate the in vitro release rate of GZ389988 from PLA/PGA microspheres. In this experiment, microspheres prepared (no additives) were compared with microspheres prepared with either 1% 10 kDa PEG or 1% Poloxamer 407. Table 12 details the drug and polymer masses used to prepare each batch.

Spray drying was performed using a ProCepT, 4M8 unit equipped with a bi-fluid nozzle with a 0.4 mm opening. The spray drying conditions and parameters are listed below:

|  | Batch# | | |
| --- | --- | --- | --- |
|  | 40 | 41 | 42 |
| GZ389988 Load (%, w/w) | 16 | 16 | 16 |
| PLGA Solution Concentration (%, w/v): | 22.5 | 22.5 | 22.5 |
| Spray Rate (mL/min): | 0.7 | 0.7 | 0.7 |
| Air Flow (L/min): | 0.35 | 0.35 | 0.35 |
| Atomizing Nitrogen Flow (L/min): | 4 | 4 | 4 |
| Chiller Temperature (° C.): | -4 | -4 | -4 |
| Inlet Temperature (° C.): | 50 | 50 | 50 |
| Chamber Temperature (° C.): | 40 | 40 | 40 |
| Exhaust Temperature (° C.): | 29 | 29 | 29 |
| Pre-Cyclone Pressure (mBar): | 27-30 | 27-30 | 27-30 |

SEM analyses showed that spray dried microspheres prepared with or without hydrophilic additives showed a similar size distribution and surface texture; all spray dried microspheres were spherical with some surface texture (FIG. 21, FIG. 22, and FIG. 23). Encapsulation efficiency and IVR analyses were performed as described in Example 3-1. The encapsulation efficiencies for spray dried batch numbers 40, 41 and 42 were 102.0±16.3%, 101.7±16.3% and 100.5±16.1%, respectively.

Microspheres prepared without additives showed slow, near zero-order release of GZ389988 with approximately 20% of the active compound released over 35 days (FIG. 24). The addition of either 1% 10 kDa PEG or 1% Poloxamer 407 increased the release rate; approximately 42% of the active compound was released over 35 days. This example demonstrates that incorporation of a hydrophilic excipient accelerated the in vitro release rate of GZ389988 from PLA/PGA microspheres.

Example 4: In Vivo Studies

Example 4-1: In vivo Performance of [$^{14}$C]-3-(3-methoxy-4-((4-methoxybenzyl)oxy)benzyl)-6-(1-methyl-1H-pyrazol-4-yl)-3H-imidazo[4,5-b]pyridin-2-amine-Loaded Microspheres Following Intra-Articular Injection into a Rat Knee Joint Two formulations were selected to compare the in vitro release kinetics with the in vivo drug persistence in the rat knee joint. The formulations are presented in Table 13.

TABLE 12

Compositions of Microspheres[‡] Prepared with 1% 10 kDa PEG or 1% Poloxamer 407 - 16% API/1:1 R202H:R203H/No Additive, 16% API/1:1 R202H:R203H/31.25 mg PEG, 16% API/1:1 R202H:R203H/31.25 mg Poloxamer 407

| Batch# | GZ389988[†] Loading | GZ389988 weight (mg) | Polymer Ratio | Polymer Amount (mg:mg) | Additive Amount (mg) |
| --- | --- | --- | --- | --- | --- |
| 40 | 16% | 500 mg | 1:1 R202H:R203H | 1310:1310 | N/A |
| 41 | 16% | 500 mg | 1:1 R202H:R203H | 1297:1297 | 31.25 10 kDa PEG |
| 42 | 16% | 500 mg | 1:1 R202H:R203H | 1297:1297 | 31.25 Poloxamer 407 |

[‡]Prepared by spray drying
[†]GZ389988 = 3-(3-methoxy-4-((4-methoxybenzyl)oxy)benzyl)-6-(1-methyl-1H-pyrazol-4-yl)-3H-imidazo[4,5-b]pyridin-2-amine In vitro release testing was performed using the method described in Example 3-1. In vivo drug persistence testing was performed using [$^{14}$C]-3-(3-methoxy-4-((4-methoxybenzyl)oxy)benzyl)-6-(1-methyl-1H-pyrazol-4-yl)-3H-imidazo[4,5-b]pyridin-2-amine and unlabeled 3-(3-methoxy-4-((4-methoxybenzyl)oxy)benzyl)-6-(1-methyl-1H-pyrazol-4-yl)-3H-imidazo[4,5-b]pyridin-2-amine; the two drug forms were co-solubilized during the microencapsulation process to ensure uniform drug distribution in the microspheres. The total amount of radioactivity administered to each rat joint was ~1.2 MBq.

Evaluation of drug remaining in the rat knee joints was performed by sacrificing 2-3 rats at each time point, cryo-milling the knee joint and extracting the 3-(3-methoxy-4-((4-methoxybenzyl)oxy)benzyl)-6-(1-methyl-1H-pyrazol-4-yl)-3H-imidazo[4,5-b]pyridin-2-amine from the milled tissue. Quantitation was performed by liquid scintillation counting. The amount of radioactivity recovered in the joint was calculated by dividing the radioactive counts at each time point by the radioactive counts in rats sacrificed at 0.1 hour following treatment. The concentration of radioactive drug in rat blood (expressed as nEq/g) was plotted over time and compared to the known IC50 value for the compound.

TABLE 13

Compositions of Microspheres Tested In vivo - 16% API/9:1 202:H:RG502H and 15% API/9:1 R203H:RG752H

| Batch# | GZ389988† + [14C] GZ389988 Loading | GZ389988 weight (mg) | Polymer Ratio | Polymer Amount (mg)* |
|---|---|---|---|---|
| 43 | 16% | 50 mg | 9:1 R202H:RG502H | 234:26 |
| 44 | 15% | 47 mg | 9:1 R203H:RG752H | 234:26 |

†GZ389988 = 3-(3-methoxy-4-((4-methoxybenzyl)oxy)benzyl)-6-(1-methyl-1H-pyrazol-4-yl)-3H-imidazo[4,5-b]pyridin-2-amine
*Total Polymer Amount = 260 mg The IVR profiles for batches 40 and 41 show near-zero-order release over approximately 3-4 months and 5-6 months, respectively (FIG. 25). Following intra-articular administration into rat knee joints, Batches 43 and 44 showed drug release over 5 to 6 months; Batch 43 showed 12% remaining in the joint after 5 months and Batch 44 showed 30% of the drug remaining after 6 months (FIG. 26). The in vivo drug release rate was slightly lower compared with the IVR rate likely due to localization of the microspheres in the synovium.

FIG. 27 shows the drug concentration-time profile in blood. Following intra-articular administration of 3-(3-methoxy-4-((4-methoxybenzyl)oxy)benzyl)-6-(1-methyl-1H-pyrazol-4-yl)-3H-imidazo[4,5-b]pyridin-2-amine-loaded microspheres, the concentration of 3-(3-methoxy-4-((4-methoxybenzyl)oxy)benzyl)-6-(1-methyl-1H-pyrazol-4-yl)-3H-imidazo[4,5-b]pyridin-2-amine in the systemic compartment was slightly above the $EC_{50}$ value (cell based) during the first week, but then dropped below the $EC_{50}$ value for the duration of the experiment (5-6 months). This experiment demonstrates that 3-(3-methoxy-4-((4-methoxybenzyl)oxy)benzyl)-6-(1-methyl-1H-pyrazol-4-yl)-3H-imidazo[4,5-b]pyridin-2-amine-loaded microspheres provide sustained, local drug delivery to the knee joint with low systemic (i.e. sub-therapeutic) drug exposure.

Example 4-2: Assessing the Pharmacokinetics of GZ389988 Following a Single, Intra-Articular Injection of Three 3-(3-methoxy-4-((4-methoxybenzyl)oxy)benzyl)-6-(1-methyl-1H-pyrazol-4-yl)-3H-imidazo[4,5-b]pyridin-2-amine-Loaded Microspheres Extended Release Microsphere Formulations Three formulations were selected to compare the in vitro and in vivo pharmacokinetics in the systemic compartment following intra-articular injection in rat knee joints. The formulations are presented in Table 14.

In vitro release testing was performed using the method described in Example 3-1. In vivo performance was measured by injecting 3 male Wistar rats with a given microsphere formulation delivering either 0.1 or 1 mg of GZ389988 to the knee joint. At each time point, blood samples (~0.25 mL) were collected via a jugular vein cannula and placed into chilled tubes containing $K_2EDTA$ as the anticoagulant, mixed, and kept on ice until centrifugation. The samples were centrifuged within 1 hour of collection at a temperature of 4° C., at 3,000×g for 5 to 10 minutes. Plasma was collected after centrifugation of the blood samples into polypropylene tubes. Plasma samples were frozen on dry ice and stored frozen at −60 to −80° C. prior to LC-MS/MS analysis. The concentration of GZ389988 in rat plasma (expressed as ng/mL) was plotted over time (28 days total).

TABLE 14

Compositions and Dose of Microspheres Tested in Assessing Pharmacokinetics of GZ389988

| Formulation | Batch# | GZ389988† Loading | Polymer Ratio | Dose Administered (mg) |
|---|---|---|---|---|
| A | 45 | 16% | 9:1 R202H:RG752H | 0.1 |
| A | 46 | 16% | 9:1 R202H:RG752H | 1 |
| B | 47 | 15% | 9:1 R203H:RG752H | 0.1 |
|   | 48 | 15% | 9:1 R203H:RG752H | 1 |
| C | 49 | 40% | R203H | 0.1 |
|   | 50 | 40% | R203H | 1 |

†GZ389988 = 3-(3-methoxy-4-((4-methoxybenzyl)oxy)benzyl)-6-(1-methyl-1H-pyrazol-4-yl)-3H-imidazo[4,5-b]pyridin-2-amine The IVR profiles for Formulation and Formulation B show slow release with approximately 10% of the active compound released over 28 days. Formulation C shows slightly higher initial release over the first 5 days, followed by a decreased release rate over the remaining 23 days; approximately 22% of the active compound was released over 28 days.

Following intra-articular administration into rat knee joints, Formulations A and B showed similar plasma-drug exposure profiles over 28 days; both formulations showed $T_{max}$ values of 1-1.5 hours with a steady-state plasma levels over the duration of the experiment (0.08 and 0.8 ng/mL for the 0.1 and 1.0 mg doses, respectively). Compared with Formulations A and B, Formulation C showed a higher $C_{max}$ value and higher steady-state plasma level over the duration of the experiment (1.2 to 12 ng/mL for the 0.1 and 1.0 mg doses, respectively) (FIG. 29). These results were in good agreement with the IVR experiment results.

Example 4-3: Clinical Study to Assess the Safety, Tolerability, and Pharmacokinetics of 3-(3-Methoxy-4-((4-methoxybenzyl)oxy)benzyl)-6-(1-methyl-1H-pyrazol-4-yl)-3H-imidazo[4,5-b]pyridin-2-amine in Patients with Painful Osteoarthritis of the Knee The safety and efficacy of the monohydrate form of 3-(3-methoxy-4-((4-methoxybenzyl)oxy)benzyl)-6-(1-methyl-1H-pyrazol-4-yl)-3H-imidazo[4,5-b]pyridin-2-amine in humans is tested in a two part double blind placebo-controlled clinical study to assess the safety, tolerability, and pharmacokinetics of single escalating intra-articular doses followed by assessment of efficacy, safety, tolerability and pharmacokinetics of a single intra-articular dose in patients with painful osteoarthritis of the knee. In part one of the study, single intra-articular injections in the knee of various doses of 3-(3-methoxy-4-((4-methoxybenzyl)oxy)benzyl)-6-(1-methyl-1H-pyrazol-4-yl)-3H-imidazo[4,5-b]pyridin-2-amine monohydrate microcrystalline suspension, produced according to Example 2 above, are tested against placebo doses of 3 mL and 5 mL.

| Dose |
| --- |
| 3 mg/3 mL |
| 10 mg/3 mL |
| 30 mg/3 mL |
| 60 mg/3 mL |
| 100 mg/5 mL |

Adult men and women with a diagnosis of primary knee osteoarthritis are eligible for participation in the study. Patients are symptomatic for more than 6 months and provide written informed consent prior to any procedure related to the study. Efficacy is evaluated based on safety and tolerability (adverse events, physical examination, body weight, body temperature, clinical laboratory tests, blood pressure, heart rate, 12-lead electrocardiogram, local tolerance) at 12 weeks post-injection. Pharmacokinetics (plasma and, if possible, in synovial fluid) and pharmacodynamics are also evaluated.

Patients are followed for 84±7 days following study drug or placebo administration, with option of continuing on in a long term observational safety study with no additional study drug administration to assess long term safety and efficacy.

Example 5: Polymorphism Study of 3-(3-methoxy-4-((4-methoxybenzyl)oxy)benzyl)-6-(1-methyl-1H-pyrazol-4-yl)-3H-imidazo[4,5-b]pyridin-2-amine A polymorphism study of GZ389988 was conducted in order to identify crystal forms of 3-(3-methoxy-4-((4-methoxybenzyl)oxy)benzyl)-6-(1-methyl-1H-pyrazol-4-yl)-3H-imidazo[4,5-b]pyridin-2-amine in pure solvents and controlled mixtures of solvent and water. The techniques used as characterization tools of the polymorphs included X-Ray Powder Diffraction (XRPD), High-Resolution X-Ray Powder Diffraction (HR-XRPD) and Single Crystal X-Ray Diffraction (XRSCD), Thermogravimetric Analysis (TGA) coupled with Infrared Spectroscopy (FT-IR) or Mass Spectrometry (MS), Dynamic Vapor Sorption (DVS) of water and solvents, and Optical Microscopy (OM). These techniques are described in greater detail below.

High Resolution X-Ray Powder Diffraction (HR-XRPD)

High-resolution diagrams were recorded at ambient conditions on a Panalytical X'Pert Pro MPD powder diffractometer using the Bragg-Brentano (vertical θ-2θ configuration) parafocusing geometry coupled with a X'Celerator detector. A sealed copper anode X-ray tube was used, running at 45 kV and 40 mA levels. An incident beam monochromator (Johansson type: a symmetrically cut curved germanium (111) crystal) produced pure Cu K α 1 radiation ($\lambda$=1.54060 Å).

For each set of experiments, a thin layer of the product was deposited onto the surface of a sample holder, covered with a single-crystal silicon wafer. The wafer had been cut out according to Si (510) crystallographic orientation that, by systematic extinction, impeded any Bragg reflection from the silicon. The available angular range extended from 2 to 500 in 2θ, with a 0.0170 step size in 2θ. A variable counting time from 100 to 2500 seconds per step was used.

X-Ray Powder Diffraction (XRPD)

Other XRPD analyses were carried out on a Siemens-Brucker D8 Advance powder diffractometer, also using the Bragg-Brentano (vertical θ-θ configuration) parafocusing geometry, and an Anton-Paar TTK450 temperature chamber. A thin layer of the product was deposited onto a single-crystalline silicon wafer, cut out according to Si(510) crystallographic orientation that, by systematic extinction, impeded any Bragg reflection from the wafer. A sealed copper anode X-ray tube running at 40 kV and 35 mA levels was used. Two lines were typically emitted: CuKα1 ($\lambda$=1.5405 Å) and CuKα2 ($\lambda$=1.5443 Å). A Nickel β-filter, placed between the detector and specimen, did not altogether eliminate CuKβ ($\lambda$=1.3922 Å) radiation, which still contributed about 1% of the diffracted beam at the detector (manufacturer's data). The beam was sent through Soller slits to improve its parallelism. Variable divergence slits kept the illumination of the sample area constant. A collimator limited the diffusion between the tube and the sample. A LynxEye linear detector completed the setup. It had a 3.5°-wide detection window in angle 2θ. Diagrams were recorded in the following conditions: at ambient temperature, scans from 2 to 400 in angle 2θ. Integration times depended on experimental conditions. Evolution studies and most scans were conducted using a 0.1 s second counting time per step in 2θ. Longer integration times (up to 5 s) may have been used to characterize stable forms.

X-Ray Single Crystal Diffraction (XRSCD, Also Called SCXRD)

XRSCD data were recorded on a Bruker Smart Apex single crystal diffractometer. A molybdenum IμS microfocus X-ray source was used, running at 50 kV and 0.6 mA, emitting Mo-Kα radiation ($\lambda$=0.710731 Å). A Charge-Coupled Device (CCD chip: 4K, 62 mm) area detector was positioned at 6.0 cm. An Oxford Cryosystems nitrogen cryostat (Cryostream Plus) allowed XRSCD experiments to be carried out at 100 K.

The crystals were both mounted from a Paratone N™ oil drop onto a low background mylar MiTeGen loop. A full Ewald sphere of reflections was collected (3 omega scans of 680 frames with a frame width of 0.3°). Accumulation times depended on the crystal.

The orientation matrix and unit cell were established using the Apex2 (v2014.11-0) program suite. The 3D reflection profile and the integration of all reflections were carried out with the SAINT (v8.34A) program. The SADABS (v2014/5) program was used to correct for Lorentz and polarization effects and for absorption by the sample. The tentative space group was determined with the XPREP (v2014/2) program. The SHELXTL (v2014/7) suite was used to solve the structure by the intrinsic phasing method and to refine the solution by full-matrix least-squares calculations on $F^2$.

Polymorph Identification and Characterization

Using the above described techniques, crystal forms of 3-(3-methoxy-4-((4-methoxybenzyl)oxy)benzyl)-6-(1-methyl-1H-pyrazol-4-yl)-3H-imidazo[4,5-b]pyridin-2-amine were identified. These forms, XRPD 2θ peaks measured using $CuK_\alpha$ radiation and the conditions of formation are set forth in Table 15 below.

ment was performed at 100K on a 5×50×200 μm³ crystal, with an accumulation time of 300 s per frame. Diffractograms confirmed the crystallinity of the analyzed particle. FIG. 31 shows the HR-XRPD diagram of ethanol solvate powder (bottom) measured at room temperature, compared with XRPD diagram simulated from XRSCD data measured at 100K (top).

A suspension of 20 mg/ml of GZ389988A form monohydrate 1 (Form 1) was prepared in a mix of solvents acetone/water (99/1) or in pure acetone, and heated up at 80° C. for 1 h to achieve full dissolution. Next, the suspension

TABLE 15

Forms of 3-(3-methoxy-4-((4-methoxybenzyl)oxy)benzyl)-6-(1-methyl-1H-pyrazol-4-yl)-3H-imidazo[4,5-b]pyridin-2-amine

| Anhydrous, Hydrate or Solvate | Polymorph Number | Form Number | XRPD 2θ Peaks Measured using $CuK_\alpha$ Radiation | Conditions of Formation |
|---|---|---|---|---|
| Anhydrous | 1 | Form 2 | 3.8, 7.6, 11.0, 11.5, 13.3, 13.9 and 15.3 | Form obtained by dehydration of monohydrate 1 |
| Anhydrous | 1 | Form 3 | 6.0, 6.9, 10.9, 12.4, 12.7, 13.7 and 15.3 | Obtained at high temperature (160° C. for monohydrate 1, ~120° C. for solvates) |
| Anhydrous | 3 | Form 6/7 | 5.6, 8.1, 12.1, 14.0, 16.2 and 20.7 | Form obtained by desolvation of monohydrate 2 and of ethanol, acetonitrile and acetone 2 solvates |
| Monohydrate | 1 | Form 1 | 3.6, 7.1, 8.9, 10.4, 10.7, 12.4, 12.7 and 14.3 | See Example 1 |
| Monohydrate | 2 | Form 8 | 5.5, 6.4, 8.2, 12.5, 12.8 and 16.5 | Form deriving from ethanol, acetonitrile and acetone 2 solvates (from "$N_2/H_2O$ vapor" cycles) |
| Sesquihydrate | | Form 4 | 3.5, 7.1, 9.3, 10.3, 10.6, 12.4, 13.0 and 14.1 | Form obtained by crystallization from acetone/water |
| Ethanol Solvate | | Form 5 | 5.3, 6.3, 7.5, 11.4, 12.6, 12.8 and 15.1 | Form obtained by recrystallization of monohydrate 1 in ethanol or from ethanol solvation of anhydrous form 3 |
| Acetone Solvate | 1 | Form 9 | 6.1, 8.9, 12.1, 15.3, 16.4, 18.2 and 21.2 | Form obtained by recrystallization of monohydrate 1 in pure acetone and acetone/water 99:1 |
| Acetone Solvate | 2 | Form 10 | 5.4, 6.2, 7.4, 11.4, 12.6 and 14.8 | Form obtained by recrystallization of monohydrate 1 in pure acetone or from acetone solvation of anhydrous form 3 |
| Acetonitrile Solvate | | Form 11 | 5.3, 6.4, 7.7, 11.6, 12.8, 13.2 and 15.5 | Form obtained by recrystallization of monohydrate 1 in acetonitrile or from acetonitrile solvation of anhydrous form 3 |

Measured HR-XRPD diagrams of monohydrate Form 1, anhydrous Forms 2 and 3, as well as a simulated XRPD diagram of sesquihydrate Form 4, are plotted together in FIG. 30.

A suspension of 20 mg/ml of GZ389988A form monohydrate in mix solvent ethanol/water (99/1) was heated up at 80° C. for 1 h. The suspension was then filtered. Next, the solution was kept overnight at room temperature. After a night, crystals were observed, later identified as corresponding to the ethanol solvate form (labelled as Form 5). The physical quality of the crystal obtained by slow evaporation of a mix of ethanol and water (99/1) was appropriate to be analyzed by single crystal X-ray diffraction. The measurewas filtered. The solution was then kept at room temperature or at 5° C. After one night, crystals were visible to the bare eye, later identified as corresponding to an acetone solvate form (labelled as Form 9). The physical quality of the crystal obtained by slow evaporation of a mix of acetone and water (99/1) was appropriate to be analyzed by single crystal XR diffraction. The measurement was performed at 100K on a 100×200×2000 μm3 crystal, with an accumulation time of 30 s per frame. FIG. 32 displays the XRPD diagram for acetone solvate powder, measured at room temperature (bottom) and simulated from XRSCD at 100K (top).

In another experiment, a suspension of 20 mg/ml of GZ389988A form monohydrate 1 (Form 1) was prepared in pure acetone, and heated up at 80° C. for 1 h. Next, the suspension was filtered, and then directly cooled down to 5° C. and stored at that temperature. After one night, crystals were visible to the bare eye and similar to those obtained for acetone solvate 1, Form 9. After grinding them in suspension in a mortar, they were identified as corresponding to another acetone solvate, Form 10. FIG. 33 compares the XRPD for the two acetone solvate forms, Form 9 (bottom) and Form 10 (top).

A suspension of 20 mg/ml of GZ389988A form monohydrate in acetonitrile (ACN) was heated up at 80° C. for 4 h. The suspension was then filtered. Next, the solution was kept overnight at 40° C., then left for 2 hours to cool down to room temperature. After a night, clusters of crystals had formed at the bottom of the vial. The HR-XRPD diagram of the acetonitrile (ACN) solvate form (Form 11) is reported in FIG. 34.

Identification of Solid Crystalline Phase Forming in Acetone/Water and Acetonitrile/Water Mixed Solvents 50 mg of GZ389988A Monohydrate 1 were complemented with 2 mL of a mixture of a solvent (acetone or acetonitrile) and demineralized water, at three different weight ratios: 50/50, 80/20 and 95/5. With acetone, additional mixtures at ratios 99/1 and 98/2 were probed. After 2 hours at 80° C., the samples were filtered on a PTFE syringe filter with a nominal pore size of 0.45 μm, and stored again at 80° C. for 15 minutes after filtration.

Samples were then left to cool down overnight at 40° C., and then at room temperature for another 24 hours.

Samples were then analyzed by XRPD in a chamber saturated with the corresponding solvent. If necessary, large crystals were crushed in the vial with a spatula into a finer powder. A sample of "wet" powder was then deposited as flat as possible on the sample holder. The results of these analyses are presented in Table 16 below.

TABLE 16

Solid crystalline Phase of GZ389988A in Acetone/Water and Acetonitrile/Water Mixtures

| Solvent | Solvent/Water weight ratio | Crystalline phase(s) |
| --- | --- | --- |
| Acetone | 99/1 | Acetone solvate Form 9 |
|  | 98/2 | Monohydrate 1 |
|  | 97/3 | Monohydrate 1 |
|  | 95/5 | Monohydrate 1 |
|  | 80/20 | Monohydrate 1 |
|  | 50/50 | Monohydrate 1 |
| Acetonitrile | 95/5 | Monohydrate 1 |
|  | 80/20 | Monohydrate 1 |
|  | 50/50 | Monohydrate 1 |

Formation of solvates and hydrates from crystallization of Monohydrate 1 in ethanol, acetone, acetonitrile and acetone/water and acetonitrile/water mixtures was studied and presented in this example. Ten crystalline phases have been identified:
  Anhydrous Phase 1 (Form 2)
  Anhydrous Phase 2 (Form 3)
  Anhydrous Phase 3 (Form 6/7)
  Monohydrate 1 (Form 1)
  Monohydrate 2 (Form 8)
  Sesquihydrate (Form 4)
  Ethanol solvate (Form 5)
  Acetone solvate 1 (Form 9)
  Acetone solvate 2 (Form 10)
  Acetonitrile solvate (Form 11)

The corresponding diffractograms are plotted together in FIG. 35.

From the polymorphism study conducted on ethanol, acetone and acetonitrile, as well as on solvent mixes (acetone/water and acetonitrile/water), several conclusions can be drawn. All three pure solvents lead to the formation of solid crystalline solvate phases. Recrystallization of GZ389988A in ethanol and acetonitrile each lead to one solvate form. Two solvate forms have been obtained from recrystallization in acetone. Crystals formed in acetone/water mixed solvent systems with weight ratios of 98:2, 97:3 95:5, 80:20 and 50:50 are all in the monohydrate 1 crystalline phase. Crystals formed in acetonitrile/water mixed solvent systems with weight ratios of 95:5, 80:20 and 50:50 are also all monohydrate 1 crystals. Acetone solvate 1 has been observed to transform into a mostly amorphous solid upon desolvation. If molecular mobility is increased by the presence of vapors of mixed acetone and water, both the initial acetone solvate 1 crystals and the amorphous solid reorganize into monohydrate 1. Ethanol, acetonitrile and acetone solvate 1 exposed to a temperature of 120° C. under nitrogen desolvate into the same anhydrous crystalline phase 2. Isomorphism is observed for ethanol, acetonitrile and acetone solvate 2 forms (to be confirmed by single crystal X-ray diffraction). They all reversibly desolvate into the same anhydrous phase 3. Anhydrous phase 3 hydrates into a monohydrate form, "monohydrate 2", different from monohydrate 1.

The invention claimed is:

1. A method of treating osteoarthritis in a patient, comprising administering to the patient 3-(3-methoxy-4-((4-methoxybenzyl)oxy)benzyl)-6-(1-methyl-1H-pyrazol-4-yl)-3H-imidazo[4,5-b]pyridin-2-amine monohydrate, to thereby treat osteoarthritis.

2. A method of treating osteoarthritis in a patient, comprising administering to the patient a pharmaceutical composition comprising:
  a. a compound according to the following structural formula:

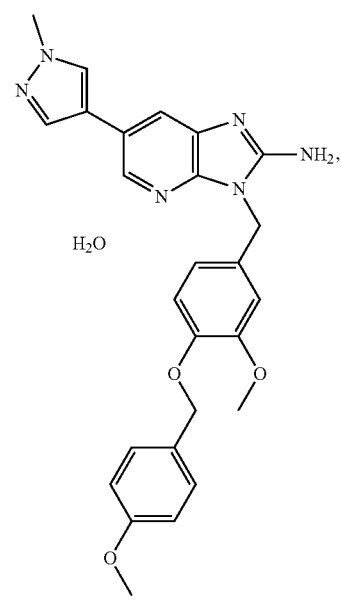

and
  b. a pharmaceutically acceptable excipient;
to thereby treat osteoarthritis.

3. The method of claim 2, wherein the pharmaceutically acceptable excipient comprises a diluent.

4. The method of claim 3, wherein the diluent is selected from sunflower oil, ammonium alginate, calcium carbonate, calcium lactate, calcium phosphate dibasic anhydrous, calcium silicate, calcium sulfate, cellulose, cellulose acetate, compressible sugar, confectioner's sugar, corn starch, pregelatinized starch, dextrin, dextrose, erythritol, ethyl cellulose, fructose, fumaric acid, glyceryl palmitostearate, inhalation lactose, isomalt, kaolin, lactitol, lactose, magnesium carbonate, magnesium oxide, maltodextrin, maltose, mannitol, a medium-chain triglyceride, microcrystalline cellulose, polydextrose, a polymethacrylate, simethicone, sodium alginate, sodium chloride, sorbitol, starch, sucrose, sulfobutylether b-cyclodextrin, talc, tragacanth, trehalose, or xylitol.

5. The method of claim 3, wherein the diluent is sorbitol.

6. The method of claim 2, wherein the pharmaceutically acceptable excipient comprises a suspending agent.

7. The method of claim 6, wherein the suspending agent is selected from acacia, agar, alginic acid, bentonite, calcium stearate, carbomer, carrageenan, cellulose, colloidal silicone dioxide, dextrin, gelatin, guar gum, hectorite, hydrophobic colloidal silica, hydroxyethyl cellulose, hydroxymethyl cellulose, hydroxypropyl cellulose, hypromellose, kaolin, magnesium aluminum silicate, a medium-chain triglyceride, methylcellulose, phenylmercuric borate, a phospholipid, poycarbophil, polyethylene glycol, a polyoxyethylene sorbitan fatty acid ester, povidone, propylene glycol alginate, saponite, sesame oil, sodium alginate, a sorbitan ester, sucrose, tragacanth, vitamin E polyethylene glycol succinate, or xanthan gum.

8. The method of claim 6, wherein the suspending agent is povidone.

9. A method of treating pain associated with osteoarthritis in a patient, comprising administering to the patient 3-(3-methoxy-4-((4-methoxybenzyl)oxy)benzyl)-6-(1-methyl-1H-pyrazol-4-yl)-3H-imidazo[4,5-b]pyridin-2-amine monohydrate, to thereby treat pain associated with osteoarthritis.

10. A method of treating pain associated with osteoarthritis in a patient, comprising administering to the patient a pharmaceutical composition comprising:

a. a compound according to the following structural formula:

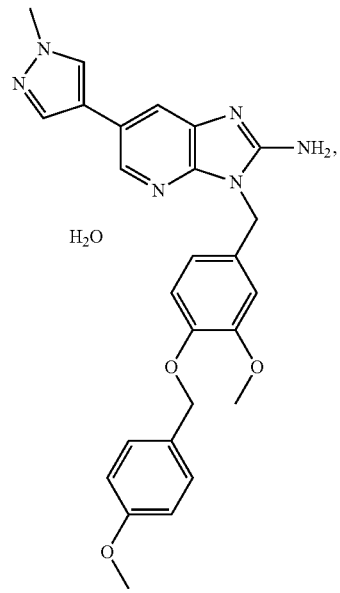 [SMILES: COc1ccc(COc2ccc(Cn3c(N)nc4cc(-c5cnn(C)c5)cnc43)cc2OC)cc1 ; O]

and
b. a pharmaceutically acceptable excipient;
to thereby treat pain associated with osteoarthritis.

11. The method of claim 10, wherein the pharmaceutically acceptable excipient comprises a diluent.

12. The method of claim 11, wherein the diluent is selected from sunflower oil, ammonium alginate, calcium carbonate, calcium lactate, calcium phosphate dibasic anhydrous, calcium silicate, calcium sulfate, cellulose, cellulose acetate, compressible sugar, confectioner's sugar, corn starch, pregelatinized starch, dextrin, dextrose, erythritol, ethyl cellulose, fructose, fumaric acid, glyceryl palmitostearate, inhalation lactose, isomalt, kaolin, lactitol, lactose, magnesium carbonate, magnesium oxide, maltodextrin, maltose, mannitol, a medium-chain triglyceride, microcrystalline cellulose, polydextrose, a polymethacrylate, simethicone, sodium alginate, sodium chloride, sorbitol, starch, sucrose, sulfobutylether b-cyclodextrin, talc, tragacanth, trehalose, or xylitol.

13. The method of claim 11, wherein the diluent is sorbitol.

14. The method of claim 10, wherein the pharmaceutically acceptable excipient comprises a suspending agent.

15. The method of claim 14, wherein the suspending agent is selected from acacia, agar, alginic acid, bentonite, calcium stearate, carbomer, carrageenan, cellulose, colloidal silicone dioxide, dextrin, gelatin, guar gum, hectorite, hydrophobic colloidal silica, hydroxyethyl cellulose, hydroxymethyl cellulose, hydroxypropyl cellulose, hypromellose, kaolin, magnesium aluminum silicate, a medium-chain triglyceride, methylcellulose, phenylmercuric borate, a phospholipid, poycarbophil, polyethylene glycol, a polyoxyethylene sorbitan fatty acid ester, povidone, propylene glycol alginate, saponite, sesame oil, sodium alginate, a sorbitan ester, sucrose, tragacanth, vitamin E polyethylene glycol succinate, or xanthan gum.

16. The method of claim 14, wherein the suspending agent is povidone.

* * * * *